(12) United States Patent
Grosschedl et al.

(10) Patent No.: US 10,822,401 B2
(45) Date of Patent: Nov. 3, 2020

(54) MZB1, A NOVEL B CELL FACTOR, AND USES THEREOF

(71) Applicant: Max-Planck-Gesellschaft zur Förderung der Wissenschaften e.V., Munich (DE)

(72) Inventors: Rudolf Grosschedl, Freiburg (DE); Henrik Flach, San Francisco, CA (US); Sola Kim, Copenhagen (DK); Marlena Duchniewicz, Freiburg (DE); Bernadette Schreiner, Huddinge (SE); Marc Rosenbaum, Freiburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 174 days.

(21) Appl. No.: 15/689,948

(22) Filed: Aug. 29, 2017

(65) Prior Publication Data

US 2018/0057573 A1 Mar. 1, 2018

Related U.S. Application Data

(60) Division of application No. 13/740,772, filed on Jan. 14, 2013, now Pat. No. 9,765,134, which is a continuation of application No. 12/935,406, filed as application No. PCT/EP2009/002349 on Mar. 31, 2009, now abandoned.

(30) Foreign Application Priority Data

Mar. 31, 2008 (EP) .................... 08006376

(51) Int. Cl.
| | | |
|---|---|---|
| *C07K 14/435* | (2006.01) | |
| *C07K 14/475* | (2006.01) | |
| *C12N 5/10* | (2006.01) | |
| *C12N 5/0781* | (2010.01) | |
| *G01N 33/53* | (2006.01) | |
| *G01N 33/566* | (2006.01) | |
| *G01N 33/68* | (2006.01) | |
| *C07K 16/18* | (2006.01) | |
| *A61K 38/00* | (2006.01) | |

(52) U.S. Cl.
CPC ............ *C07K 16/18* (2013.01); *C07K 14/475* (2013.01); *C12N 5/0635* (2013.01); *G01N 33/53* (2013.01); *G01N 33/566* (2013.01); *G01N 33/68* (2013.01); *G01N 33/6854* (2013.01); *A61K 38/00* (2013.01); *C12N 5/10* (2013.01)

(58) Field of Classification Search
CPC ...... C07K 14/47; C07K 14/475; C07K 14/52; G01N 33/68; G01N 33/6863; G01N 33/53; G01N 33/566; G01N 2333/705; G01N 2500/04; G01N 33/6872; G01N 2333/475; G01N 2333/52; G01N 2500/00; G01N 2500/10
See application file for complete search history.

(56) References Cited

U.S. PATENT DOCUMENTS 6,380,362 B1  4/2002  Watson et al.

FOREIGN PATENT DOCUMENTS

| EP | 1447412 A1 * | 2/2003 |
|---|---|---|
| WO | WO 2001/48192 A1 | 7/2001 |
| WO | WO 2001/90357 A1 | 11/2001 |

OTHER PUBLICATIONS

Shimzu et al. pERp1 is significantly up-regulated during plasma cell differentiation and contributes to the oxidative folding of immunoglobulin. Proc Natl Acad Sci USA 106(40): 17013-17018, 2009.*
van Anken et al. Efficient IgM assembly and secretion require the plasma cell induced endoplasmic reticulum protein pERp1. Proc Natl Acad Sci USA 106(40): 17019-17024, 2009.*
Arbuckle et al., "Development of Autoantibodies before the Clinical Onset of Systemic Lupus Erythematosus", *New England Journal of Medicine*, 349: 526-1533 (2003).
Axiak et al., Quantitation of free kappa light chains in serum and urine using a monoclonal antibody based inhibition enzyme-linked immunoassay. *J. Immunol. Methods*, 99: 141-147 (1987).
Biocca et al., Expression and targeting of intracellular antibodies in mammalian cells. *EMBO J.*, 9(1): 101-108 (1990).
Bonfocco et al., Characterization of a novel proapoptotic caspase-2- and caspase-9-binding protein. *J Biol Chem.*, 276: 29242-29250 (2001).
Bos et al., The potential improvement of thrombolytic therapy by targeting with bispecific monoclonal antibodies: why they are used and how they are made. *Biotherapy*, 5: 187-199 (1992).
Chazenbalk et al., "Thyroid-stimulating autoantibodies in Graves disease preferentially recognize the free A subunit, not the thyrotropin holoreceptor", *Journal of Clinical Investigation*, 110: 209-217 (2002).
Dayan et al., "Chronic Autoimmune Thyroiditis", *New England Journal of Medicine*, 335(2): 99-107 (1996).
Farrugia et al., "Myasthenia gravis with MuSK antibodies", *Practical Neurology*, 5: 356-359 (2005).

(Continued)

*Primary Examiner* — Bridget E Bunner
(74) *Attorney, Agent, or Firm* — Leydig, Voit & Mayer, Ltd.

(57) ABSTRACT

The marginal zone (MZ) and B1 subsets of B cells, which differ from conventional follicular (FO) B cells both developmentally and functionally, are involved in early responses to infectious pathogens and the production of self-reactive antibodies. A novel gene, mzb1, is expressed at high levels in MZ and B1 B cells but at low level, if at all, in FO B cells. MZB1 is involved in the regulation of proliferation, BCR-mediated signal transduction, and antibody production in B cells. Inhibitors, activators and enhancers of MZB1 expression or activity can be used as immune modulators for research and therapeutic purposes.

7 Claims, 52 Drawing Sheets

Specification includes a Sequence Listing.

(56) References Cited

OTHER PUBLICATIONS

Flach et al., Mzb1 Protein Regulates Calcium Homeostasis, Antibody Secretion, and Integrin Activation in Innate-like B Cells; *Immunity*, 33: 723-735, (Nov. 24, 2010).
Folwaczny et al., "Antinuclear Autoantibodies in Patients with Inflammatory Bowel Disease: High Prevalence in First-Degree Relatives", *Digestive Diseases and Sciences*, 42(8): 1593-1597, (1997).
Goëb et al., "Clinical significance of autoantibodies recognizing Sjögren's syndrome A (SSA), SSB, calpastatin and alpha-fodrin in primary Sjögren's syndrome", *Clinical and Experimental Immunology*, 148: 281-287 (2007).
Juengst, BMJ Jun. 28, 2003;326(7404):1410-1.
Katoh et al., MGC29506 gene, frequently down-regulated in intestinal-type gastric cancer, encodes secreted-type protein with conserved cysteine residues, *Int. J. Oncol.*, 23: 235-241 (2003).
McManus et al., Gene silencing in mammals by small interfering RNAs, *Nat. Rev. Genet.*, 3: 737-747 (2002).
Matsushita et al., "Autoantibodies directed against the protease inhibitor calpastatin in psoriasis", *Clinical and Experimental Immunology*, 139: 355-362 (2005).
Nakamura et al., "High incidence of positive autoantibodies against thyroid peroxidase and thyroglobulin in patients with sarcoidosis", *Clinical Endocrinology*, 46: 467-472 (1997).
Paul et al., "Characterization of autoantibodies", *Journal of Neuroimmunology*, 23: 133-142 (1989).
Pihoker et al., "Autoantibodies in Diabetes", *Diabetes*, 54(2): S52-S61 (2005).
Reynolds et al., Rational siRNA design for RNA interference, *Nat. Biotech.*, 22(3): 326-330 (2004).
Rosenbaum et al., "MZB1 is a DRP94 cochaperone that enables proper immunoglobulin heavy chain biosynthesis upon ER stress", *Genes & Development*, 28: 1165-1178 (2014).
Silverman & Carson, "Roles of B cells in rheumatoid arthritis," *Arthritis Res Ther*, 5(Suppl 4): S1-S6 (2003).
Steiner et al., "Autoantibodies in rheumatoid arthritis and their clinical significance", *Arthritis Research*, 4(2): S1-S5 (2002).
UniProt PERP1_Mouse (Q9D8I1). Feb. 26, 2008.
Vojdani et al., "Antibodies to myelin basic protein, myelin oligodendrocytes peptides, α-β-crystalline, lymphocyte activation and cytokine production in patients with multiple sclerosis", *Journal of Internal Medicine*, 254: 363-374 (2003).
Weiss et al., Antisense RNA gene therapy for studying and modulating biological processes. *Cell. Mol. Life Sci,*. 55: 334-358 (1999).

\* cited by examiner 0 min 30 min 0 min 30 min

A

B

SEQUENCE LISTING

```
<160> NUMBER OF SEQ ID NOS: 22

<210> SEQ ID NO 1
<211> LENGTH: 564
<212> TYPE: DNA
<213> ORGANISM: mouse
<220> FEATURE:
<221> NAME/KEY: misc_feature
<223> OTHER INFORMATION: full length MZB1 coding sequence

<400> SEQUENCE: 1
atgagactgc ctctgccact gttgctactg ttcgggtgca gggctatcct ggggagcgcc      60
ggggataggg tttccctctc ggcttcggct cccacactgg atgatgaaga aagtactcg      120 gctcatatgc cggctcacct gcgctgcgat gcctgccggg ctgtggcctt ccagatgggg     180
caacgtctgg cgaaagcaga ggctaaatct cacactccag acgccagtgg attgcaggag    240
ctgagtgaat ccacgtacac agatgtcctg gaccagacct gctctcagaa ctggcagtcc    300
tatggagttc atgaagtgaa ccagatgaag cgtctcacgg gcccaggact tagcaagggg    360
ccagagccaa gaatcagcgt gatgatttct ggggtccct ggcccaatag gctctccaag     420
acgtgtttcc actacctggg tgagtttgga gaggaccaga tctatgaagc ctaccgccaa    480
ggccaagcga atctggaggc gctgctctgt ggggcaccc atgggccctg ctcacaggag     540
atcctggccc agagagaaga gctt                                            564

<210> SEQ ID NO 2
<211> LENGTH: 188
<212> TYPE: PRT
<213> ORGANISM: mouse
<220> FEATURE:
<221> NAME/KEY: misc_feature
<223> OTHER INFORMATION: full length MZB1 amino acid sequence

<400> SEQUENCE: 2

Met Arg Leu Pro Leu Pro Leu Leu Leu Phe Gly Cys Arg Ala Ile
1               5                   10                  15

Leu Gly Ser Ala Gly Asp Arg Val Ser Leu Ser Ala Ser Ala Pro Thr
            20                  25                  30

Leu Asp Asp Glu Glu Lys Tyr Ser Ala His Met Pro Ala His Leu Arg
        35                  40                  45

Cys Asp Ala Cys Arg Ala Val Ala Phe Gln Met Gly Gln Arg Leu Ala
    50                  55                  60

Lys Ala Glu Ala Lys Ser His Thr Pro Asp Ala Ser Gly Leu Gln Glu
65                  70                  75                  80
```

Leu Ser Glu Ser Thr Tyr Thr Asp Val Leu Asp Gln Thr Cys Ser Gln
                85                  90                  95

Asn Trp Gln Ser Tyr Gly Val His Glu Val Asn Gln Met Lys Arg Leu
            100                 105                 110

Thr Gly Pro Gly Leu Ser Lys Gly Pro Glu Pro Arg Ile Ser Val Met
        115                 120                 125

Ile Ser Gly Gly Pro Trp Pro Asn Arg Leu Ser Lys Thr Cys Phe His
130                 135                 140

Tyr Leu Gly Glu Phe Gly Glu Asp Gln Ile Tyr Glu Ala Tyr Arg Gln
145                 150                 155                 160

Gly Gln Ala Asn Leu Glu Ala Leu Leu Cys Gly Gly Thr His Gly Pro
                165                 170                 175

Cys Ser Gln Glu Ile Leu Ala Gln Arg Glu Glu Leu
            180                 185

<210> SEQ ID NO 3
<211> LENGTH: 510
<212> TYPE: DNA
<213> ORGANISM: mouse
<220> FEATURE:
<221> NAME/KEY: misc_feature
<223> OTHER INFORMATION: mature MZB1 coding sequence

<400> SEQUENCE: 3
agcgccgggg atagggtttc cctctcggct tcggctccca cactggatga tgaagagaag    60
tactcggctc atatgccggc tcacctgcgc tgcgatgcct gccgggctgt ggccttccag   120
atggggcaac gtctggcgaa agcagaggct aaatctcaca ctccagacgc cagtggattg   180
caggagctga gtaatccac gtacacagat gtcctggacc agacctgctc tcagaactgg   240
cagtcctatg gagttcatga agtgaaccag atgaagcgtc tcacgggccc aggacttagc   300
aaggggccag agccaagaat cagcgtgatg atttctgggg gtcccctggcc aataggctc   360 tccaagacgt gtttccacta cctgggtgag tttggagagg accagatcta tgaagcctac   420
cgccaaggcc aagcgaatct ggaggcgctg ctctgtgggg gcacccatgg gccctgctca   480
caggagatcc tggcccagag agaagagctt                                     510

<210> SEQ ID NO 4
<211> LENGTH: 170
<212> TYPE: PRT
<213> ORGANISM: mouse
<220> FEATURE:
<221> NAME/KEY: misc_feature
<223> OTHER INFORMATION: mature MZB1 amino acid sequence

<400> SEQUENCE: 4

Ser Ala Gly Asp Arg Val Ser Leu Ser Ala Ser Ala Pro Thr Leu Asp
1               5                   10                  15

Asp Glu Glu Lys Tyr Ser Ala His Met Pro Ala His Leu Arg Cys Asp
            20                  25                  30

Ala Cys Arg Ala Val Ala Phe Gln Met Gly Gln Arg Leu Ala Lys Ala
        35                  40                  45

Glu Ala Lys Ser His Thr Pro Asp Ala Ser Gly Leu Gln Glu Leu Ser
    50                  55                  60

Glu Ser Thr Tyr Thr Asp Val Leu Asp Gln Thr Cys Ser Gln Asn Trp
65                  70                  75                  80

Gln Ser Tyr Gly Val His Glu Val Asn Gln Met Lys Arg Leu Thr Gly
                85                  90                  95

Pro Gly Leu Ser Lys Gly Pro Glu Pro Arg Ile Ser Val Met Ile Ser
                100                 105                 110

Gly Gly Pro Trp Pro Asn Arg Leu Ser Lys Thr Cys Phe His Tyr Leu
            115                 120                 125

Gly Glu Phe Gly Glu Asp Gln Ile Tyr Glu Ala Tyr Arg Gln Gly Gln
    130                 135                 140

Ala Asn Leu Glu Ala Leu Leu Cys Gly Gly Thr His Gly Pro Cys Ser
145                 150                 155                 160

Gln Glu Ile Leu Ala Gln Arg Glu Glu Leu
                165                 170

<210> SEQ ID NO 5
<211> LENGTH: 552
<212> TYPE: DNA
<213> ORGANISM: mouse
<220> FEATURE:
<221> NAME/KEY: misc_feature
<223> OTHER INFORMATION: full length MZB1 without C-terminal REEL coding
      sequence

<400> SEQUENCE: 5

```
atgagactgc ctctgccact gttgctactg ttcgggtgca gggctatcct ggggagcgcc      60
ggggataggg tttccctctc ggcttcggct cccacactgg atgatgaaga gaagtactcg     120
gctcatatgc cggctcacct cgctgcgat gcctgccggg ctgtggcctt ccagatgggg     180
caacgtctgg cgaaagcaga ggctaaatct cacactccag acgccagtgg attgcaggag     240
ctgagtgaat ccacgtacac agatgtcctg gaccagacct gctctcagaa ctggcagtcc     300
tatggagttc atgaagtgaa ccagatgaag cgtctcacgg gcccaggact tagcaagggg     360
ccagagccaa gaatcagcgt gatgatttct ggggggtccct ggcccaatag gctctccaag     420
acgtgtttcc actacctggg tgagtttgga gaggaccaga tctatgaagc ctaccgccaa     480
ggccaagcga atctggaggc gctgctctgt gggggcaccc atgggccctg ctcacaggag     540
atcctggccc ag                                                         552
```

<210> SEQ ID NO 6
<211> LENGTH: 184
<212> TYPE: PRT
<213> ORGANISM: mouse
<220> FEATURE:
<221> NAME/KEY: misc_feature
<223> OTHER INFORMATION: full length MZB1 without C-terminal REEL amino
      acid sequence

<400> SEQUENCE: 6

Met Arg Leu Pro Leu Pro Leu Leu Leu Leu Phe Gly Cys Arg Ala Ile
1               5                   10                  15

Leu Gly Ser Ala Gly Asp Arg Val Ser Leu Ser Ala Ser Ala Pro Thr
            20                  25                  30

Leu Asp Asp Glu Glu Lys Tyr Ser Ala His Met Pro Ala His Leu Arg
        35                  40                  45

Cys Asp Ala Cys Arg Ala Val Ala Phe Gln Met Gly Gln Arg Leu Ala
    50                  55                  60

Lys Ala Glu Ala Lys Ser His Thr Pro Asp Ala Ser Gly Leu Gln Glu
65                  70                  75                  80

Leu Ser Glu Ser Thr Tyr Thr Asp Val Leu Asp Gln Thr Cys Ser Gln
                85                  90                  95

Asn Trp Gln Ser Tyr Gly Val His Glu Val Asn Gln Met Lys Arg Leu

```
                100                 105                 110
Thr Gly Pro Gly Leu Ser Lys Gly Pro Glu Pro Arg Ile Ser Val Met
            115                 120                 125

Ile Ser Gly Gly Pro Trp Pro Asn Arg Leu Ser Lys Thr Cys Phe His
        130                 135                 140

Tyr Leu Gly Glu Phe Gly Glu Asp Gln Ile Tyr Glu Ala Tyr Arg Gln
145                 150                 155                 160

Gly Gln Ala Asn Leu Glu Ala Leu Leu Cys Gly Gly Thr His Gly Pro
                165                 170                 175

Cys Ser Gln Glu Ile Leu Ala Gln
            180
```

<210> SEQ ID NO 7
<211> LENGTH: 498
<212> TYPE: DNA
<213> ORGANISM: mouse
<220> FEATURE:
<221> NAME/KEY: misc_feature
<223> OTHER INFORMATION: mature MZB1 without C-terminal REEL coding
      sequence

<400> SEQUENCE: 7

```
agcgccgggg atagggtttc cctctcggct tcggctccca cactggatga tgaagagaag    60
tactcggctc atatgccggc tcacctgcgc tgcgatgcct gccgggctgt ggccttccag   120
atggggcaac gtctggcgaa agcagaggct aaatctcaca ctccagacgc cagtggattg   180
caggagctga gtgaatccac gtacacagat gtcctggacc agacctgctc tcagaactgg   240
cagtcctatg gagttcatga agtgaaccag atgaagcgtc tcacgggccc aggacttagc   300
aagggggccag agccaagaat cagcgtgatg atttctgggg gtccctggcc aataggctc   360
tccaagacgt gtttccacta cctgggtgag tttggagagg accagatcta tgaagcctac   420
cgccaaggcc aagcgaatct ggaggcgctg ctctgtgggg gcacccatgg gccctgctca   480
caggagatcc tggcccag                                                 498
```

<210> SEQ ID NO 8
<211> LENGTH: 166
<212> TYPE: PRT
<213> ORGANISM: mouse
<220> FEATURE:
<221> NAME/KEY: misc_feature
<223> OTHER INFORMATION: mature MZB1 without C-terminal REEL amino acid
      sequence

<400> SEQUENCE: 8

```
Ser Ala Gly Asp Arg Val Ser Leu Ser Ala Ser Ala Pro Thr Leu Asp
1               5                   10                  15

Asp Glu Glu Lys Tyr Ser Ala His Met Pro Ala His Leu Arg Cys Asp
            20                  25                  30

Ala Cys Arg Ala Val Ala Phe Gln Met Gly Gln Arg Leu Ala Lys Ala
        35                  40                  45

Glu Ala Lys Ser His Thr Pro Asp Ala Ser Gly Leu Gln Glu Leu Ser
    50                  55                  60

Glu Ser Thr Tyr Thr Asp Val Leu Asp Gln Thr Cys Ser Gln Asn Trp
65                  70                  75                  80

Gln Ser Tyr Gly Val His Glu Val Asn Gln Met Lys Arg Leu Thr Gly
                85                  90                  95

Pro Gly Leu Ser Lys Gly Pro Glu Pro Arg Ile Ser Val Met Ile Ser
            100                 105                 110
```

```
Gly Gly Pro Trp Pro Asn Arg Leu Ser Lys Thr Cys Phe His Tyr Leu
        115                 120                 125

Gly Glu Phe Gly Glu Asp Gln Ile Tyr Glu Ala Tyr Arg Gln Gly Gln
130                 135                 140

Ala Asn Leu Glu Ala Leu Leu Cys Gly Gly Thr His Gly Pro Cys Ser
145                 150                 155                 160

Gln Glu Ile Leu Ala Gln
                165

<210> SEQ ID NO 9
<211> LENGTH: 402
<212> TYPE: DNA
<213> ORGANISM: mouse
<220> FEATURE:
<221> NAME/KEY: misc_feature
<223> OTHER INFORMATION: amino acids 46-179 of MZB1 coding sequence

<400> SEQUENCE: 9
cacctgcgct gcgatgcctg ccgggctgtg gccttccaga tggggcaacg tctggcgaaa        60
gcagaggcta aatctcacac tccagacgcc agtggattgc aggagctgag tgaatccacg       120
tacacagatg tcctggacca gacctgctct cagaactggc agtcctatgg agttcatgaa       180
gtgaaccaga tgaagcgtct cacgggccca ggacttagca aggggccaga gccaagaatc       240
agcgtgatga tttctggggg tccctggccc aataggctct ccaagacgtg tttccactac       300
ctgggtgagt ttggagagga ccagatctat gaagcctacc gccaaggcca agcgaatctg       360
gaggcgctgc tctgtggggg cacccatggg ccctgctcac ag                         402

<210> SEQ ID NO 10
<211> LENGTH: 134
<212> TYPE: PRT
<213> ORGANISM: mouse
<220> FEATURE:
<221> NAME/KEY: misc_feature
<223> OTHER INFORMATION: amino acids 46-179 of MZB1 amino acid sequence

<400> SEQUENCE: 10

His Leu Arg Cys Asp Ala Cys Arg Ala Val Ala Phe Gln Met Gly Gln
1               5                   10                  15

Arg Leu Ala Lys Ala Glu Ala Lys Ser His Thr Pro Asp Ala Ser Gly
            20                  25                  30

Leu Gln Glu Leu Ser Glu Ser Thr Tyr Thr Asp Val Leu Asp Gln Thr
        35                  40                  45

Cys Ser Gln Asn Trp Gln Ser Tyr Gly Val His Glu Val Asn Gln Met
50                  55                  60

Lys Arg Leu Thr Gly Pro Gly Leu Ser Lys Gly Pro Glu Pro Arg Ile
65                  70                  75                  80

Ser Val Met Ile Ser Gly Gly Pro Trp Pro Asn Arg Leu Ser Lys Thr
                85                  90                  95

Cys Phe His Tyr Leu Gly Glu Phe Gly Glu Asp Gln Ile Tyr Glu Ala
            100                 105                 110

Tyr Arg Gln Gly Gln Ala Asn Leu Glu Ala Leu Leu Cys Gly Gly Thr
        115                 120                 125

His Gly Pro Cys Ser Gln
    130

<210> SEQ ID NO 11
<211> LENGTH: 884
```

<212> TYPE: DNA
<213> ORGANISM: mouse
<220> FEATURE:
<221> NAME/KEY: misc_feature
<223> OTHER INFORMATION: full length MZB1 coding sequence with 5' and 3'
      UTR

<400> SEQUENCE: 11

| ccaagaagta agttcagagg ccatgagact gcctctgcca ctgttgctac tgttcgggtg | 60 |
| cagggctatc ctggggagcg ccggggatag ggtttccctc tcggcttcgg ctcccacact | 120 |
| ggatgatgaa gagaagtact cggctcatat gccggctcac ctgcgctgcg atgcctgccg | 180 |
| ggctgtggcc ttccagatgg ggcaacgtct ggcgaaagca gaggctaaat ctcacactcc | 240 |
| agacgccagt ggattgcagg agctgagtga atccacgtac acagatgtcc tggaccagac | 300 |
| ctgctctcag aactggcagt cctatggagt tcatgaagtg aaccagatga agcgtctcac | 360 |
| gggcccagga cttagcaagg ggccagagcc aagaatcagc gtgatgattt ctgggggtcc | 420 |
| ctggcccaat aggctctcca agacgtgttt ccactacctg ggtgagtttg gagaggacca | 480 |
| gatctatgaa gcctaccgcc aaggccaagc gaatctggag gcgctgctct gtggggggcac | 540 |
| ccatgggccc tgctcacagg agatcctggc ccagagagaa gagctttagt ccaacctgct | 600 |
| gcacttctgg atcttctcta attttattat tattaatggc tgattagagg caggctctca | 660 |
| tcatgtaggc caggctggct taaacttgtc atcctgctca gcctcgaaag tgctgcattt | 720 |
| aagtcctgag ccttttttgtg cttgaccctc ctatataatt ttttcaactg tggtggtggg | 780 |
| gaggggacag ggaagcctga ctctagctgt caatcttctc cctccacctc tcgatggggt | 840 |
| actgggactg aggctgcctt tctactttca aataaagctt tgaa | 884 |

<210> SEQ ID NO 12
<211> LENGTH: 586
<212> TYPE: DNA
<213> ORGANISM: mouse
<220> FEATURE:
<221> NAME/KEY: misc_feature
<223> OTHER INFORMATION: full length MZB1 coding sequence with 5' UTR

<400> SEQUENCE: 12

| ccaagaagta agttcagagg ccatgagact gcctctgcca ctgttgctac tgttcgggtg | 60 |
| cagggctatc ctggggagcg ccggggatag ggtttccctc tcggcttcgg ctcccacact | 120 |
| ggatgatgaa gagaagtact cggctcatat gccggctcac ctgcgctgcg atgcctgccg | 180 |
| ggctgtggcc ttccagatgg ggcaacgtct ggcgaaagca gaggctaaat ctcacactcc | 240 |
| agacgccagt ggattgcagg agctgagtga atccacgtac acagatgtcc tggaccagac | 300 |
| ctgctctcag aactggcagt cctatggagt tcatgaagtg aaccagatga agcgtctcac | 360 |
| gggcccagga cttagcaagg ggccagagcc aagaatcagc gtgatgattt ctgggggtcc | 420 |
| ctggcccaat aggctctcca agacgtgttt ccactacctg ggtgagtttg gagaggacca | 480 |
| gatctatgaa gcctaccgcc aaggccaagc gaatctggag gcgctgctct gtggggggcac | 540 |
| ccatgggccc tgctcacagg agatcctggc ccagagagaa gagctt | 586 |

<210> SEQ ID NO 13
<211> LENGTH: 862
<212> TYPE: DNA
<213> ORGANISM: mouse
<220> FEATURE:
<221> NAME/KEY: misc_feature
<223> OTHER INFORMATION: full length MZB1 coding sequence with 3' UTR -continued

<400> SEQUENCE: 13

```
atgagactgc ctctgccact gttgctactg ttcgggtgca gggctatcct ggggagcgcc      60
ggggataggg tttccctctc ggcttcggct cccacactgg atgatgaaga gaagtactcg     120
gctcatatgc cggctcacct cgctgcgat gcctgccggg ctgtggcctt ccagatgggg      180
caacgtctgg cgaaagcaga ggctaaatct cacactccag acgccagtgg attgcaggag     240
ctgagtgaat ccacgtacac agatgtcctg gaccagacct gctctcagaa ctggcagtcc     300
tatggagttc atgaagtgaa ccagatgaag cgtctcacgg gcccaggact tagcaagggg     360
ccagagccaa gaatcagcgt gatgatttct gggggtccct ggcccaatag gctctccaag     420
acgtgtttcc actacctggg tgagtttgga gaggaccaga tctatgaagc ctaccgccaa     480
ggccaagcga atctggaggc gctgctctgt gggggcaccc atgggccctg ctcacaggag     540
atcctggccc agagagaaga gctttagtcc aacctgctgc acttctggat cttctctaat     600
tttattatta ttaatggctg attagaggca ggctctcatc atgtaggcca ggctggctta     660
aacttgtcat cctgctcagc ctcgaaagtg ctgcatttaa gtcctgagcc ttttttgtgct    720
tgaccctcct atataatttt tcaactgtg gtggtgggga ggggacaggg aagcctgact      780
ctagctgtca atcttctccc tccacctctc gatggggtac tgggactgag gctgccttc     840
tactttcaaa taaagctttg aa                                              862
```

<210> SEQ ID NO 14
<211> LENGTH: 19
<212> TYPE: DNA
<213> ORGANISM: mouse
<220> FEATURE:
<221> NAME/KEY: misc_feature
<223> OTHER INFORMATION: RNAi target sequence

<400> SEQUENCE: 14

```
gcgaaagcag aggctaaat                                                   19
```

<210> SEQ ID NO 15
<211> LENGTH: 19
<212> TYPE: DNA
<213> ORGANISM: mouse
<220> FEATURE:
<221> NAME/KEY: misc_feature
<223> OTHER INFORMATION: RNAi target sequence

<400> SEQUENCE: 15

```
gcagtcctat ggagttcat                                                   19
```

<210> SEQ ID NO 16
<211> LENGTH: 19
<212> TYPE: DNA
<213> ORGANISM: mouse
<220> FEATURE:
<221> NAME/KEY: misc_feature
<223> OTHER INFORMATION: RNAi target sequence

<400> SEQUENCE: 16

```
ccagatctat gaagcctac                                                   19
```

<210> SEQ ID NO 17
<211> LENGTH: 19
<212> TYPE: DNA
<213> ORGANISM: mouse
<220> FEATURE:
<221> NAME/KEY: misc_feature
<223> OTHER INFORMATION: RNAi target sequence

<400> SEQUENCE: 17
ctgccactgt tgctactgt                                                    19

<210> SEQ ID NO 18
<211> LENGTH: 47
<212> TYPE: RNA
<213> ORGANISM: mouse
<220> FEATURE:
<221> NAME/KEY: misc_feature
<223> OTHER INFORMATION: MZB1 specific shRNA

<400> SEQUENCE: 18
gcgaaagcag aggcuaaauu ucaagagaau uuagccucug cuuucgc                     47

<210> SEQ ID NO 19
<211> LENGTH: 47
<212> TYPE: RNA
<213> ORGANISM: mouse
<220> FEATURE:
<221> NAME/KEY: misc_feature
<223> OTHER INFORMATION: MZB1 specific shRNA

<400> SEQUENCE: 19
gcagaccuau ggaguucauu ucaagagaau gaacuccaua ggacugc                     47

<210> SEQ ID NO 20
<211> LENGTH: 46
<212> TYPE: RNA
<213> ORGANISM: mouse
<220> FEATURE:
<221> NAME/KEY: misc_feature
<223> OTHER INFORMATION: MZB1 specific shRNA

<400> SEQUENCE: 20
ccagaucuau gaagccuacu caagagagua ggcuucauag aucugg                      46

<210> SEQ ID NO 21
<211> LENGTH: 47
<212> TYPE: RNA
<213> ORGANISM: mouse
<220> FEATURE:
<221> NAME/KEY: misc_feature
<223> OTHER INFORMATION: MZB1 specific shRNA

<400> SEQUENCE: 21
cugccacugu ugcuacuguu ucaagagaac aguagcaaca guggcag                     47

<210> SEQ ID NO 22
<211> LENGTH: 19
<212> TYPE: DNA
<213> ORGANISM: mouse
<220> FEATURE:
<221> NAME/KEY: misc_feature
<223> OTHER INFORMATION: RNAi target sequence

<400> SEQUENCE: 22
gcaaaggcgg aagcgaagt                                                    19

MZB1, A NOVEL B CELL FACTOR, AND USES THEREOF

CROSS-REFERENCE TO RELATED APPLICATIONS

This application is a divisional application of copending U.S. patent application Ser. No. 13/740,772, filed Jan. 14, 2013, which is a continuation of U.S. patent application Ser. No. 12/935,406, filed on Feb. 9, 2011, now abandoned, which is the U.S. National Phase of International Patent Application No. PCT/EP2009/002349, filed on Mar. 31, 2009, which claims priority to European Patent Application No. 08 006 376.1, filed on Mar. 31, 2008.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,966 bytes ASCII (Text) file named "730706_ST25.txt," created Aug. 29, 2017.

FIELD OF THE INVENTION

The present invention relates to the field of immunology, in particular, the field of B cell biology. The present invention provides a novel B cell factor, MZB1, which is involved in the regulation of B cell receptor (BCR)-mediated signaling and antibody production. The present invention further provides agents which modulate the expression and/or the activity of MZB1 and the use of these agents for research and therapeutic purposes.

BACKGROUND OF THE INVENTION

The vertebrate immune system protects the host from foreign pathogens such as virus, bacteria, parasite and fungus as well as senesced, damaged or diseased host cells. The host defense against foreign pathogens can be divided into three phases: innate immunity, "natural memory" and adaptive immunity.

Innate immunity is the first line of defense against foreign pathogens, which is active within minutes or hours after exposure to pathogen. The innate immunity is not antigen-specific; it is carried out by immune cells such as macrophages, mast cells, granulocytes (basophils, eosinophils, neutrophils), natural killer cells, and γδT cells, which recognize features that are common to many pathogens rather than specific antigens.

In contrast, the adaptive immunity is antigen-specific; it is carried out by antigen-specific T cells and B cells, in particular, follicular (FO) B cells, and takes days to two weeks to develop. T cells and FO B cells express antigen-specific receptors, T cell receptor (TCR) and B cell receptor (BCR), respectively, which are encoded by genes rearranged from the germline conformation.

In addition to being antigen-specific, the adaptive immunity differs from the innate immunity in its capability of generating immunological memory. The memory B and T cells are capable of launching a more rapid and more robust response against foreign antigens upon re-exposure to the same antigens.

The natural memory bridges the temporal gap between the innate immune response and the adaptive immune response; it is carried out by several components of the B and T cell lineages but does not generate lasting protective immunity for longer than a few days.

An important part of the natural memory immune response is the production of natural antibodies which have high cross-reactivity but low binding affinity against both microbial agents and some self antigens (Baumgarth et al., 1999; Baumgarth et al., 2000; Boes et al., 1998; Ochsenbein et al., 1999). The natural antibodies are encoded by rearranged antibody genes that have not undergone somatic mutation and are produced by marginal zone (MZ) B cells and peritoneal B1 cells. MZ B cells play a key role in the early response to pathogens in the bloodstream, whereas B1 cells in the pleural and peritoneal cavity play a key role in the response to pathogens introduced in the mucosal surfaces (see review by Lopes-Carvalho T and Kearney J F, 2004). Recent studies have suggested that B1 B cells and MZ B cells are also a source of auto-antibodies, Even though B1 B cells and MZ B cells play a key role in natural memory immune response against foreign pathogens and are likely involved in autoimmune diseases involving auto-antibodies, the development, homeostasis and activation of these B cell subsets are only beginning to be elucidated (see reviews by Martin F and Kearney J F, 2000 and Srivastava B et al., 2005). Therefore, there remains a need in the art to better understand the biology of MZ and B1 B cells, in particular, their activation and the regulation of natural antibody production. Furthermore, there remains a need in the art to develop tools which allow for the modulation of the activities of MZ and B1 B cells, in particular, the production of natural antibodies, more particularly, the production of auto-reactive antibodies.

SUMMARY OF THE INVENTION

The present invention also provides an isolated polypeptide comprising an amino acid sequence selected from the group consisting of:

(a) the amino acid sequence as set forth in SEQ ID NO:2 or 4, (b) an amino acid sequence encoded by the nucleotide sequence set forth in SEQ ID NO:1 or 3, (c) an amino acid sequence of (a) or (b) further comprising an amino-terminal methionine, (d) an amino acid sequence which is an ortholog any of (a)-(c), optionally further comprising an amino-terminal methionine, (e) an amino acid sequence which is an allelic variant or a splice variant of any of (a)-(d), optionally further comprising an amino-terminal methionine, (f) an amino acid sequence which is at least 72% identical to any of (a)-(e) over its entire length, optionally further comprising an amino-terminal methionine, (g) an amino acid sequence as set forth in SEQ ID NO:2 or 4 with at least one amino acid modification selected from substitution, insertion, deletion, amino terminal truncation, carboxyl terminal truncation, or any combination thereof, optionally further comprising an amino-terminal methionine, (h) an amino acid sequence comprising at least 10 consecutive amino acids of any of (a)-(g), optionally further comprising an amino-terminal methionine, (j) an amino acid sequence encoded by the isolated nucleic acid of any of items 1(a)-(i), optionally further comprising an amino-terminal methionine, and (k) an amino acid sequence comprising any of (a)-(j) fused to a heterologous sequence, wherein (d)-(f) has at least one of the biological activities of the polypeptide having the amino acid sequence of any of (a)-(c).

The present invention further provides a vector comprising an isolated nucleic acid of the present invention operably linked to a transcriptional regulatory sequence.

The present invention additionally provides a host cell or a host organism comprising an isolated nucleic acid or a vector of the present invention.

The present invention provides an antibody or an antigen-binding fragment thereof which specifically binds a polypeptide of the present invention and a hybridoma or a host cell producing said antibody.

The present invention also provides a process for producing a polypeptide of the present invention, comprising culturing the host cell of the present invention under suitable conditions to express the polypeptide, and optionally isolating the polypeptide from the culture, wherein the expression vector contained in the host cell comprises a nucleic acid of any of (a)-(i) described above The present invention provides an inhibitor of the expression or at least one of the biological activities of a polypeptide of the present invention which is biologically active.

The present invention also provides an activator or enhancer of the expression or at least one of the biological activities of the polypeptide of the present invention which is biologically active.

The present invention further provides a pharmaceutical composition comprising an inhibitor or an activator or enhancer of the present invention.

The present invention provides the use of an inhibitor of the present invention for treating an autoimmune disease. Thus, the present invention provides remedies for autoimmune diseases, in particular, means, methods and uses for preventing and/or treating autoimmune diseases.

The present invention also provides the use of an activator or enhancer of the present invention for treating an immunodeficiency. Thus, the present invention provides remedies for immunodeficiency, in particular, means, methods and uses for preventing and/or treating immunodeficiency.

The present invention additionally provides an in vitro method for enhancing the antibody production in a cell, comprising the step of contacting the cell with an activator or enhancer of the present invention, wherein the cell is capable of producing an antibody.

(A) MZB1 expression is restricted to B cell tissues. Poly-A$^+$ RNA (2 μg) from adult mice and 5 μg of cytoplasmic RNA from the pre-B cell line PD36 were utilized for an RNA analysis to detect MZB1 specific transcripts. As loading control and control for B cell contamination, probes hybridizing the constant region of Igκ and GADPH were utilized.

(B) MZB1 expression in different B cell populations. Western blot was performed on 30 μg of total protein extract from different FACS-sorted B cell populations.

Figure 2:
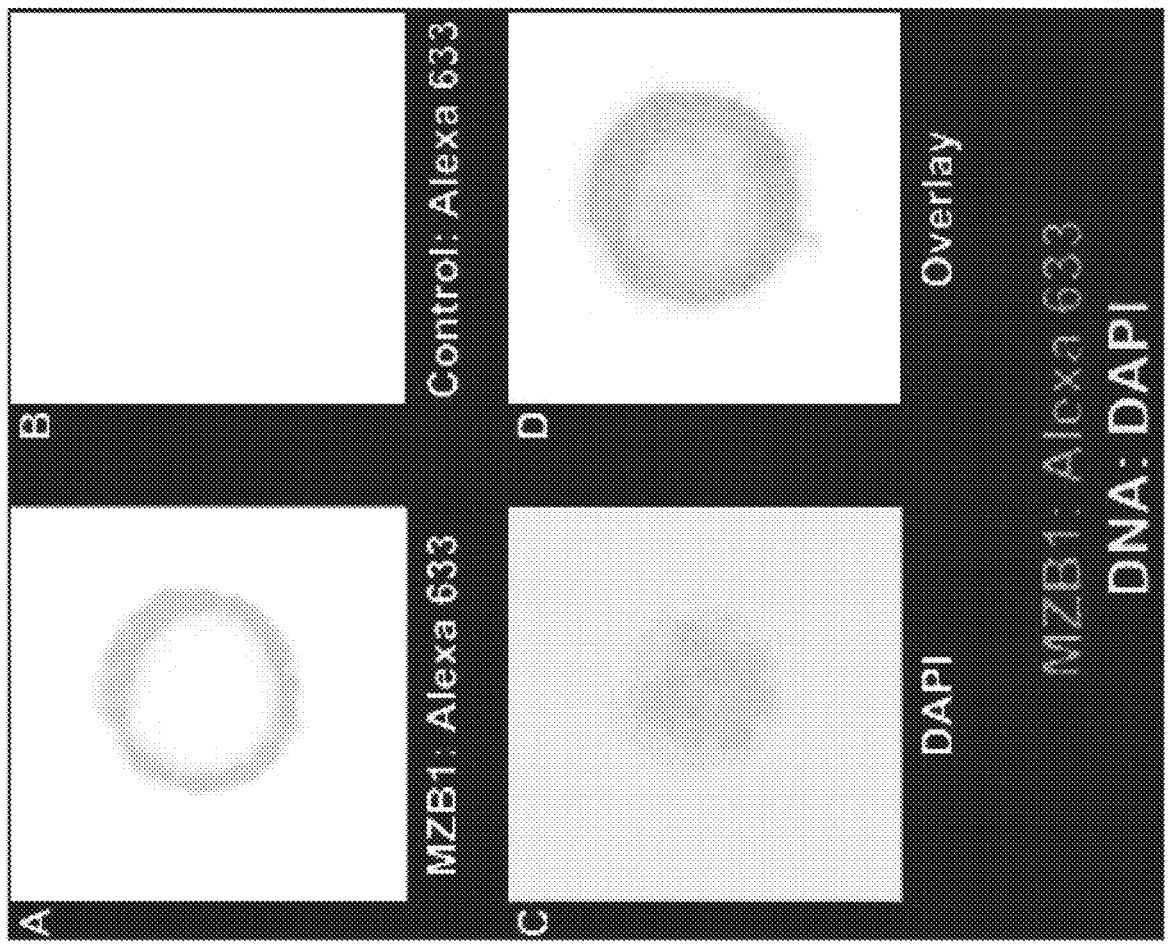

FIG. 2: Indirect immunofluorescence (IF) on FACS-sorted marginal zone (MZ) B cells MZB1 staining (A. D): control (B): and DAPI staining (C). The isolated cells were fixed with 4% paraformaldehyde and used for IF experiments with rat anti-MZB1 followed by anti-rat Alexa647 antibodies.

Figure 3:
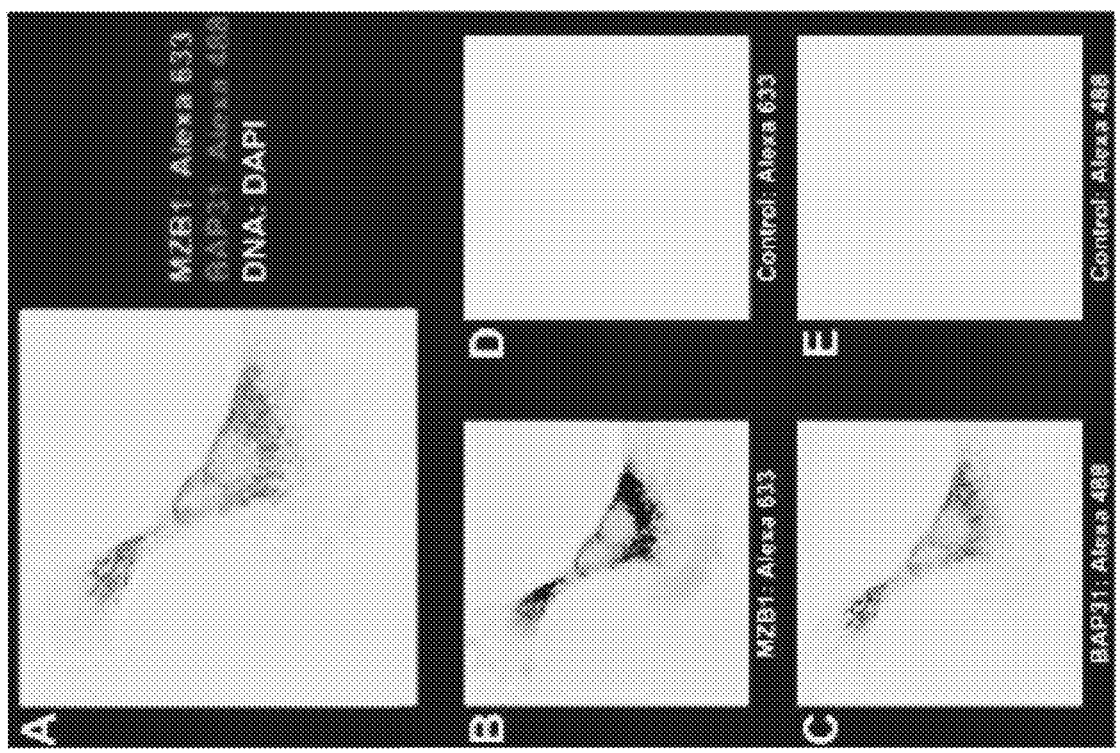

FIG. 3: Indirect immunofluorescence (IF) on NIH 3T3 cells stably expressing FLAG-MZB1: MZB1 staining (A. B): controls (D. E): and BAP31 staining (C). The cells were fixed with 4% paraformaldehyde and used for IF-experiments with rat α-MZB1 followed by α-rat Alexa633 (red) and/or α-BAP31 followed by α-mouse Alexa488 (green) antibodies.

Figure 4:
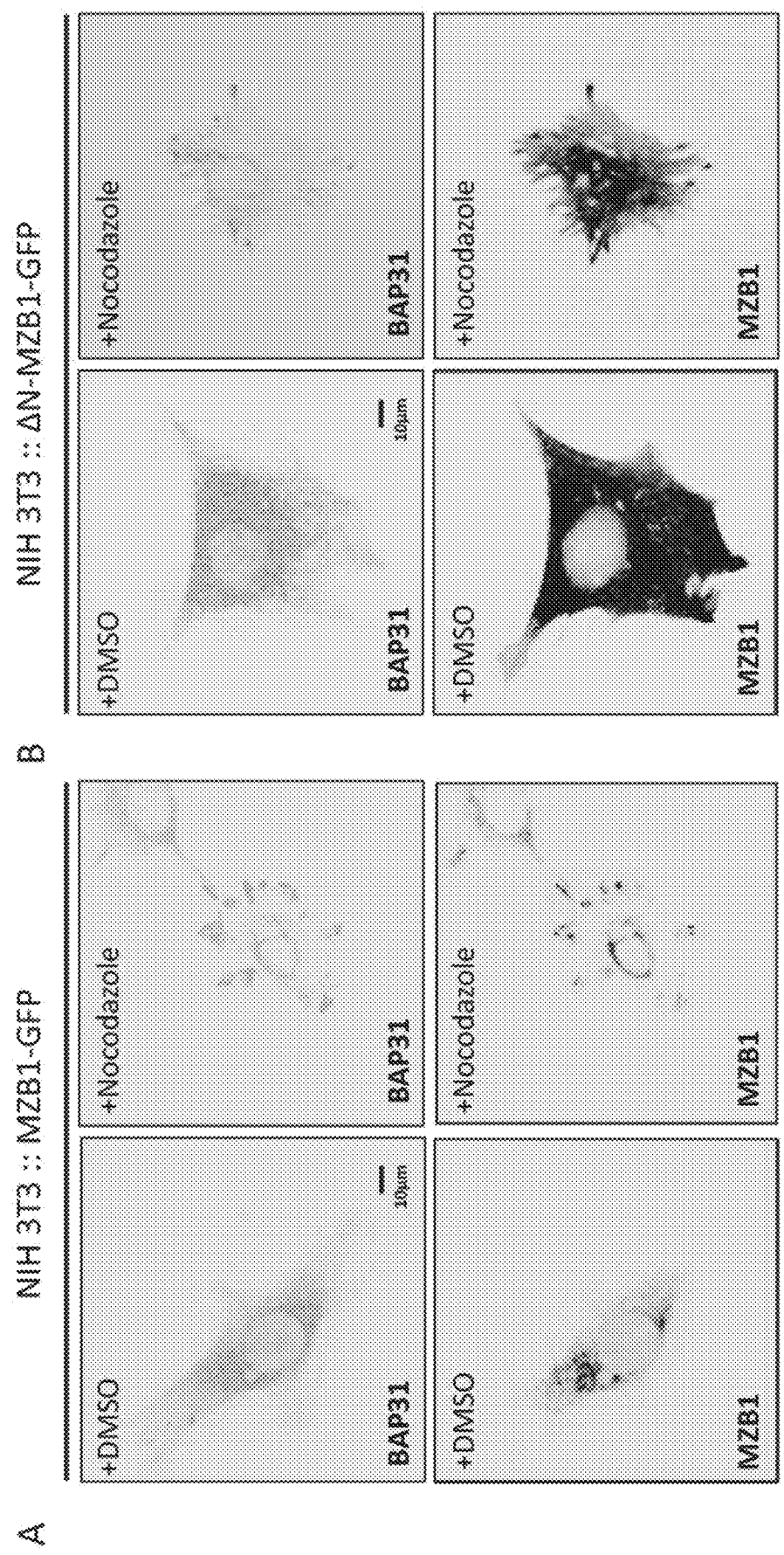

FIG. 4: Indirect immunofluorescence (IF) on NIH3T3 cells stably transfected with either MZB1-GFP (A) or AN-MZB1-GFP (B). NIH3T3 fibroblastic cells were stably transfected with either MZB1-GFP (MZB1-GFP fusion protein) (A) or AN-MZB1-GFP (MZB1-GFP fusion protein lacking the N-terminal signal peptide of MZB1) (B). Cells were treated for 6 h with DMSO (control) or 1 μg/ml nocodazole. The treated cells were fixed with 4% paraformaldehyde and used for IF-experiments with rat aMZB1 followed by arat Alexa647 antibodies (green) and rabbit aBAP31 followed by arabbit Alexa568 antibodies (red). BAP31 was used as a marker for ER membranes.

Figure 5:
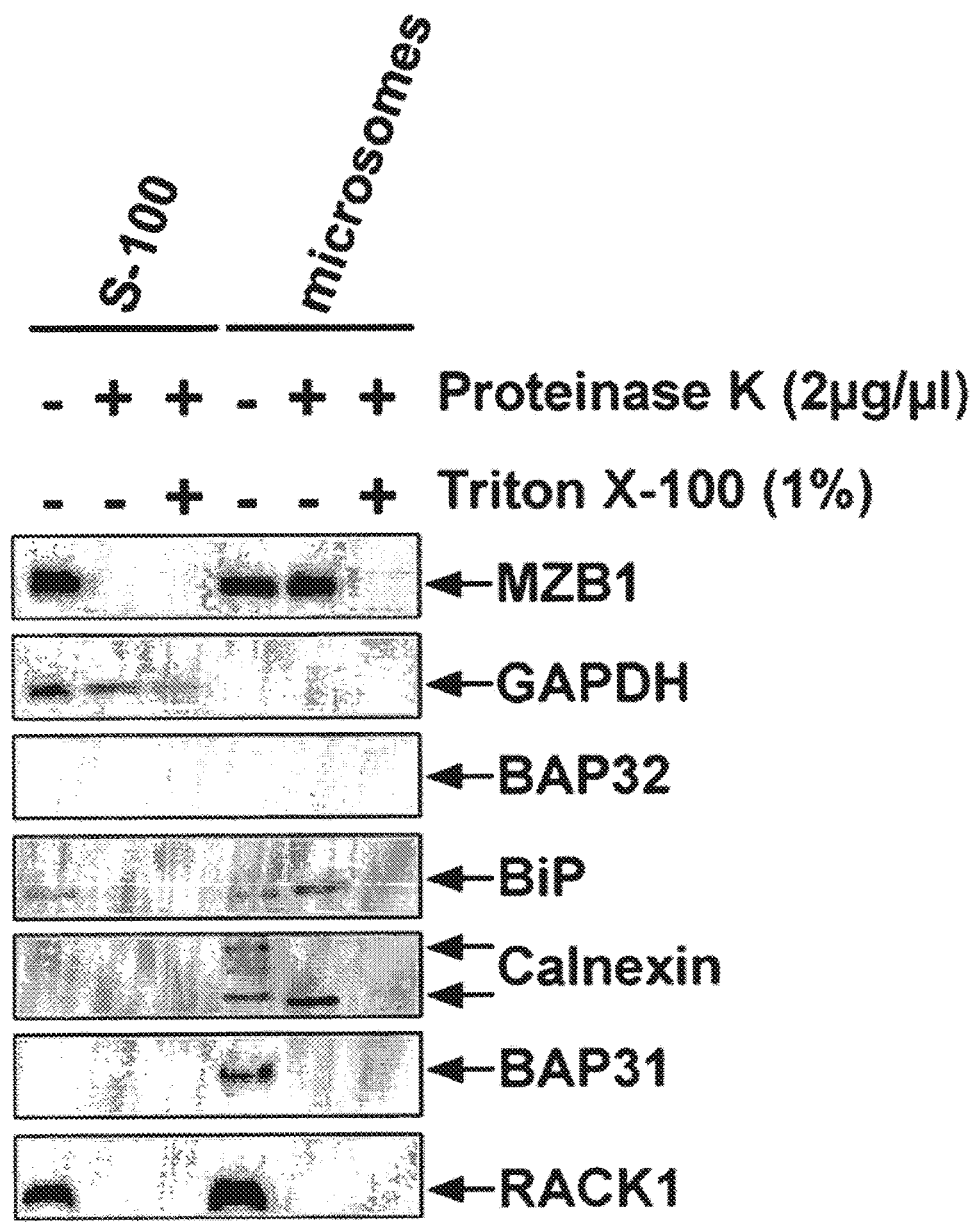

FIG. 5: Preparation of endoplasmatic reticulum (ER) vesicles and proteinase K digestion. K46 cells were resuspended in a hypertonic buffer containing 250 mM sucrose, and homogenized by passing through a 22 gauge needle 15 times and centrifuged at 3000 g for 10 min. The supernatant was centrifuged at 20,000 g for 15 min. and the resulting pellet, containing mitochondrial membranes, was discarded. The resulting supernatant (S-20) was centrifuged at 100,000 g for 1 h. The pellet contained sealed cytosolic-side-out ER vesicles (microsomes), which were resuspended in the hypertonic lysis buffer plus 100 mM NaCl, Aliquots of the preparation (~10 μg of protein), S-100 and microsomal fraction, were treated with 2 μg/μl proteinase K in the presence or absence of 1% Triton X-100 in a total volume of 12 μl for 30 min. on ice. The reaction was stopped by adding PMSF at a final concentration of 30 mM and samples were subjected to TCA-precipitation followed by SDS-PAGE and immunoblot analysis using antibodies specific for MZB1. As a control for the ER vesicle preparation, additional immunoblot analysis using antibodies specific for the mitochondrial transmembrane protein BAP32, the ER transmembrane proteins BAP31 and Calnexin, the luminal ER protein BiP, the ER membrane-associated, cytosolic protein RACK1 as well as the cytosolic protein GAPDH were performed.

Figure 6:
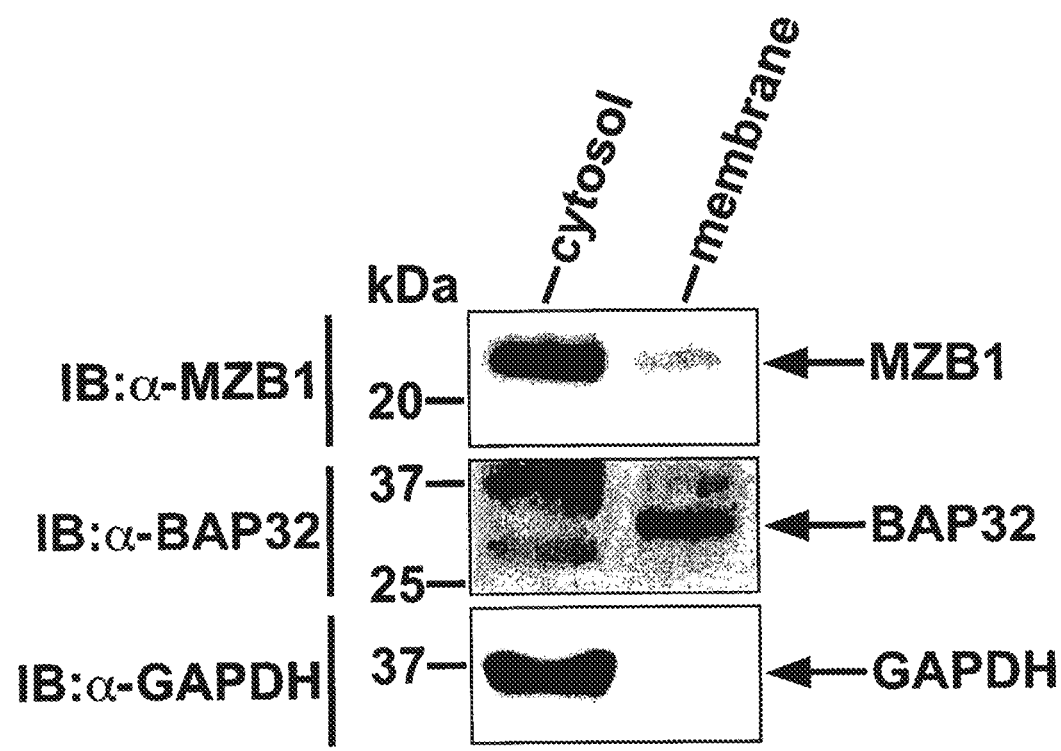

FIG. 6: Immunoblot analysis with antibodies specific for MZB1, BAP32 and GAPDH was performed on 10 μg of cytosolic and membrane fractions extracted from K46 mature B cells.

Figure 7:
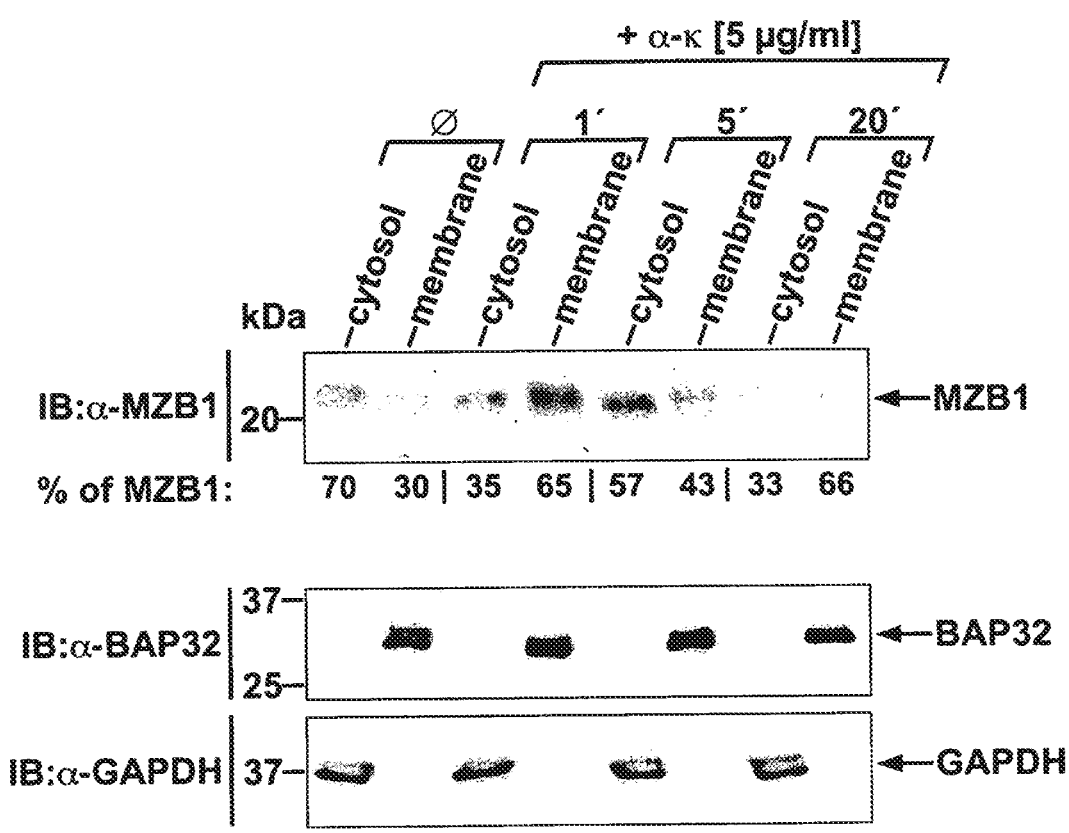

FIG. 7: Immunoblot analysis with antibodies specific for MZB1, BAP32 and GAPDH was performed on 10 μg of cytosolic and membrane fractions extracted from non-stimulated and stimulated K46 mature B cells. Cells were BCR stimulated with 5 μg/ml α-kappa antibody for the indicated time spans.

Figure 8:
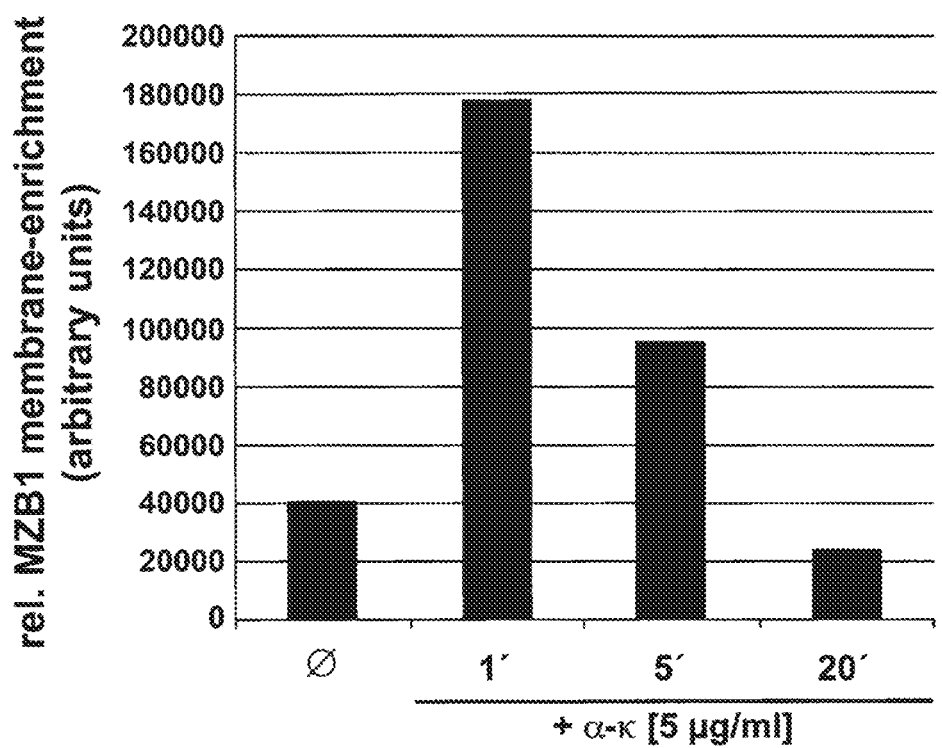

FIG. 8: Recruitment of MZB1 to the cell membrane following BCR stimulation of K46 B cells. Densitometric analysis of MZB1-specific immunoblot signals depicted in FIG. 7.

Figure 9:
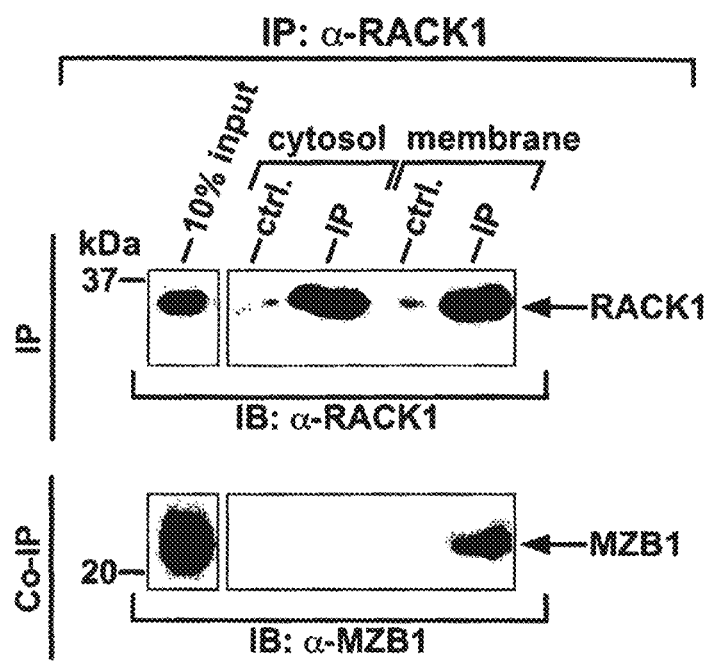
Figure 9:
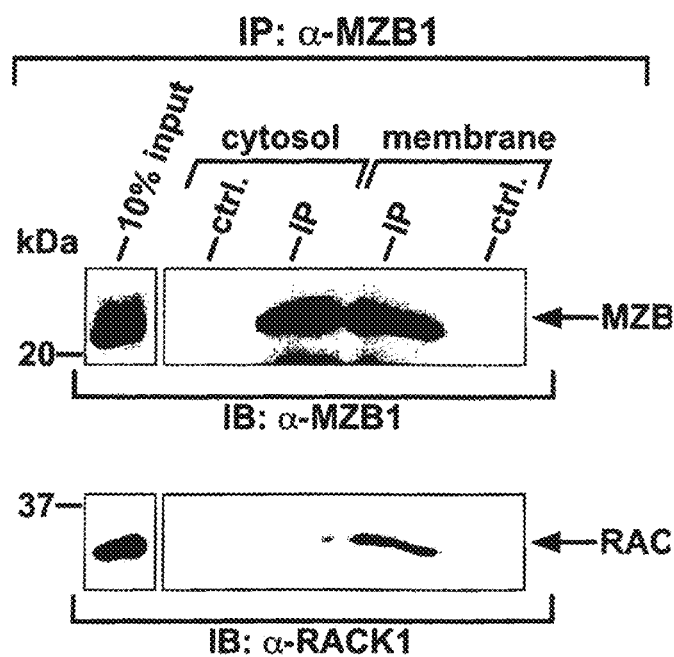

FIG. 9: Identification of the receptor for activated C kinase 1 (RACK1) as an MZB1 interaction partner in the membrane fraction of K46 B cells.

(A) Anti-RACK1 Immunoprecipitation (IP). Membrane and cytosol fractions of K46 B cells were prepared. Immunoprecipitation (IP) was performed using anti-RACK1 and/or Protein L beads (ctrl.) utilizing the cytosolic or membrane fractions. The presence of MZB1 and RACK1 was monitored by immunoblotting.

(B) Anti-MZB1 Immunoprecipitation (IP). Membrane and cytosol fractions of K46 B cells were prepared. Immunoprecipitation (IP) was performed using anti-MZB1 sepharose beads and the cytosolic or membrane fractions. The presence of MZB1 and RACK1 was monitored by immunoblotting.

Figure 10:
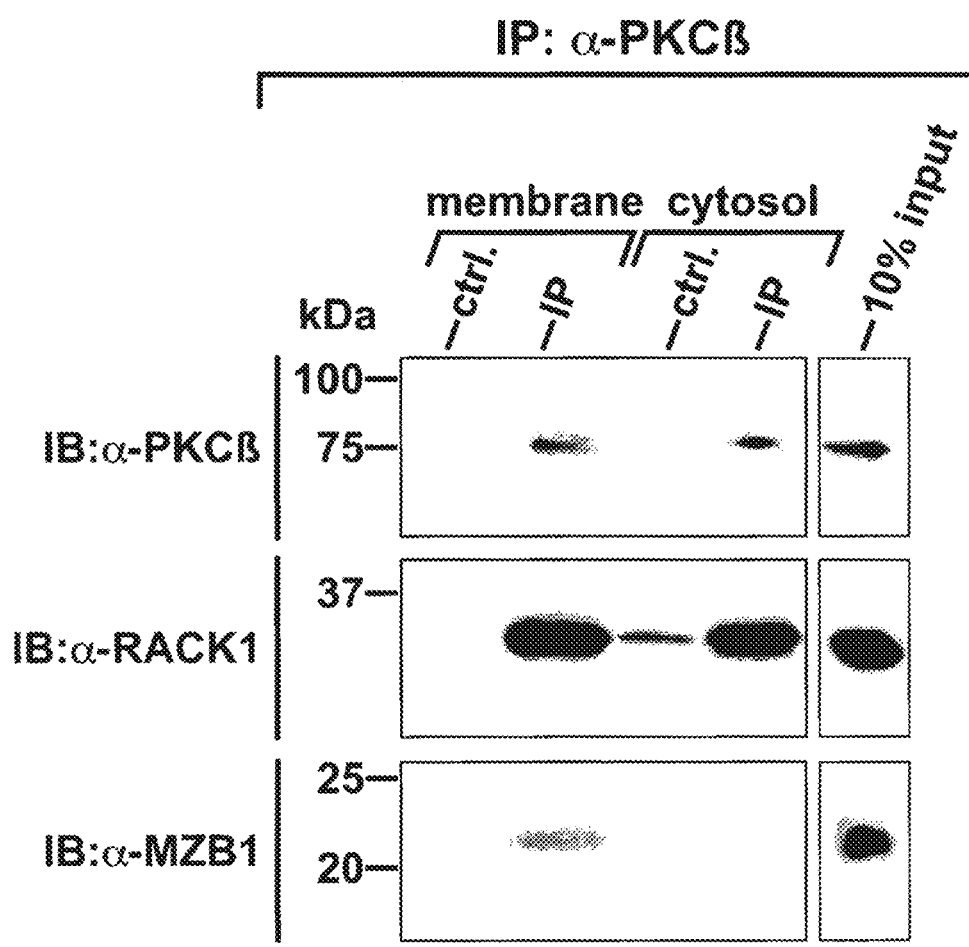

FIG. 10: Interaction of RACK1, PKCβ and MZB1 in the membrane fraction of K46 B cells. Anti-PKCβ Immunoprecipitation (IP). Membrane and cytosol fractions of K46 B cells were prepared. Immunoprecipitation (IP) was performed using anti-PKCβ and Protein G beads utilizing the cytosolic or membrane fractions. Protein G beads alone served as the control. The presence of MZB1, PKCβ and RACK1 was monitored by immunoblotting.

Figure 11:
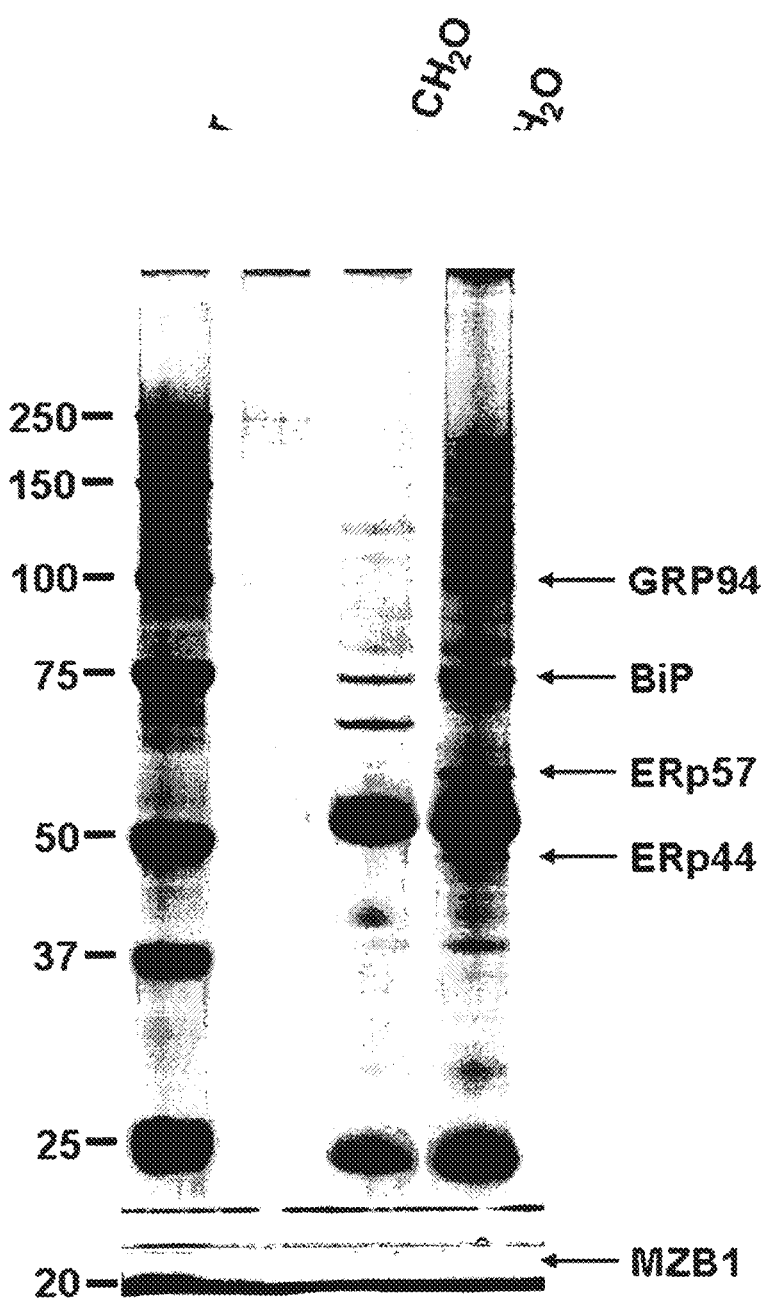

FIG. 11: MZB1 complex purification. Approximately 1.01 of K46 mature B cells were cultured until reaching the exponential growth phase, harvested and in vivo formaldehyde crosslinking was performed by adding 1% formaldehyde (final concentration) directly to the K46 cell culture. Cells were incubated for 10 min at 37° C. and 5% $CO_2$ and the crosslinking reaction was quenched by addition of 2.5M glycine with a final concentration of 125 mM. After crosslinking, cells were collected, washed with ice-cold PBS and frozen at −80° C. prior to lysis. After cell extract preparation, using an SDS containing hypotonic lysis buffer and extensive sonication, MZB1 was immunoprecipitated using an MZB1-specific antibody, directly coupled to 4B-sepharose beads. As controls, MZB1 was immunoprecipitated from un-crosslinked K46 cell extract, and, in addition, 4B beads were incubated with crosslinked K46 cell extract. The immunoprecipitated proteins were eluted with sample buffer and separated on a 4%-12% gradient SDS-PAGE. The gel was silver stained. The marked bands (arrow) were cut out and prepared for mass spectrometry analysis.

Figure 12:
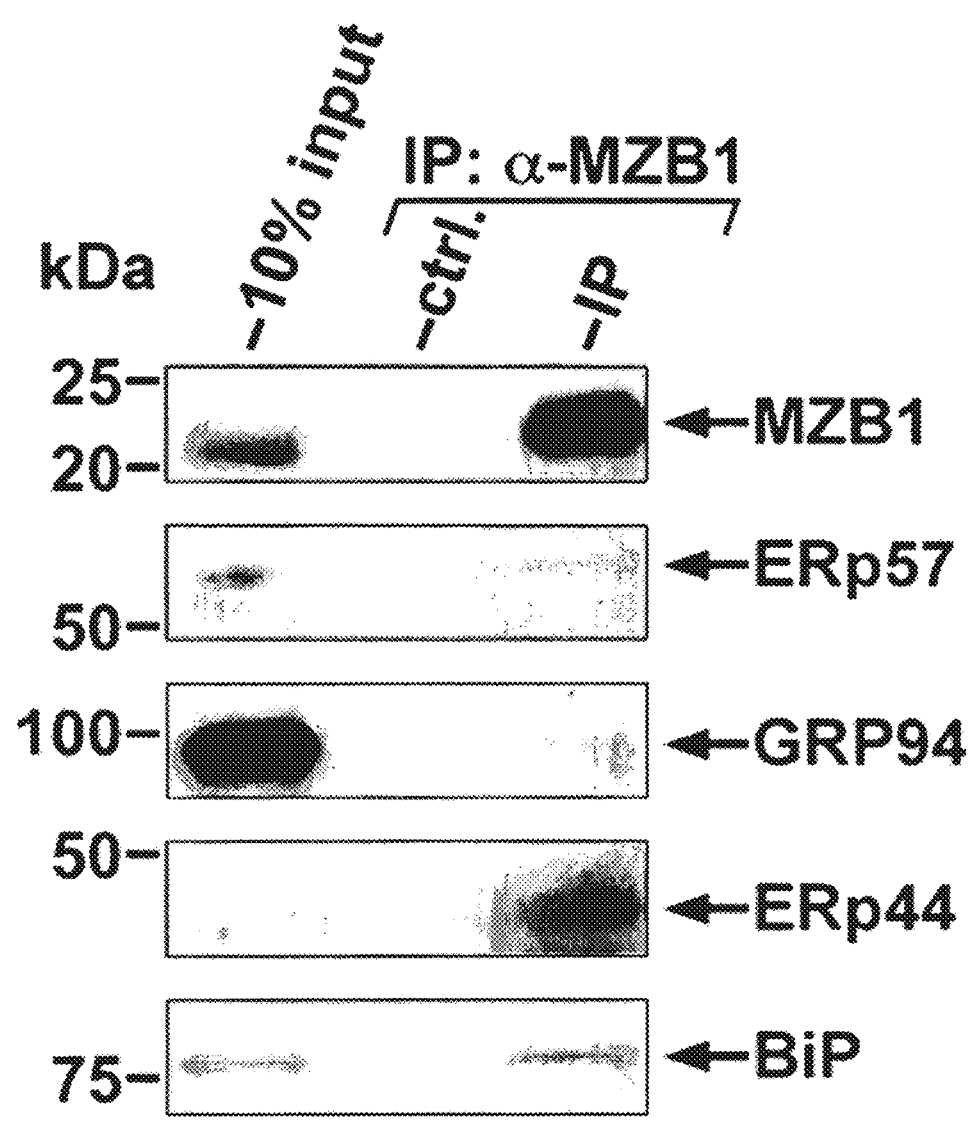

FIG. 12: Verification of ERp57, GRP94 (Endoplasmin), ERp44 and BiP as potential MZB1 interaction partners. Anti-MZB1 Immunoprecipitation (IP). Cellular extracts of K46 B cells were prepared. Immunoprecipitation (IP) was performed using anti-MZB1 sepharose beads and anti-EBNA sepharose as control. The presence of MZB1, ERp57, GRP94, ERp44 and BiP was monitored by immunoblotting.

Figure 13:
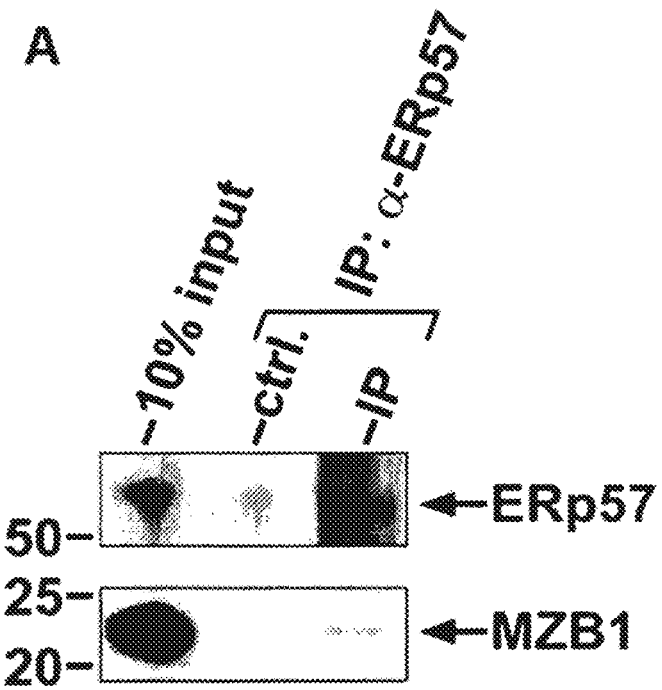
Figure 13:
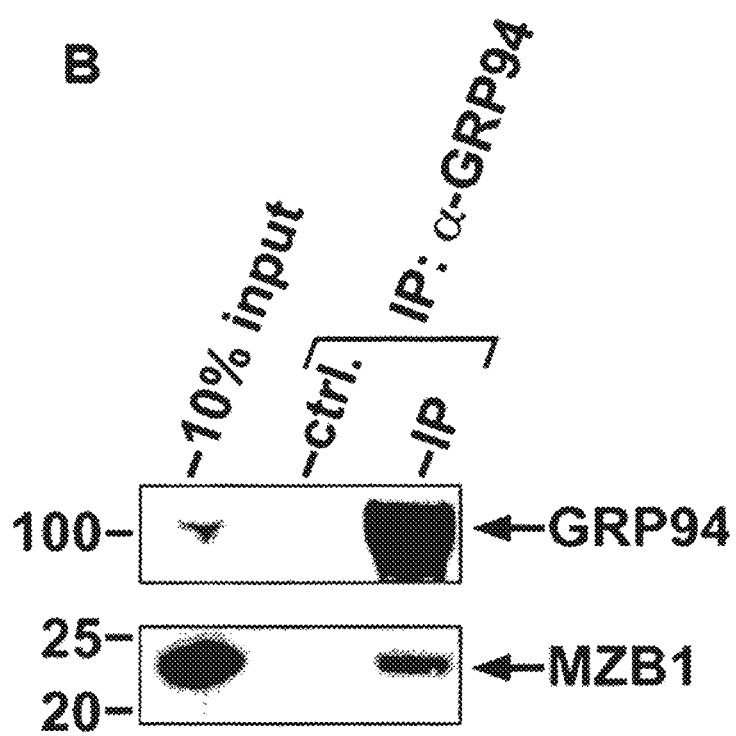

FIG. 13: Verification of ERp57 and GRP94 (Endoplasmin) as potential MZB1 interaction partners.

(A) Anti-ERp57 Immunoprecipitation (IP). Cellular extracts of K46 B cells were prepared. Immunoprecipitation (IP) was performed using anti-ERp57 antibodies in combination with Protein G beads or Protein G beads alone (control). The presence of MZB1 and ERp57 was monitored by immunoblotting.

(B) Anti-GRP94 Immunoprecipitation (IP). Cellular extracts of K46 B cells were prepared. Immunoprecipitation (IP) was performed using anti-GRP94 antibodies in combination with Protein G beads or Protein G beads alone (control). The presence of MZB1 and GRP94 was monitored by immunoblotting.

Figure 14:
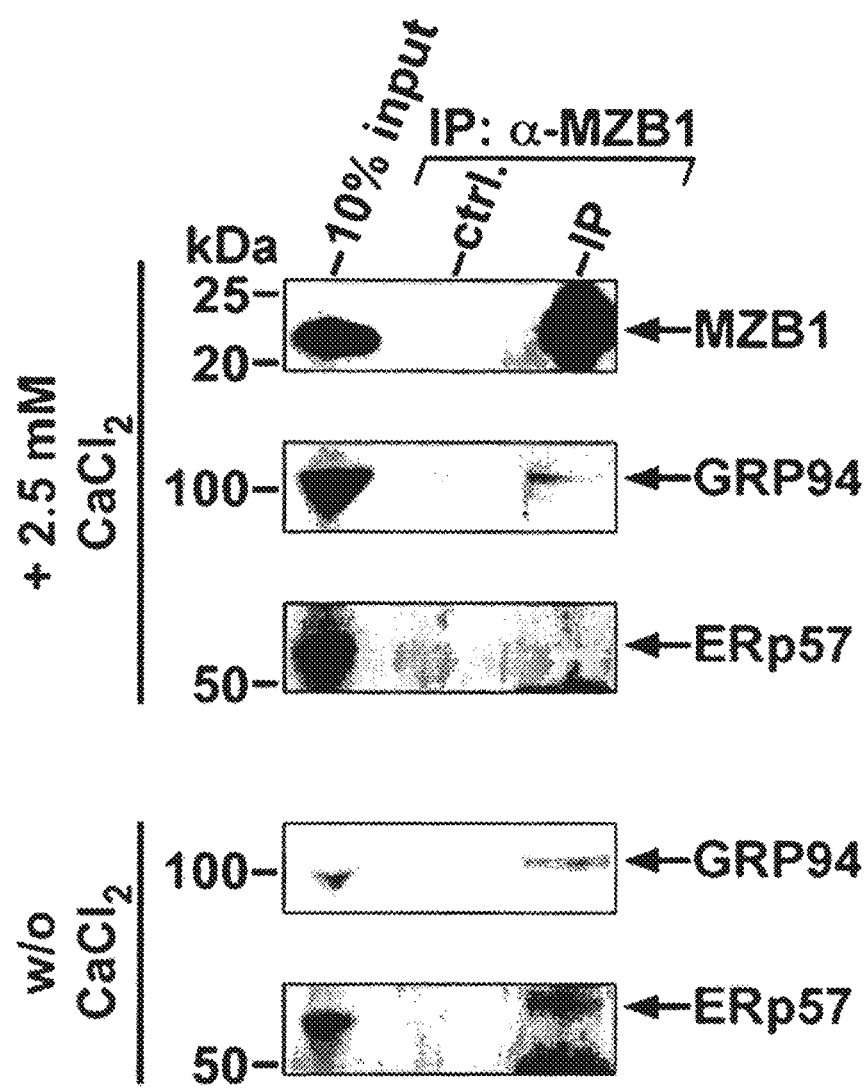

FIG. 14: MZB1 interacts with ERp57, but not GRP94 (Endoplasmin), in a $Ca^{2+}$-dependent fashion. Anti-MZB1 Immunoprecipitation (IP). Cellular extracts of K46 B cells were prepared in the presence or the absence of 2.5 mM $Ca^{2+}$. Immunoprecipitation (IP) was performed using anti-MZB1 sepharose beads and anti-EBNA sepharose as control. The presence of MZB1, ERp57, GRP94, ERp44 and BiP was monitored by immunoblotting.

Figure 15:
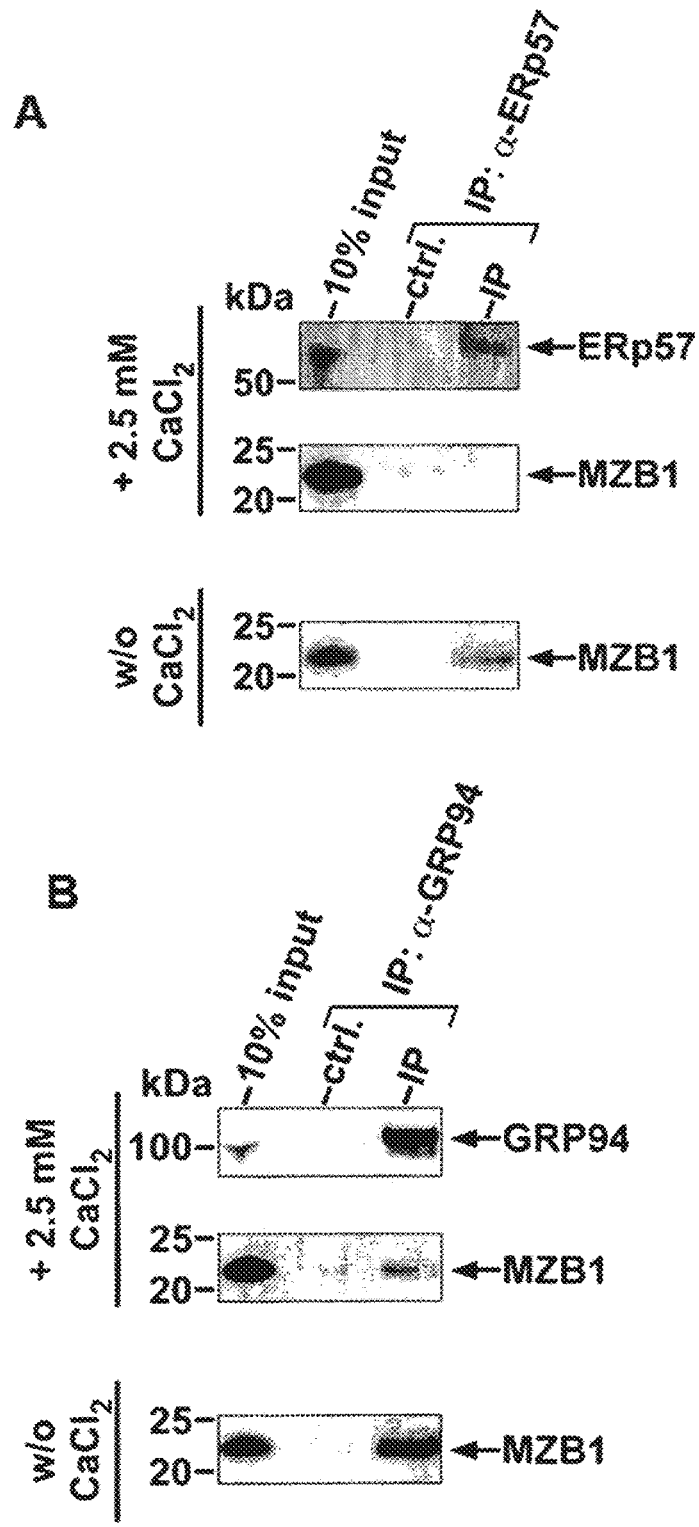

FIG. 15: MZB1 interacts with ERp57, but not GRP94 (Endoplasmin), in a $Ca^{2+}$-dependent fashion.

(A) Anti-ERp57 Immunoprecipitation (IP). Cellular extracts of K46 B cells were prepared in the presence or the absence of 2.5 mM $Ca^{2+}$. Immunoprecipitation (IP) was performed using anti-ERp57 antibodies in combination with Protein G beads or Protein G beads alone (control). The presence of MZB1 and ERp57 was monitored by immunoblotting.

(B) Anti-GRP94 Immunoprecipitation (IP). Cellular extracts of K46 B cells were prepared in the presence or the absence of 2.5 mM $Ca^{2+}$. Immunoprecipitation (IP) was performed using anti-GRP94 antibodies in combination with Protein G beads or Protein G beads alone (control). The presence of MZB1 and GRP94 was monitored by immunoblotting.

Figure 16:
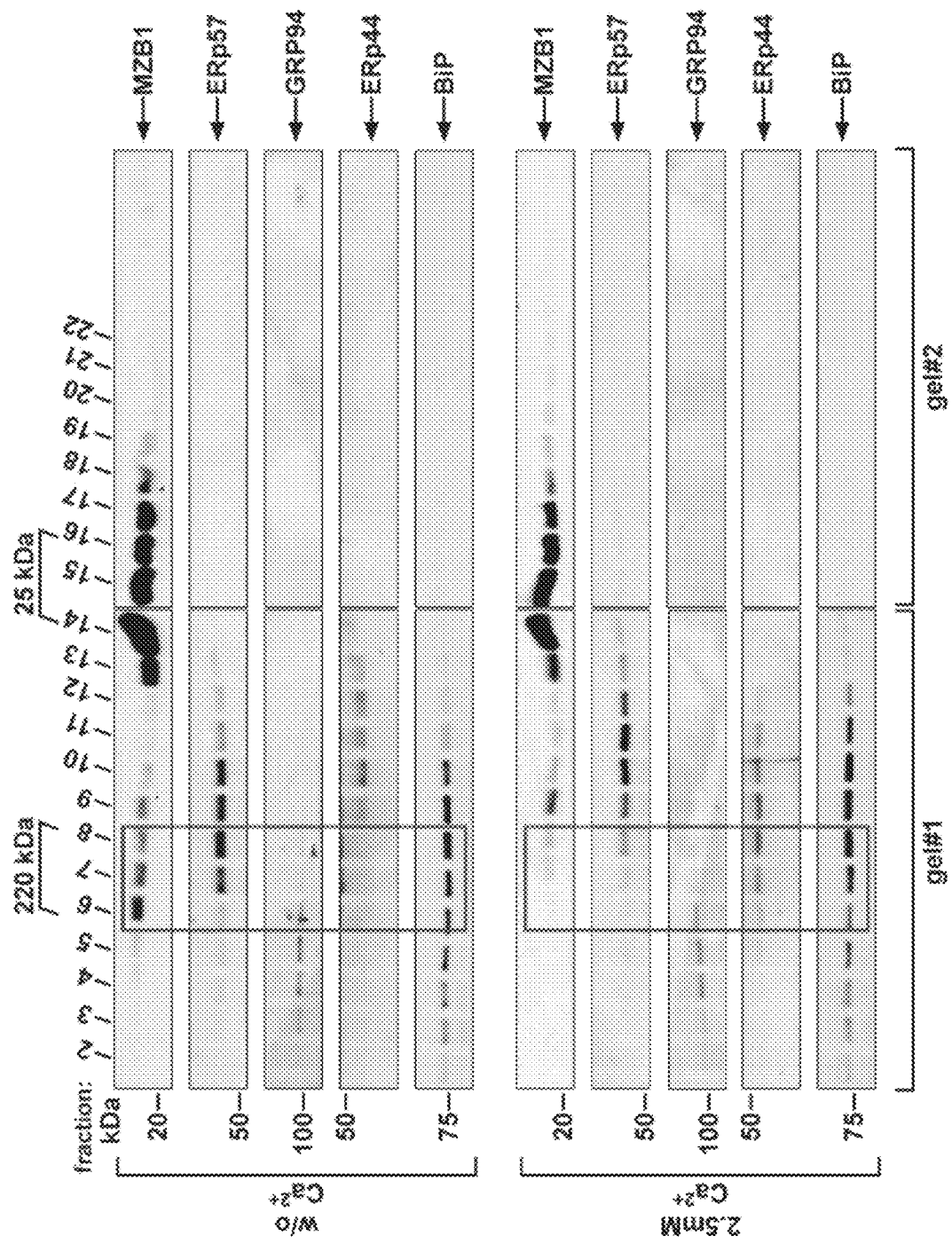

FIG. 16: Size exclusion chromatography of the endogenous MZB1, ERp57, GRP94 (Endoplasmin), ERp44 and Bip proteins in the membrane fraction of K46 cells. 500 µg membrane protein extract of K46 cells was prepared either in the presence of $Ca^{2+}$ (2.5 mM $CaCl_2$) or in its absence (10 mM EDTA), and the extracts were separated on an analytical HR10/30 Superdex 200 (Amersham/GE Healthcare) column. The immunoblot (IB) analysis was performed according to standard procedures.

Figure 17:
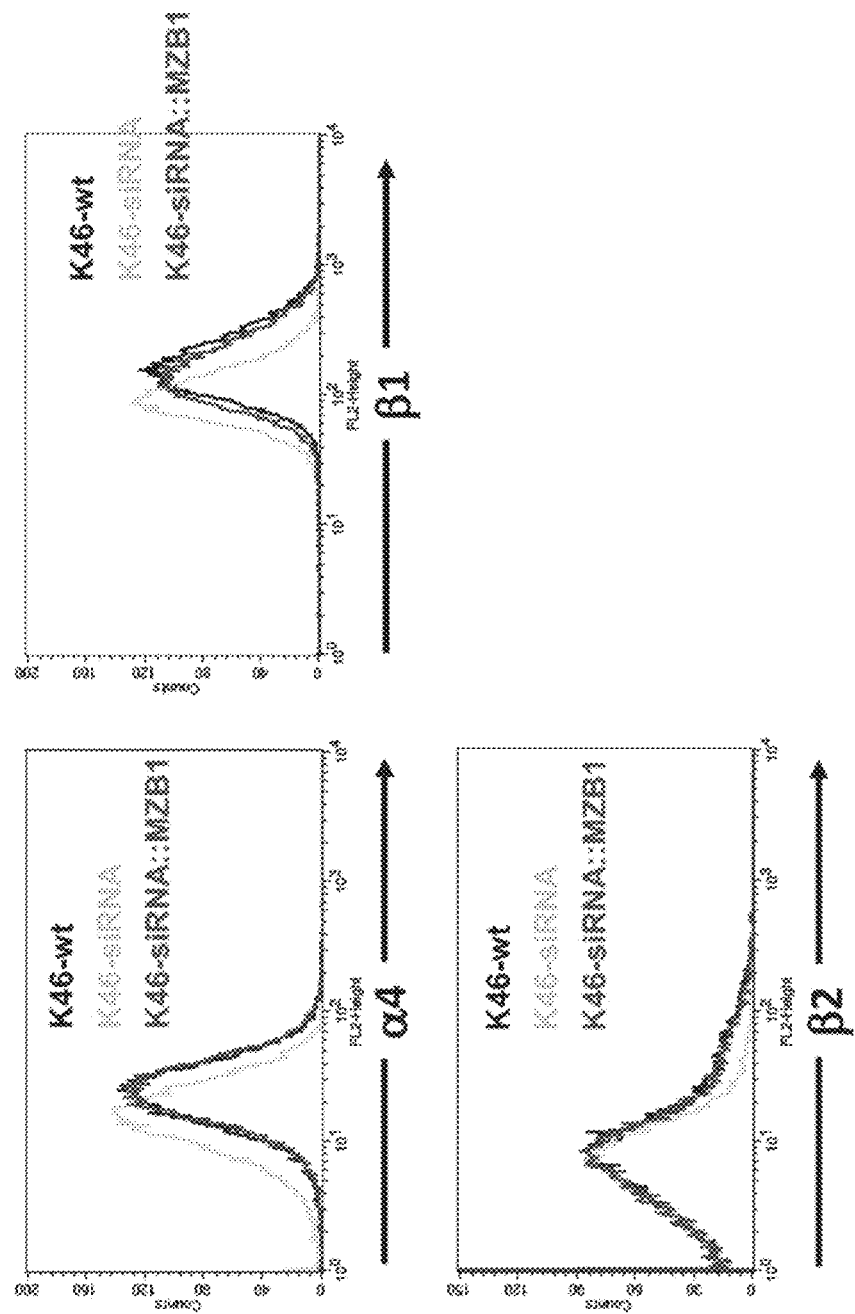

FIG. 17: FACS analysis of integrin surface expression on K46 MZB1siRNA cells. K46 wt, K46 siRNA and K46 siRNA::MZB1 cells were gated on their $GFP^+$ populations (data not shown), which were further analyzed for their integrin surface expression (α4, β1 and β2 integrins).

Figure 18:
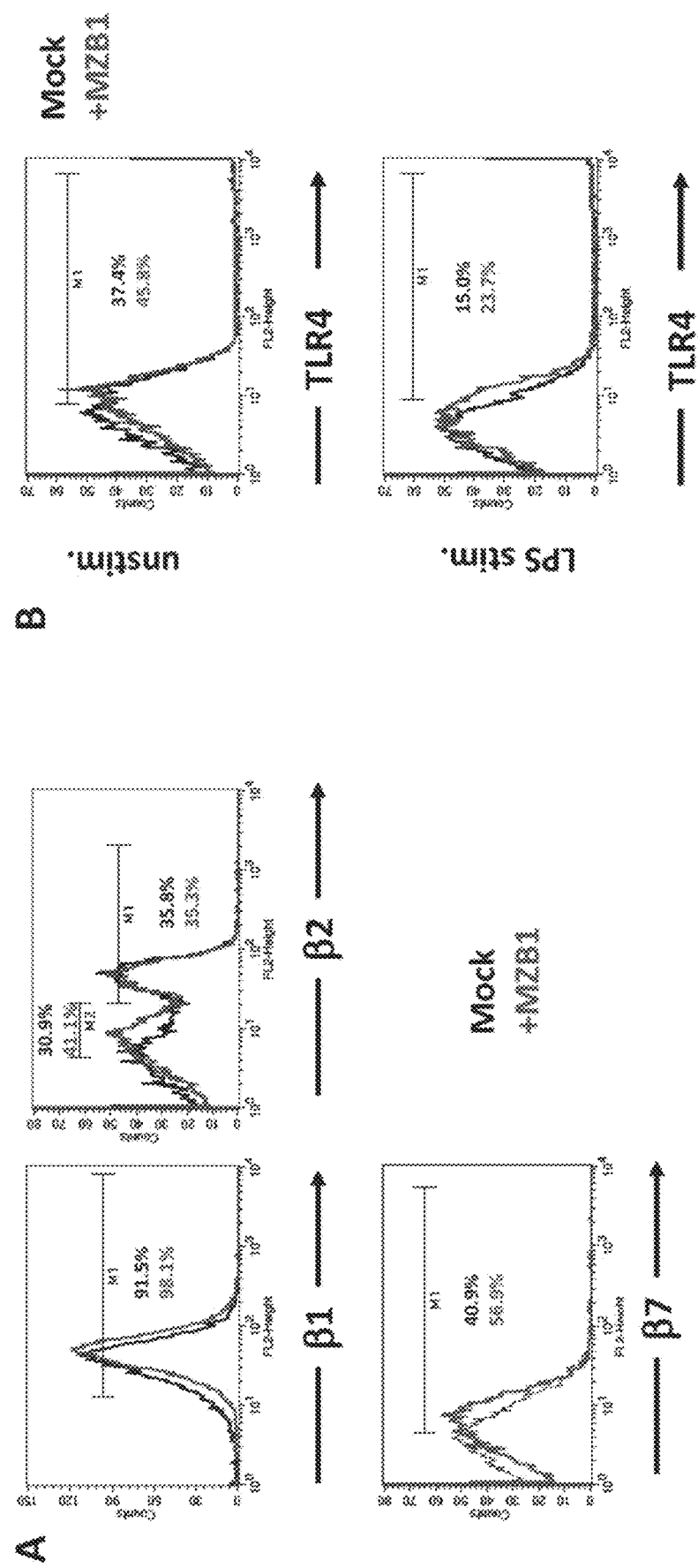

FIG. 18: FACS analysis of integrin and TLR4 surface expression on MZB1-transduced FO B cells. FACS-sorted FO B cells ($B220^+CD21^{int}CD23^{hi}$) were either retrovirally transduced with GFP alone (MOCK) or with MZB1 and GFP (+MZB1). The transduced FO B cells were gated on their $GFP^+$ populations (data not shown), which were further analyzed for their integrin surface expression (A) (β1, β2 and β7 integrins) (A) or their TLR4 surface expression (B), respectively. For the analysis of TLR4 expression. cells were either kept unstimulated or stimulated with 10 µg/ml LPS for 12 hours. Numbers indicate percentages of surface-integrin (A) or surface TLR4 (B) positive cells.

Figure 19:
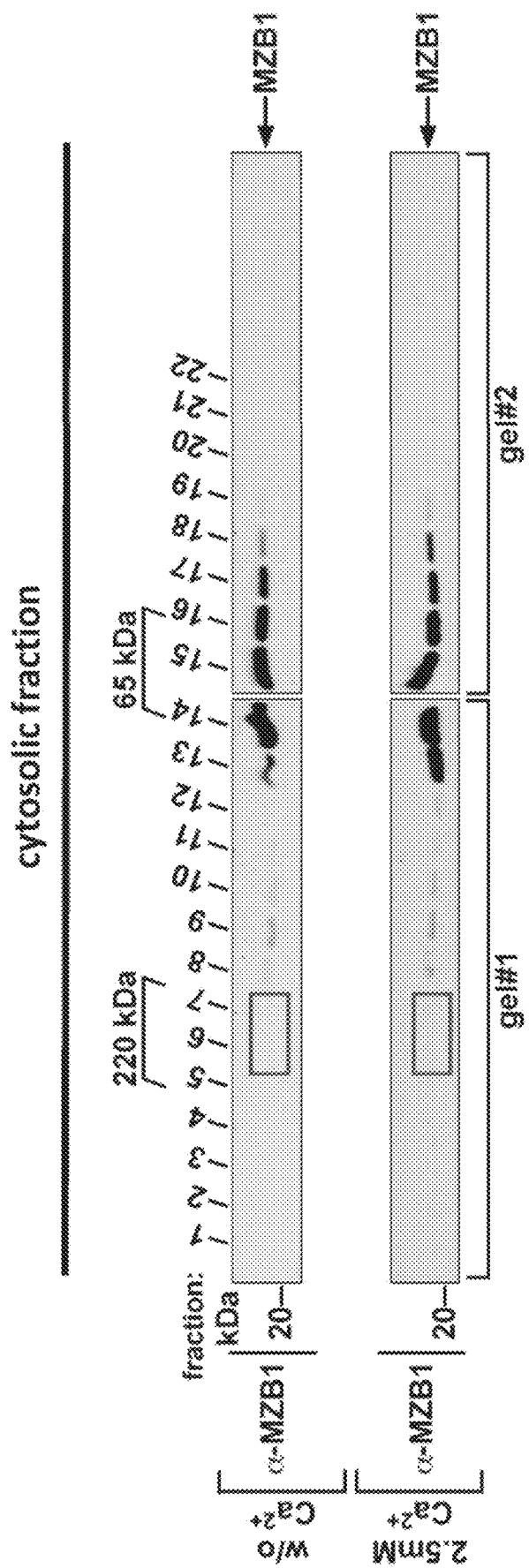

FIG. 19: Size exclusion chromatography of endogenous MZB1 protein in the cytosolic fraction of K46 cells, 500 µg cytosolic protein extract of K46 cells was prepared either in the presence of $Ca^{2+}$ (2.5 mM $CaCl_2$ or in its absence (10 mM EDTA), and the extracts were separated on an analytical HR10/30 Superdex 200 (Amersham/GE Healthcare) column. The immunoblot (IB) analysis was performed according to standard procedures.

Figure 20:
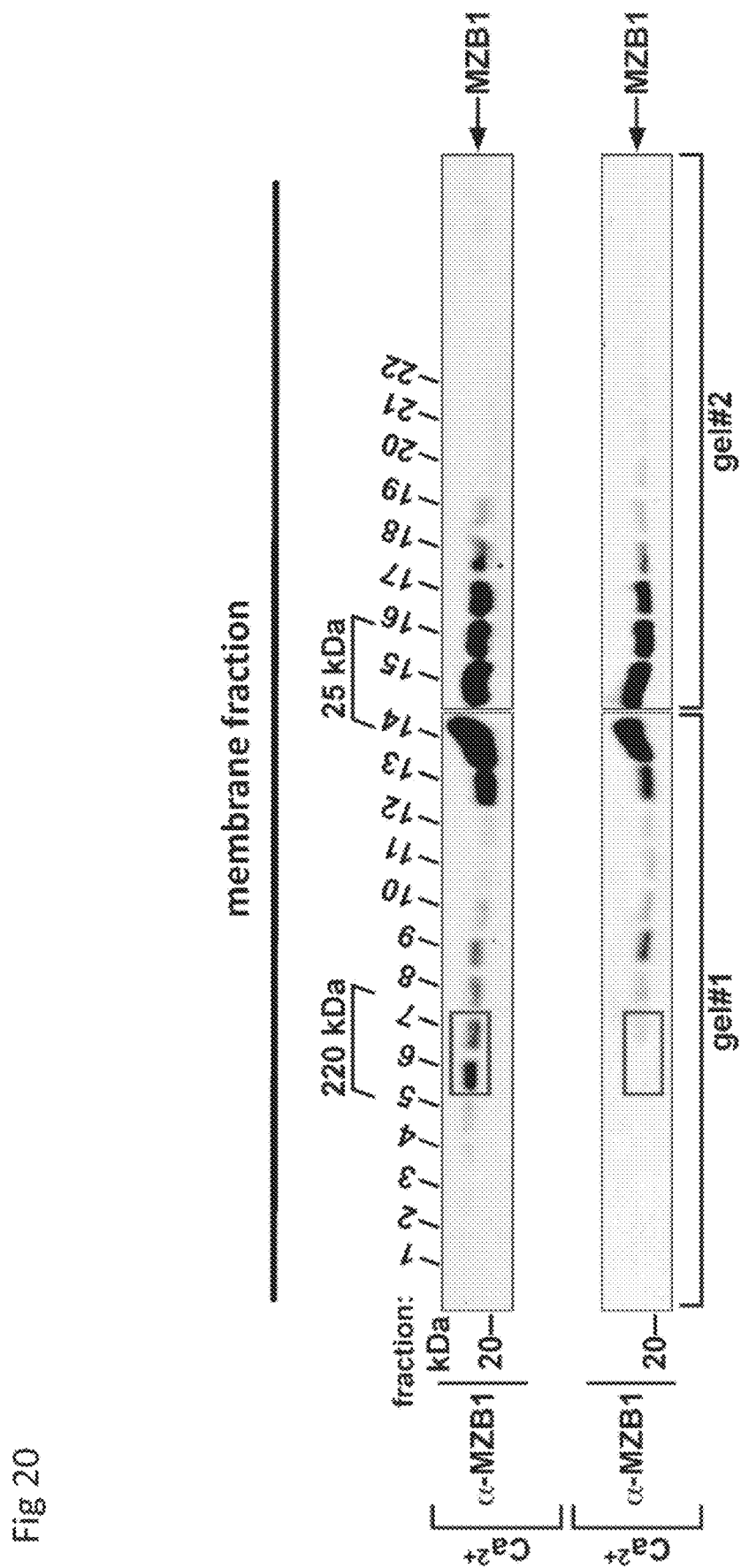

FIG. 20: Size exclusion chromatography of endogenous MZB1 protein in the membrane fraction of K46 cells. 500 µg membrane protein extract of K46 cells was prepared either in the presence of $Ca^{2+}$ (2.5 mM $CaCl_2$ or in its absence (10 mM EDTA), and the extracts were separated on an analytical HR10/30 Superdex 200 (Amersham/GE Healthcare) column. The immunoblot (IB) analysis was performed according to standard procedures.

Figure 21:
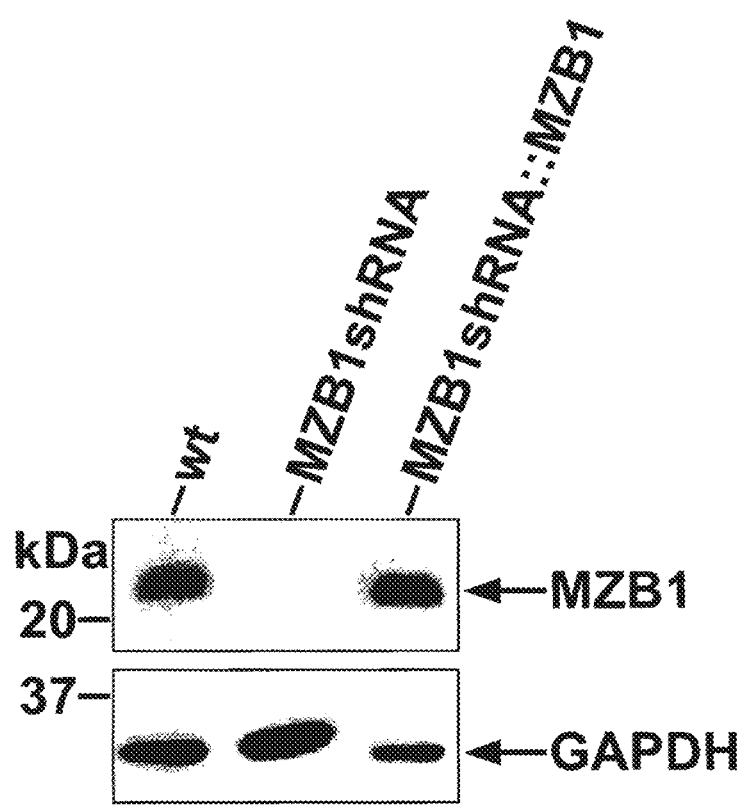

FIG. 21: Downregulation of MZB1 expression using shRNA. Immunoblot analysis with MZB1- and GAPDH-specific antibodies was performed on 20 µg of total protein extract from wt, shRNA and shRNA+MZB1 K46 cells.

Figure 22:
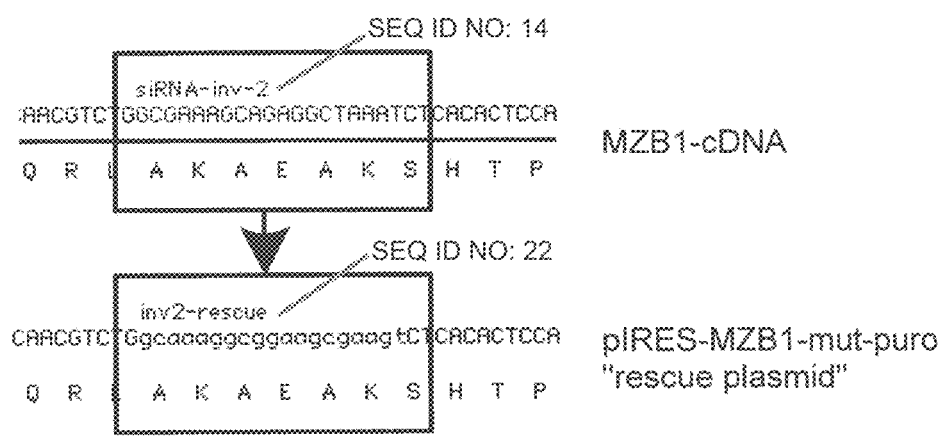

FIG. 22: Restoration of MZB1 expression in shRNA K46 cells: generation of shRNA+MZB1 K46 cells.

Figure 23:
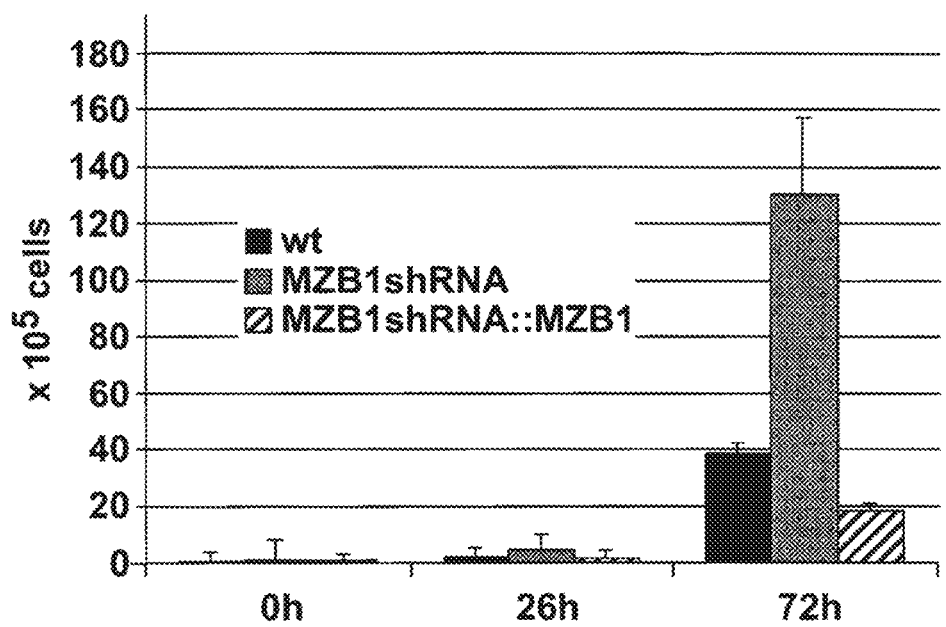

FIG. 23: Proliferation of wt, shRNA and shRNA+MZB1 K46 B cells. Cells were left untreated and cell numbers were determined using a CASY® cell counter (CASY®-technology) after 0 hours, 26 hours and 72 hours after plating. Data are expressed as the mean cell numbers of triplicate cultures.

Figure 24:
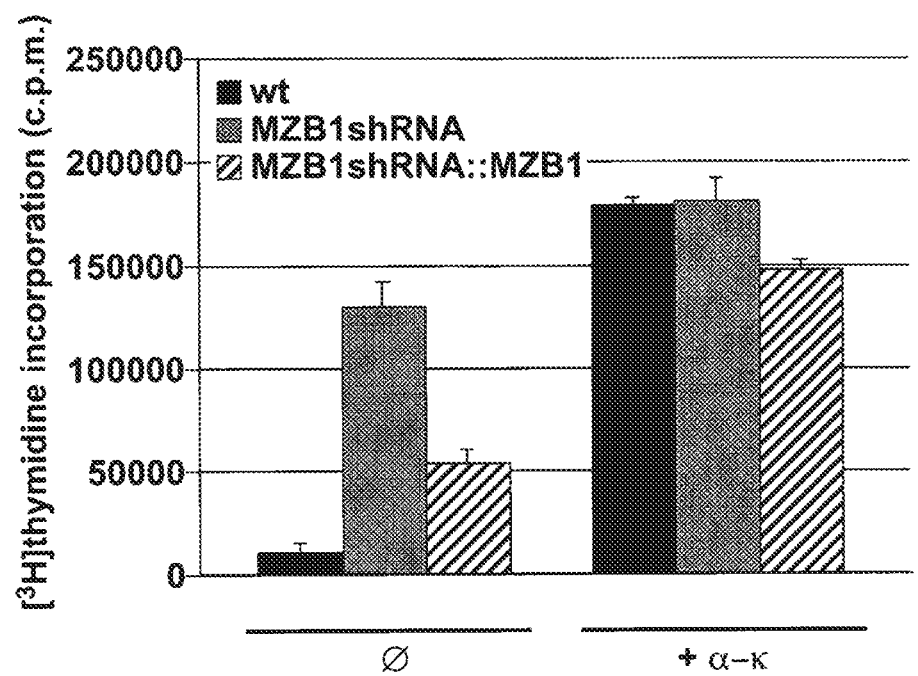

FIG. 24: Proliferation of wt, shRNA and shRNA+MZB1 K46 B cells. Cells were left untreated or treated with anti-κ (5 µg/ml) and pulsed with 1.5 µCi/well [$^3$H] thymidine for 16 h before being collected. Data are expressed as the mean [$^3$H] thymidine incorporation of triplicate cultures.

Figure 25:
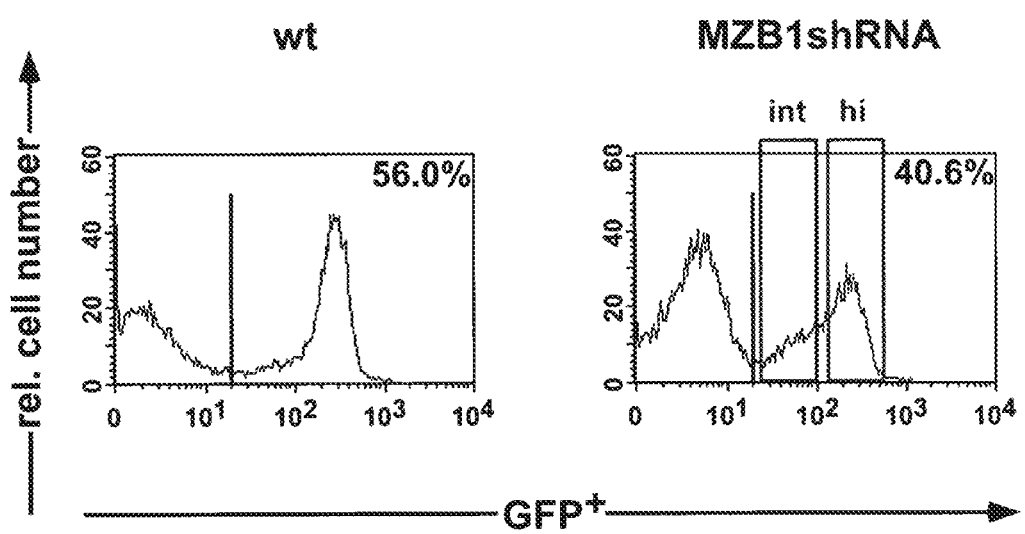

FIG. 25: GFP expression in wt and shRNA K46 B cells.

Figure 26:
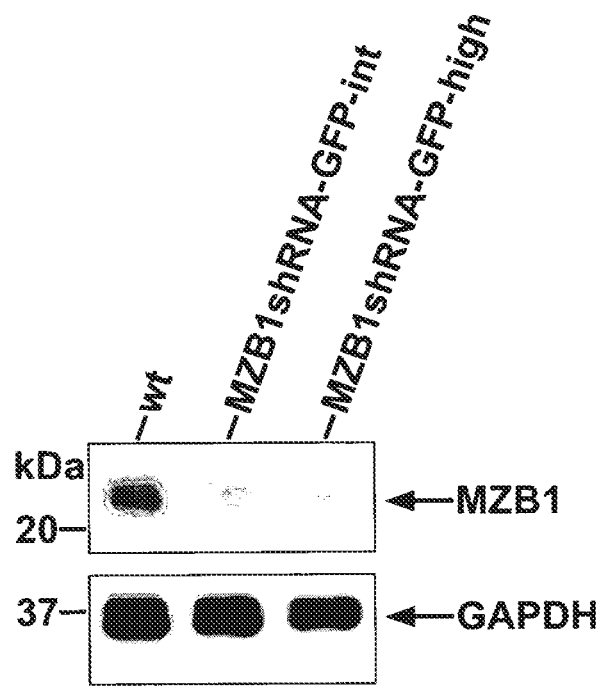

FIG. 26: Immunoblot analysis with MZB1- and GAPDH-specific antibodies was performed on 20 μg of total protein extract from wt, shRNA-GFP-int and shRNA-GFP-high K46 cells.

Figure 27:
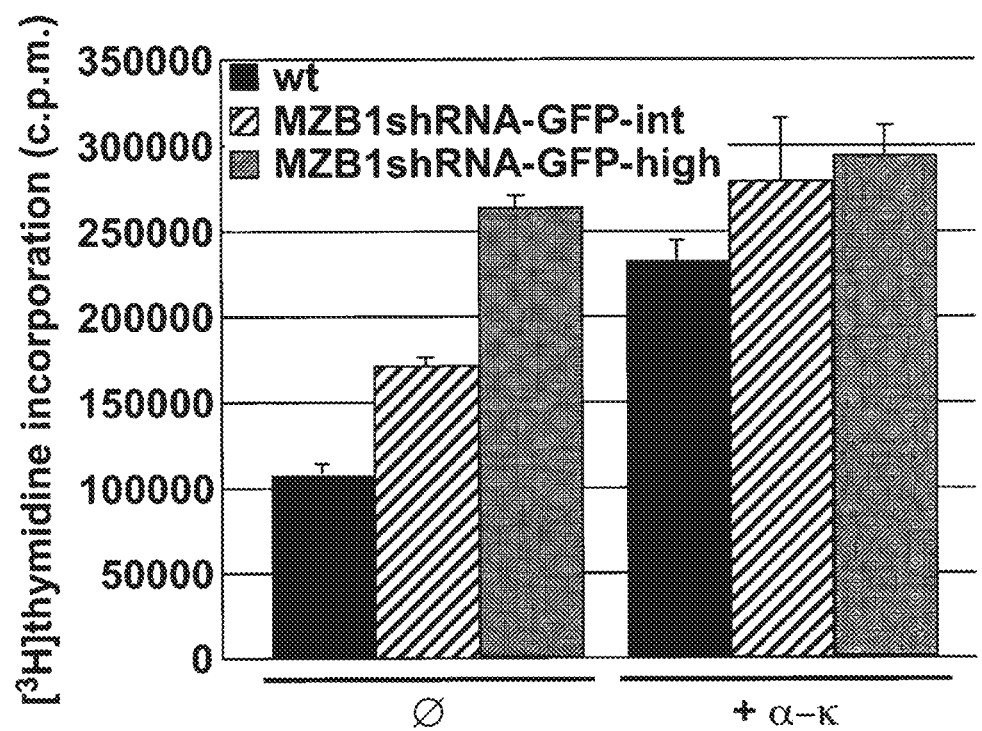

FIG. 27: Proliferation of wt, shRNA-GFP-int and shRNA-GFP-high K46 B cells. Cells were left untreated or treated with anti-κ (5 μg/ml) and pulsed with 1.5 μCi [$^3$H] thymidine for 16 h before being collected. Data are expressed as the mean [$^3$H] thymidine incorporation of triplicate cultures.

Figure 28:
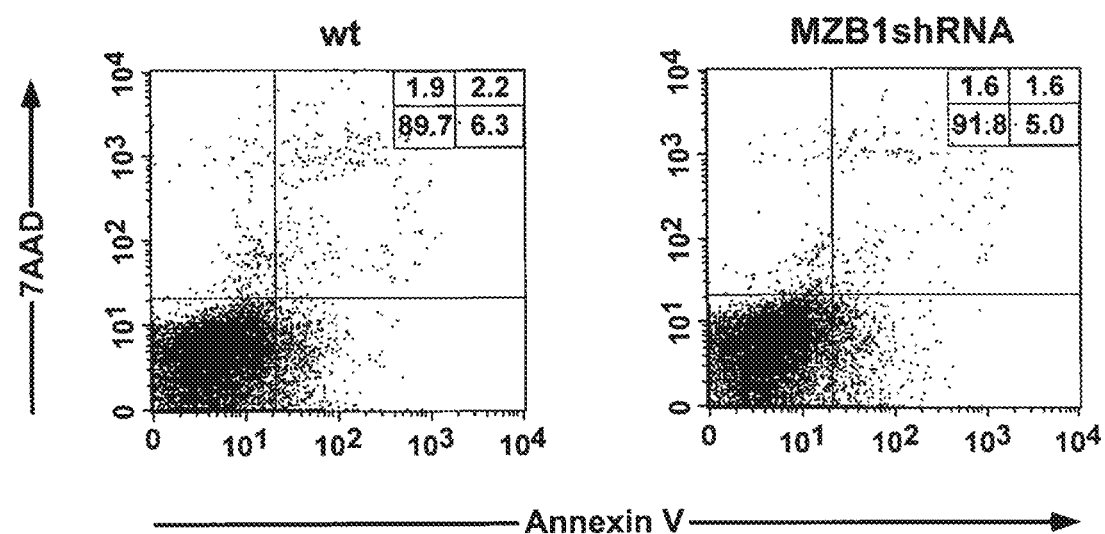

FIG. 28: Annexin V-PE Staining. K46-wt or K46-shRNA cells were washed with cold PBS and incubated with Annexin V-PE in a buffer containing 7-amino-actinomycin D (7AAD). After incubating the cells at RT in the dark, the samples were analyzed by flow cytometry on a FACSCalibur flow cytometer.

Figure 29:
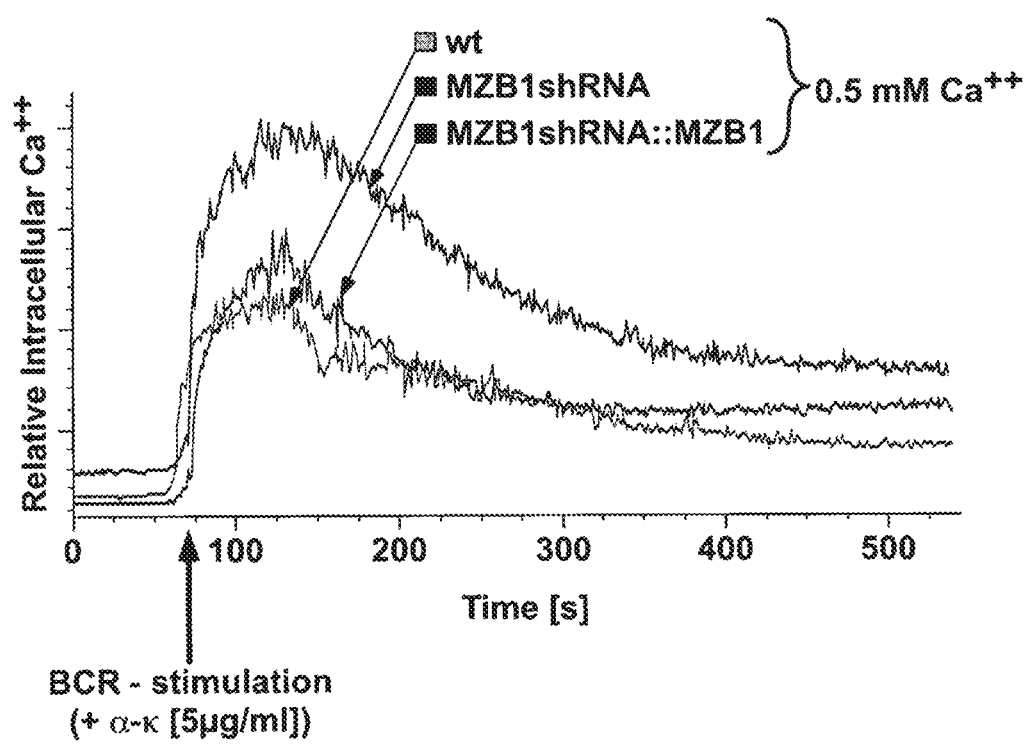

FIG. 29: Downregulation of MZB1 in K46 mature B cells changes BCR signaling capacity. $Ca^{2+}$ mobilization upon BCR engagement in wt, shRNA and shRNA+MZB1 K46 cells. Cells were stimulated with anti-κ (5 μg/ml) in 0.5 mM $Ca^{2+}$ containing media and increases in free intracellular $Ca^{2+}$ were measured in real time using a FACSAria Flow-Cytometer.

Figure 30:
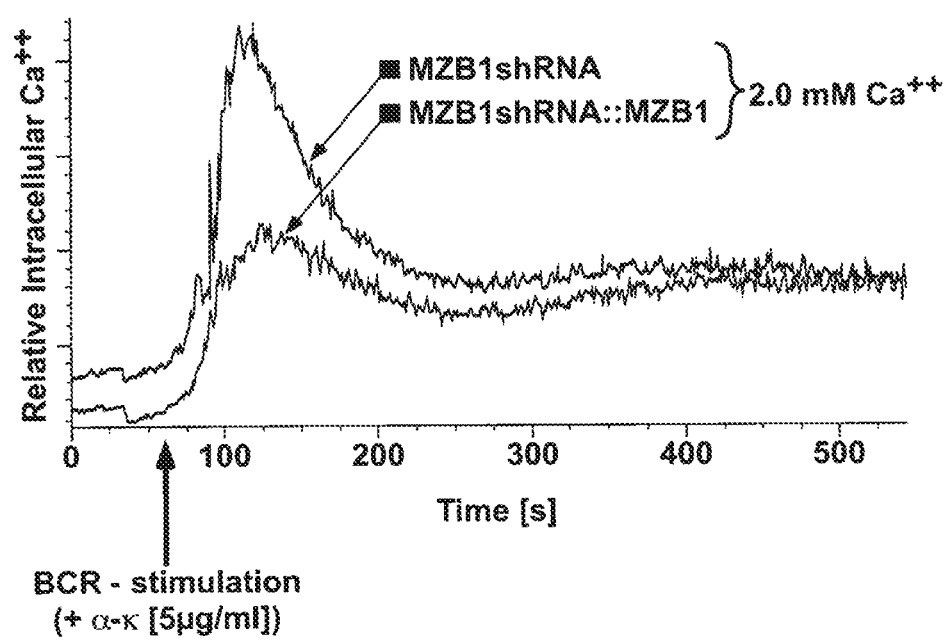

FIG. 30: Downregulation of MZB1 in K46 mature B cells changes BCR signaling capacity. $Ca^{2+}$ mobilization upon BCR engagement in shRNA and shRNA+MZB1 K46 cells. Cells were stimulated with anti-κ (5 μg/ml) in 2.0 mM $Ca^{2+}$ containing media and increases in free intracellular $Ca^{2+}$ were measured in real time using a FACSAria Flow-Cytometer.

Figure 31:
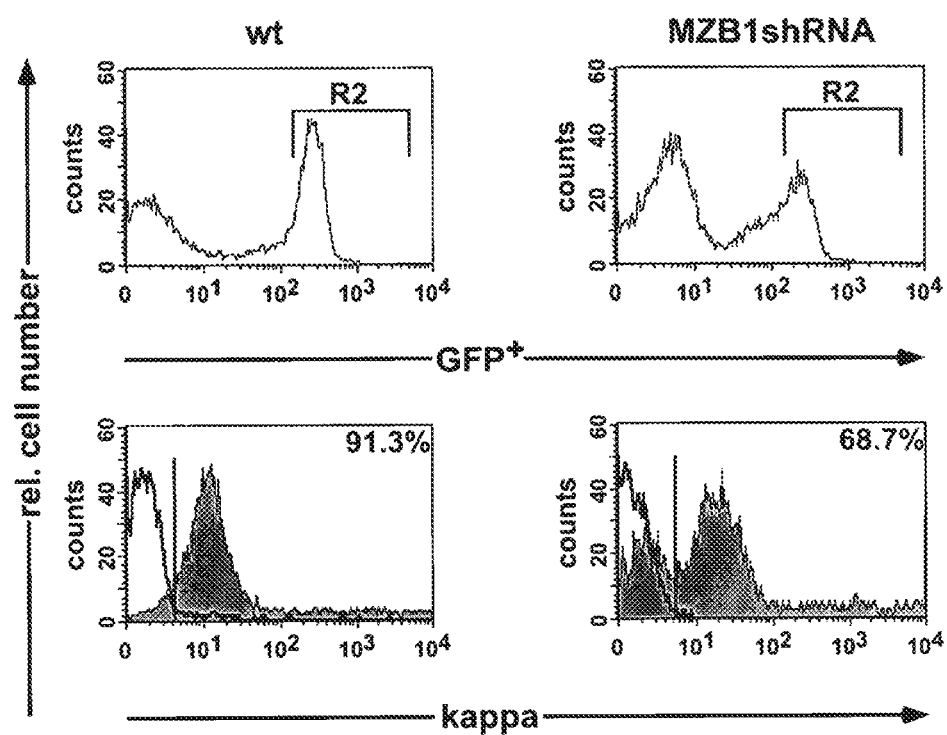

FIG. 31: Surface BCR expression in wt and shRNA K46 B cells. Cells were stained with kappa light chain-specific antibodies and subjected to FACS analysis. Cells were gated for GFP$^+$.

Figure 32:
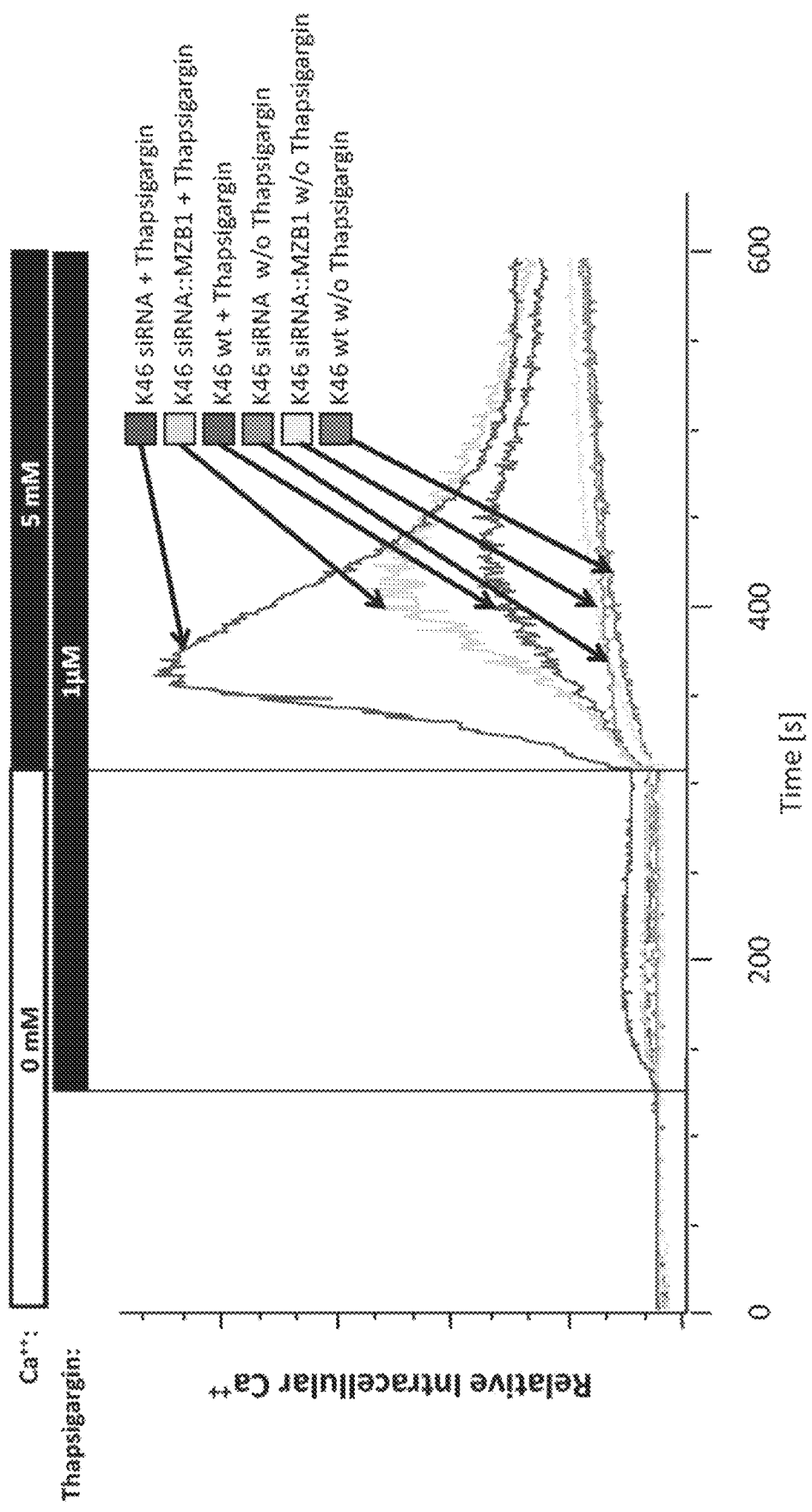

FIG. 32: MZB1 regulates $Ca^{2+}$ flux in K46 mature B cells. Measurement of $Ca^{2+}$ flux of Indo-1 AM loaded K46 B cells (wt), K46-MZB1-siRNA cells and K46-MZB1-siRNA cells with restored MZB1-expression after treatment with 1 μM thapsigargin. Cells were placed in medium where extracellular $Ca^{2+}$ was chelated by EGTA, and after addition of 1 μM thapsigargin, 5 mM of $Ca^{2+}$ was added at the indicated time point. Increases in free intracellular $Ca^{2+}$ were measured in real time using a FACSAria Flow-Cytometer, FIG. 33: MZB1 redistributes into punctuate structures after ER $Ca^{2+}$ store depletion. NIH 3T3 fibroblastic cells were stably transfected with MZB1-GFP and plated out in phenolred-free Dulbecco's Modified Eagle Medium low glucose supplemented with 10% FCS, 2 mM L-Glutamine as well as 0.1 mg/ml Streptomycin and 10 U/ml Penicillin in ibidi 35 mm high μ-dishes at a density of 2.5×10$^4$ cells per ml. The next day, dishes were subjected to confocal imaging analysis (Leics Confocal) before (0 min) and after (30 min) addition of 1 μM thapsigargin and 3 mM EGTA.

Figure 34:
Figure 34:
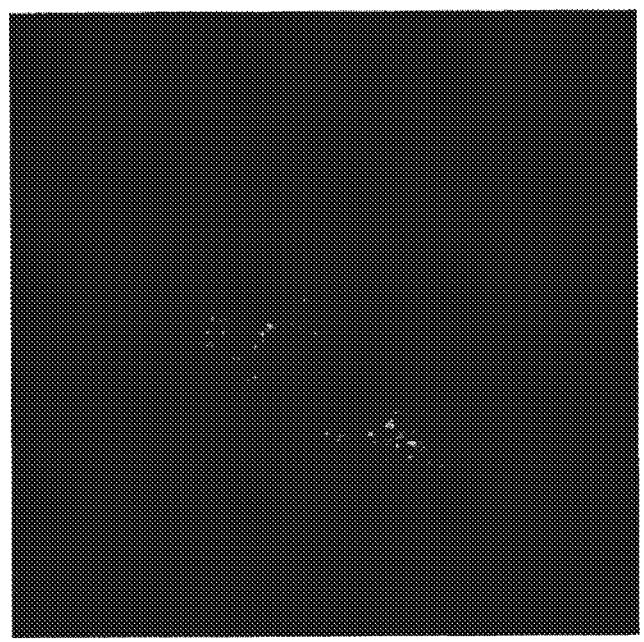

FIG. 34: MZB1 redistributes into punctuate structures after ER $Ca^{2+}$ store depletion. NIH 3T3 fibroblastic cells were stably transfected with MZB1-GFP and plated out in phenolred-free Dulbecco's Modified Eagle Medium low glucose supplemented with 10% FCS, 2 mM L-Glutamine as well as 0.1 mg/ml Streptomycin and 10 U/ml Penicillin in ibidi 35 mm high μ-dishes at a density of 2.5×10$^4$ cells per ml. The next day, dishes were subjected to confocal imaging analysis (Leica Confocal) before (0 min) and after (30 min) addition of DMSO.

Figure 35:
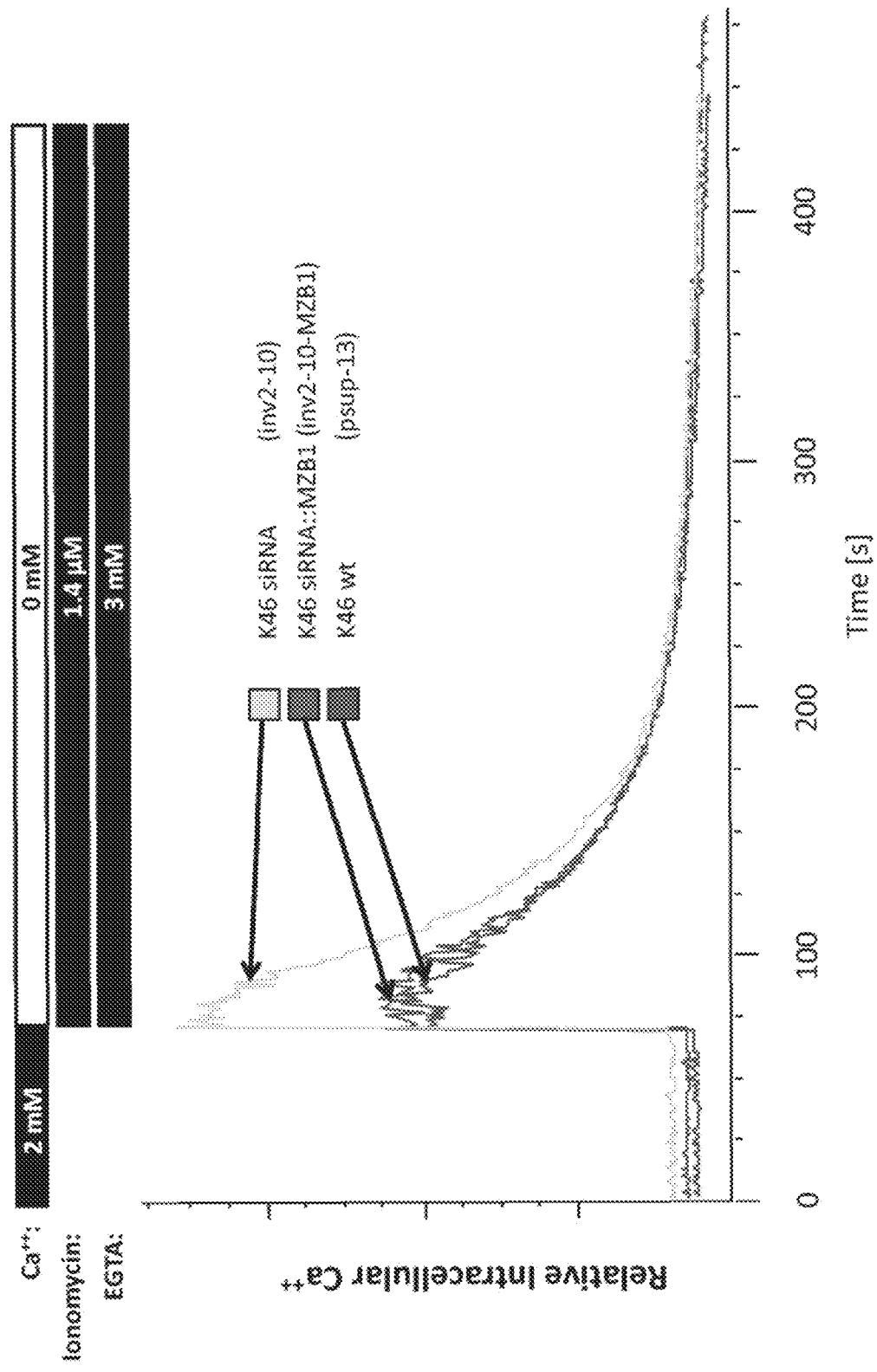

FIG. 35: MZB1 regulates ER-$Ca^{2+}$ stores in K46 mature B cells. Measurement of $Ca^{2+}$ flux of Indo-1 AM loaded K46 B cells (wt), K46-MZB1-siRNA cells and K46-MZB1-siRNA cells with restored MZB1-expression after treatment with 1.4 μM ionomycin. Cells were placed in medium containing 2.5 mM $Ca^{2+}$ followed by the simultaneous addition of 1 μM thapsigargin and 3 mM EGTA at the indicated time point. Increases in free intracellular $Ca^{2+}$ were measured in real time using a FACSAria Flow-Cytometer.

Figure 36:
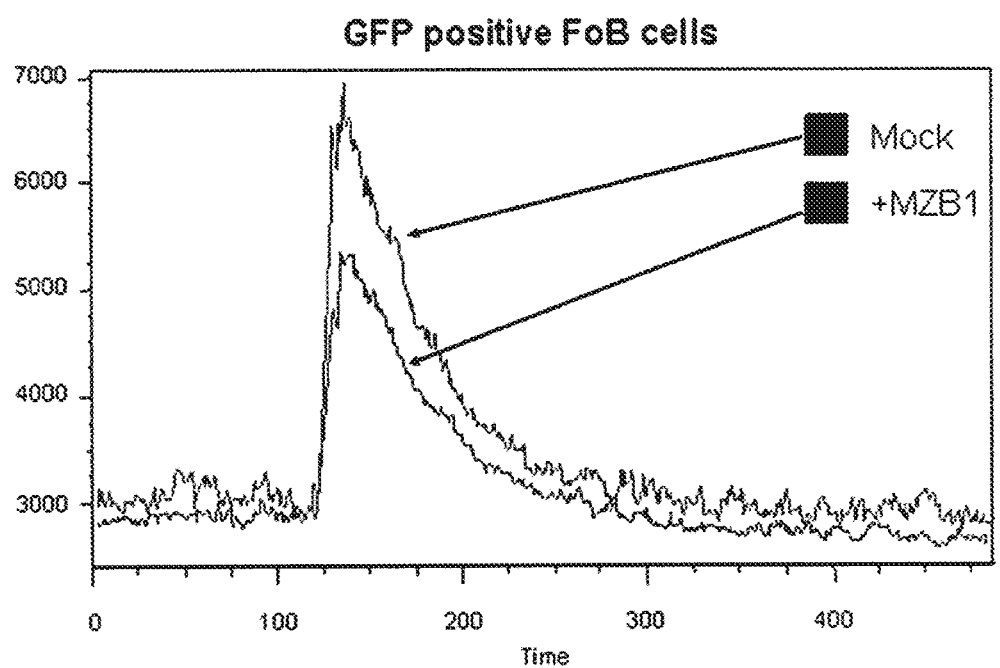
Figure 36:
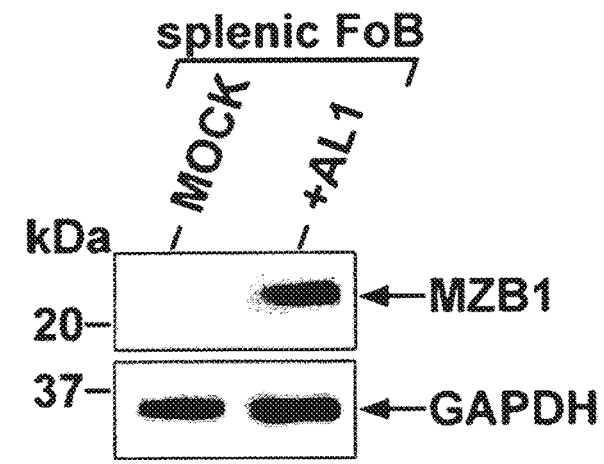

FIG. 36: MZB1 increases ER-$Ca^{2+}$ stores in MZB1-transduced FO B cells.

(A) FACS-sorted FOB cells (B220$^+$CD21$^{int}$CD23$^{hi}$) were either retrovirally transduced with GFP alone (MOCK) or with MZB1 and GFP (+MZB1). Transduced, GFP$^+$FO B cells were placed in medium containing 2 mM $Ca^{2+}$ followed by the simultaneous addition of 1.4 μM thapsigargin and 3 mM EGTA at the indicated time point. Increases in free intracellular $Ca^{2+}$ were measured in real time using a FACSAria Flow-Cytometer. The figure displays the gate for transduced, GFP$^+$ cells.

(B) FACS-sorted FOB cells (B220$^+$CD21$^{int}$CD23$^{hi}$) were either retrovirally transduced with GFP alone (MOCK) or with AL1 and GFP (+AL1). Transduced, GFP$^+$ FO B cells were enriched by FACS-sorting. An immunoblot analysis with AL1-specific antibodies (clone 2F9) was performed on 20 mg total protein extracts from splenic FO B cells, infected with the AL1- and GFP-expressing (+AL1) or the solely GFP-expressing retrovirus (MOCK). As a control for loading and transfer, an additional immunoblot analysis using a GAPDH-specific antibody was performed.

Figure 37:
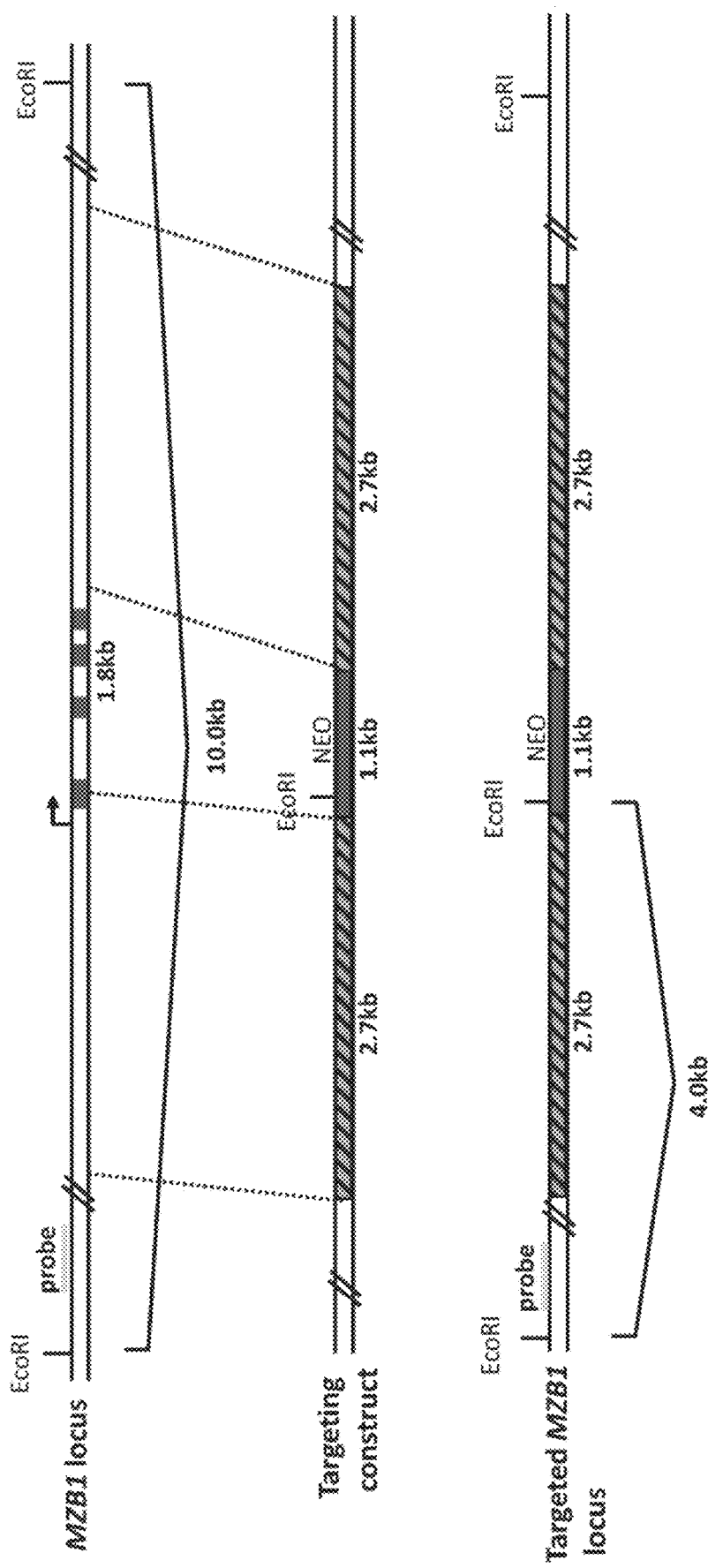

FIG. 37: Genetic inactivation of the mzb1 locus via homologous recombination. Neo: neomycin phosphotransferase gene.

Figure 38:
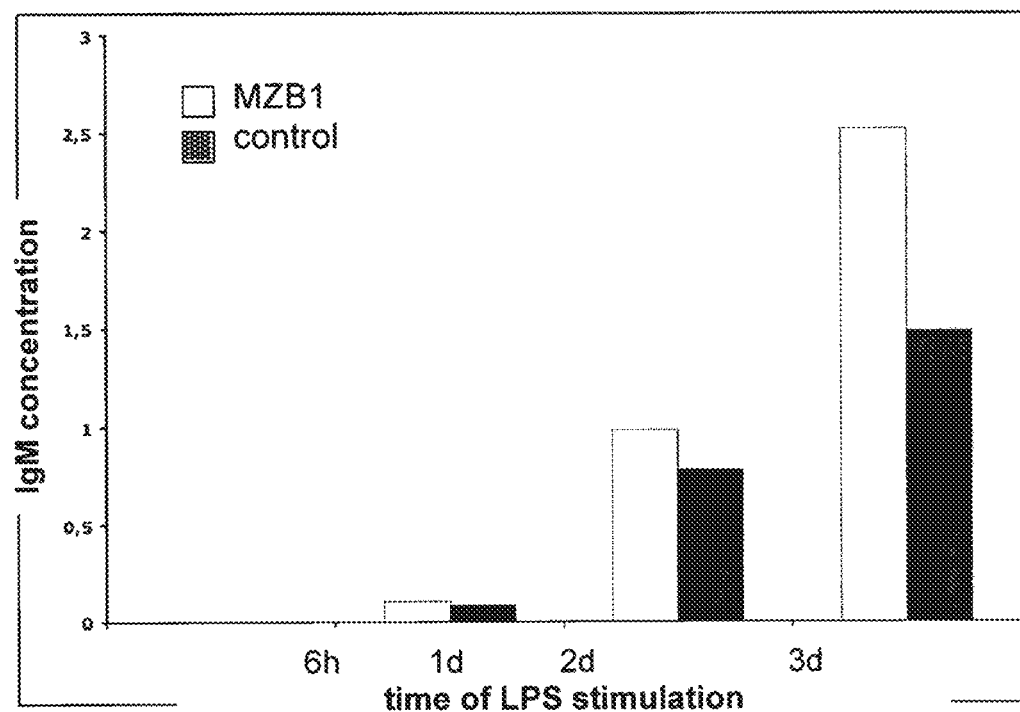

FIG. 38: Secretion of IgM antibodies in follicular B cells overexpressing MZB1 and stimulated with LPS. Primary follicular B cells were infected with an MZB1-expressing retrovirus pEG2-MZB1 and an empty vector control retrovirus pEG2-MCS. Infected cells were stimulated with 1.0 μg/ml LPS. IgM concentration in the cell culture supernatant was determined by ELISA 6 hours, 1 day, 2 days, and 3 three days post-stimulation.

Figure 39:
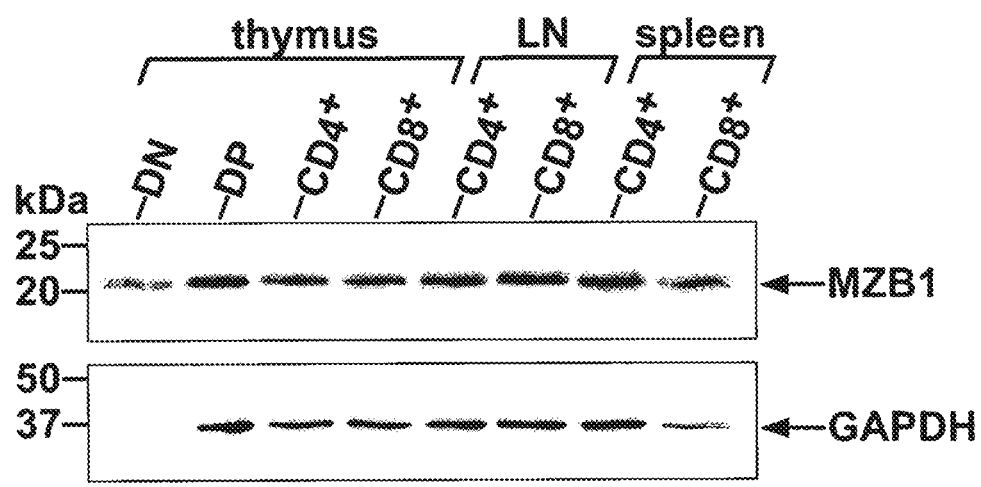

FIG. 39: MZB1 expression in different T cell populations derived from transgenic mice. An immunoblot analysis with MZB1-specific antibodies (clone 2F9) was performed on 304 total protein extracts from thymus derived double negative (DN; CD4$^-$ and CD8$^-$) T cell progenitors, thymus derived double positive (DP; CD4$^+$ and CD8$^+$) T cell progenitors, CD4$^+$ and CD8$^+$ single positive thymocytes, and in addition, from CD4$^+$ as well as CD8$^+$ single positive splenic and lymph node derived peripheral T cells. All cells analyzed were isolated from 5-9 weeks old transgenic mice. As a control for loading and transfer an additional immunoblot analysis using a GAPDH-specific antibody was performed.

Figure 40:
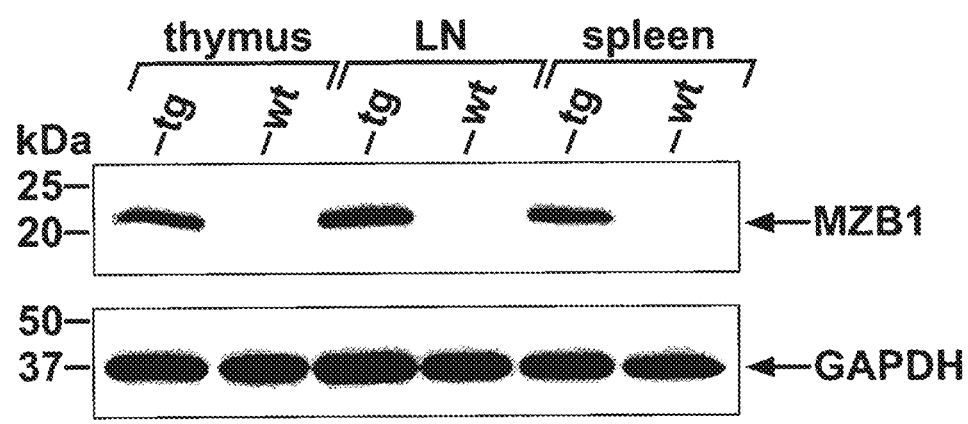

FIG. 40: MZB1 expression in different T cell populations derived from transgenic mice and their corresponding wt littermates. An immunoblot analysis with MZB1-specific antibodies (clone 2F9) was performed on 30 μg total protein extracts from thymus-, lymph node-, and spleen-derived CD4$^+$ as well as CD8$^+$ single positive T cells (mixture of CD4$^+$ and CD8$^+$ single positive cells). All cells analyzed were isolated from 5-9 weeks old transgenic mice or their corresponding wt littermates. As a control for loading and transfer an additional immunoblot analysis using a GAPDH-specific antibody was performed.

Figure 41:
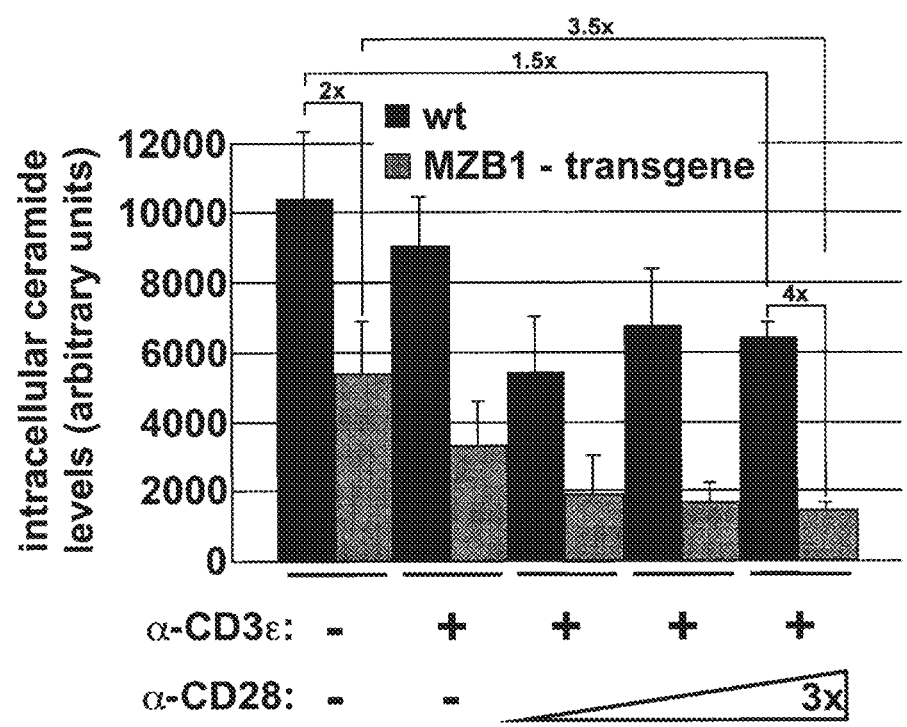

FIG. 41: Measurement of endogenous ceramide levels in CD4$^+$ splenic T cells derived from transgenic mice and their corresponding wt littermates. FACS-sorted CD4⁺ splenocytes, either isolated from 5-9 weeks old transgenic mice or their corresponding wt littermates were left untreated or induced with α-CD28 (0.1 µg/ml, 0.3 µg/ml; or 1.0 µg/ml), α-CD3ε (0.3 µg/ml) or both for 36 hours. Cells were harvested and endogenous ceramide was extracted. The isolated sphingomyelin-derived ceramide was radioactively labeled by performing a DAG kinase assay using [γ-$^{32}$P] ATP. The resulting [$^{32}$P]ceramide was quantified using a phosphor-imager system (Fuji) and the Alphalmager™-quantification software (Alpha Innotech) following thin-layer chromatography (TLC). Data are expressed as the mean intensity of [$^{32}$P]ceramide-spots on the TLC plates of duplicate cultures. The figure is a representative of three independent experiments.

Figure 42:
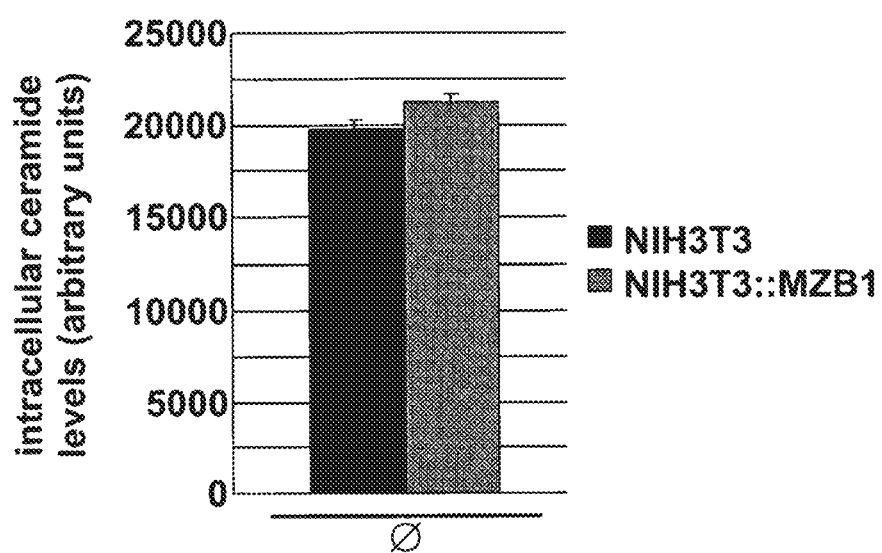

FIG. 42: Measurement of endogenous ceramide levels in wt fibroblasts compared to fibroblast cells stably expressing MZB1. Non-stimulated (Ø) NIH 3T3 cells (NIH3T3) and NIH 3T3 cells stably transfected with FLAG-MZB1 (NIH3T3::MZB1) were grown to confluency, cells were harvested and endogenous ceramide was extracted. The isolated ceramide was radioactively labeled by performing a DAG kinase assay using [γ-$^{32}$P]ATP. The resulting [$^{32}$P] ceramide was quantified using a phosphor-imager system (Fuji) and the Alphalmager™-quantification software (Alpha Innotech) following thin-layer chromatography (TLC). Data are expressed as the mean intensity of [$^{32}$P]ceramide-spots on the TLC plates of duplicate cultures. The figure is a representative of three independent experiments.

Figure 43:
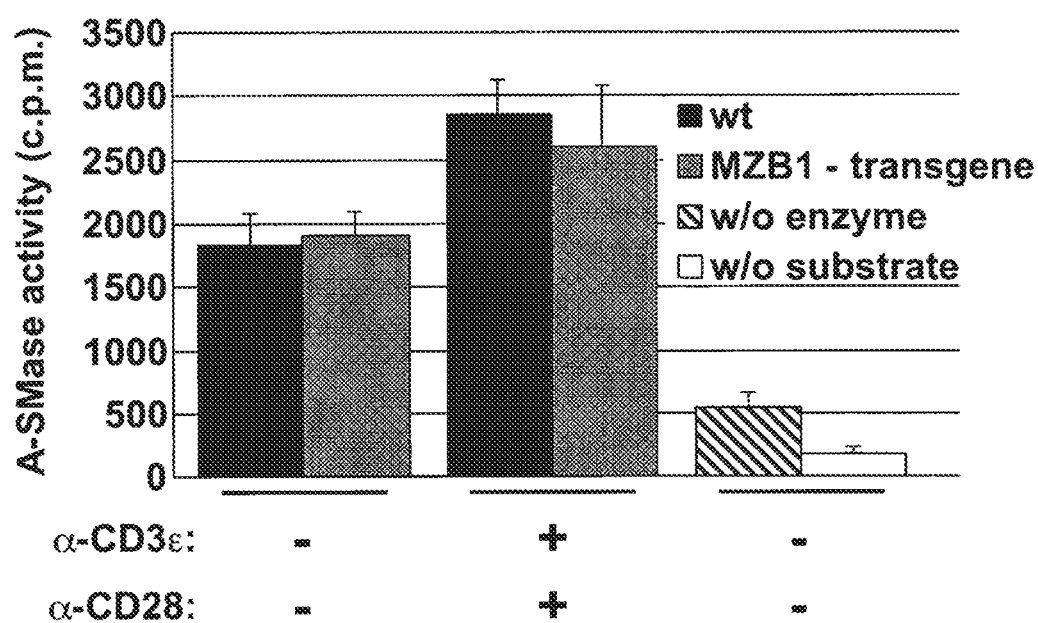

FIG. 43: Measurement of endogenous A-SMase activity in CD4⁺ splenic T cells derived from transgenic mice and their corresponding wt littermates, MACS®-purified CD4⁺ splenocytes, either isolated from 5-9 weeks old transgenic mice or their corresponding wt littermates were left untreated or induced with both α-CD28 (1.0 µg/ml) and α-CD3ε (0.3 µg/ml) for 36 hours. Cells were harvested, lysed and the cellular extracts (50 µg total protein) were incubated in the appropriate buffer conditions, being specific for acid-SMases (pH 5.0). Prior to incubation, [N-methyl-$^{14}$C]sphingomyelin (Amersham/GE Healthcare) as radioactively labeled substrate was added. The amount of $C^{14}$-labeled phosphorylcholine produced by A-SMases from [$^{14}$C]sphingomyelin was measured by scintillation counting. Data are expressed as the mean c.p.m. ([$^{14}$C]phosphorylcholine) of duplicate cultures. As a control, samples without cellular extracts (w/o enzyme) and samples without radioactively labeled substrate (w/o enzyme) were performed. The figure is a representative of three independent experiments.

Figure 44:
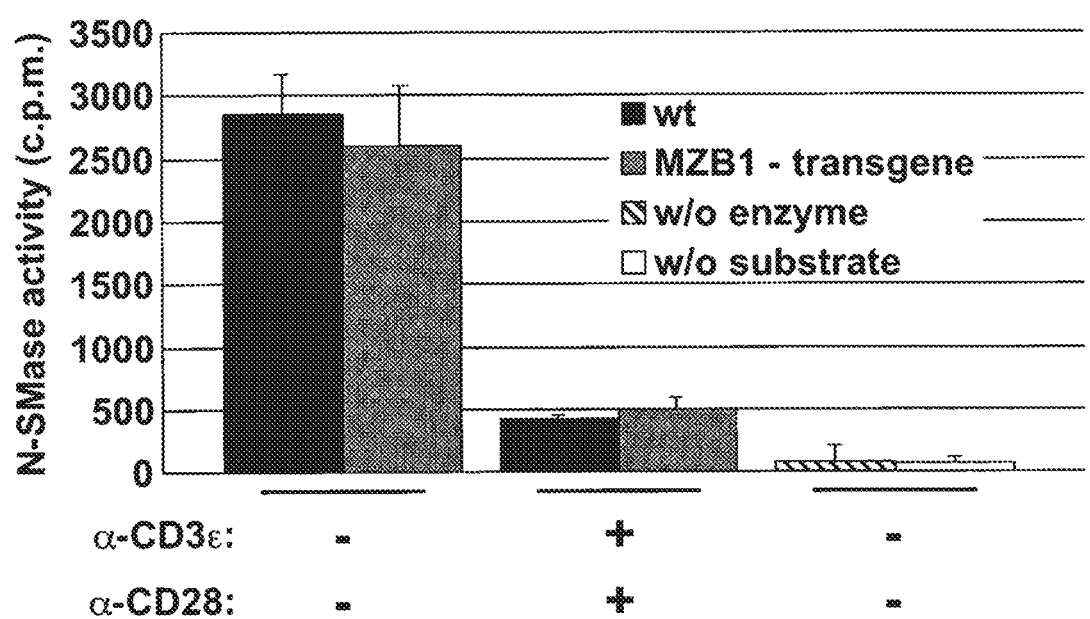

FIG. 44: Measurement of endogenous N-SMase activity in CD4⁺ splenic T cells derived from transgenic mice and their corresponding wt littermates. MACS®-purified CD4⁺ splenocytes, either isolated from 5-9 weeks old transgenic mice or their corresponding wt littermates were left untreated or induced with both α-CD28 (1.0 µg/ml) and α-CD3ε (0.3 µg/ml) for 36 hours. Cells were harvested, lysed and the cellular extracts (50 µg total protein) were incubated in the appropriate buffer conditions, being specific for neutral-SMases (pH 7.4). Prior to incubation, [N-methyl-$^{14}$C]sphingomyelin (Amersham/GE Healthcare) as radioactively labeled substrate was added. The amount of $C^{14}$-labeled phosphorylcholine produced by N-SMases from [$^{14}$C]sphingomyelin was measured by scintillation counting. Data are expressed as the mean c.p.m. ([$^{14}$C]phosphorylcholine) of duplicate cultures. As a control, samples without cellular extracts (w/o enzyme) and samples without radioactively labeled substrate (w/o enzyme) were performed. The Figure is a representative of three independent experiments.

Figure 45:
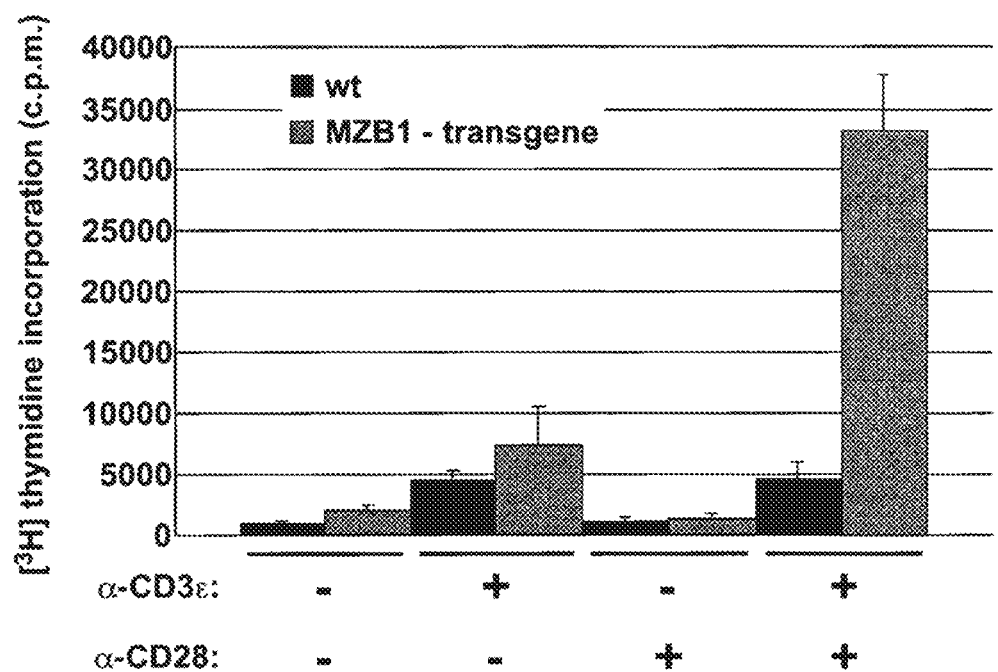

FIG. 45: Measurement of [$^{3}$H]thymidine incorporation in CD4⁺ lymph node-derived T cells isolated from transgenic mice and their corresponding wt littermates. LN-derived, FACS-sorted CD4⁺ T cells, either isolated from 5-9 weeks old transgenic mice or their corresponding wt littermates were plated in a 96 well format. Cells were either left untreated or induced with α-CD28 (0.1 µg/ml), α-CD3ε (0.3 µg/ml) or both for 12 hours. Each well was pulsed with 1.5 µCi [$^{3}$H]thymidine 12 h-16 h before being collected. Data are expressed as the mean [$^{3}$H]thymidine incorporation of triplicate cultures. The figure is a representative of three independent experiments.

Figure 46:
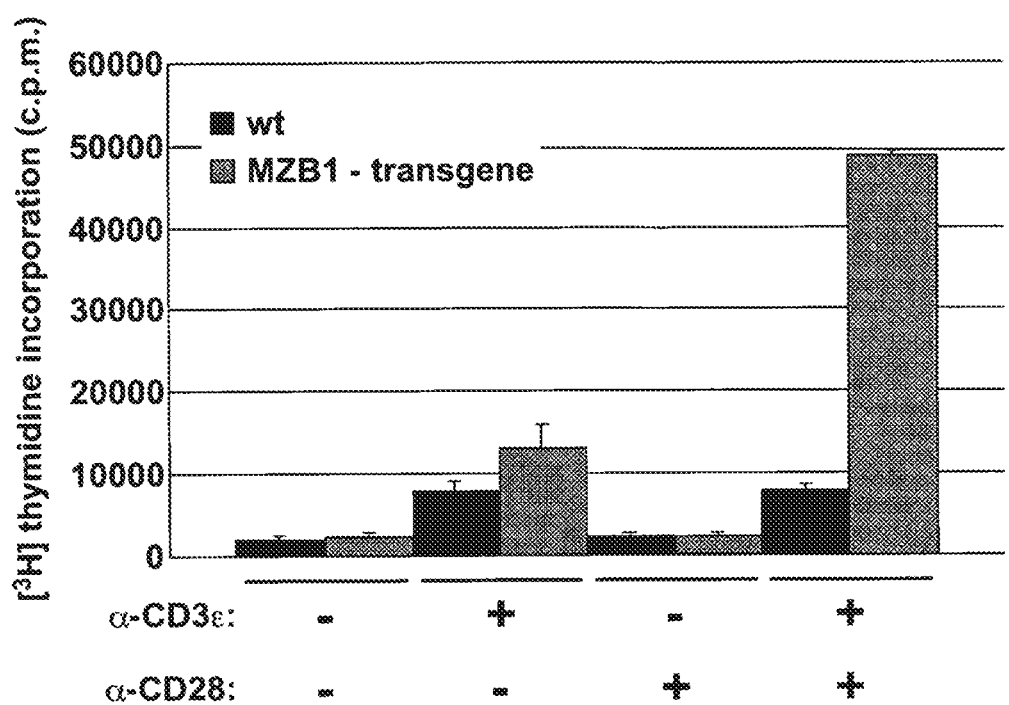

FIG. 46: Measurement of [$^{3}$H]thymidine incorporation in CD4⁺ splenic T cells isolated from transgenic mice and their corresponding wt littermates. FACS-sorted splenic CD4⁺ T cells, either isolated from 5-9 weeks old transgenic mice or their corresponding wt littermates were plated in a 96 well format. Cells were either left untreated or induced with α-CD28 (0.1 µg/ml), α-CD3ε (0.3 µg/ml) or both for 12 hours. Each well was pulsed with 1.5 µCi [$^{3}$H]thymidine 12 h-16 h before being collected. Data are expressed as the mean [$^{3}$H]thymidine incorporation of triplicate cultures. The figure is a representative of three independent experiments.

Figure 47:
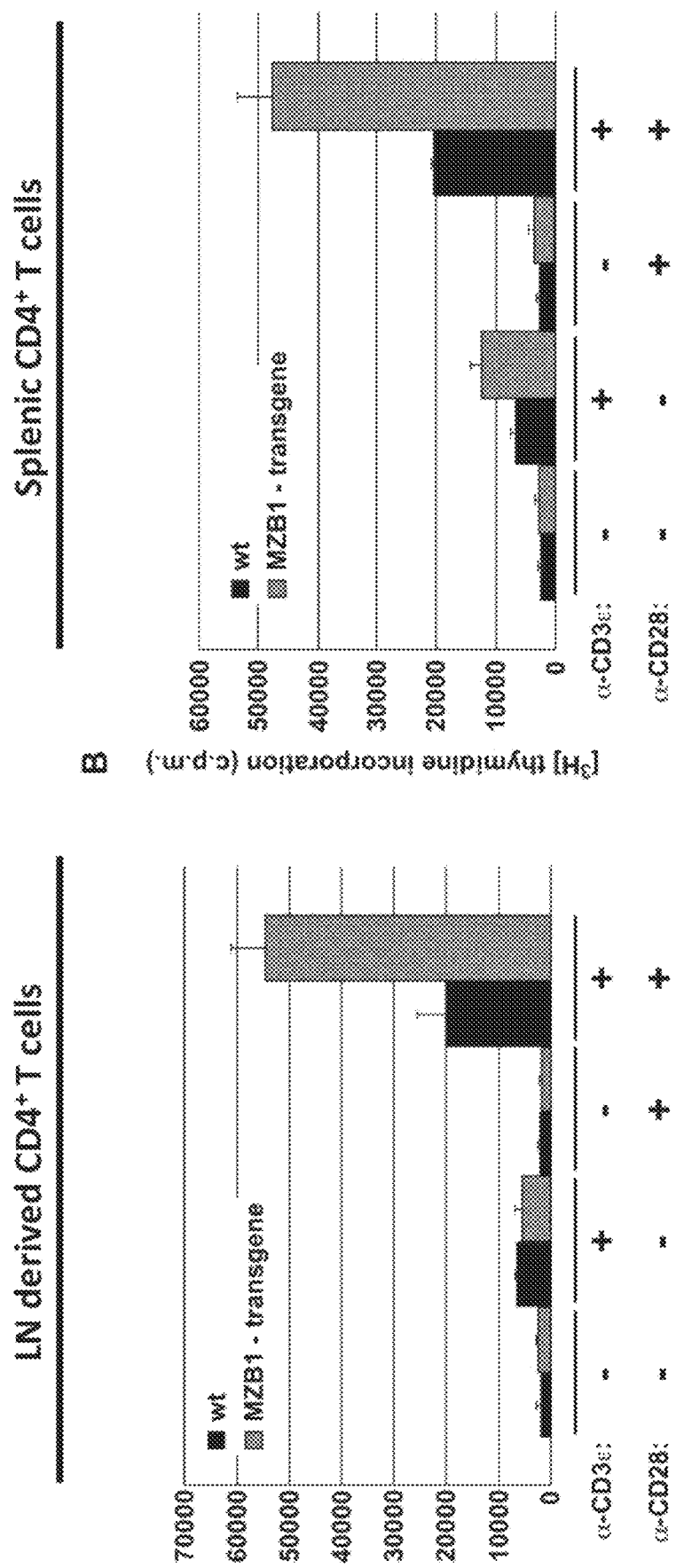

FIG. 47: Measurement of [$^{3}$H]thymidine incorporation in CD4⁺ lymph node-derived and in CD4⁺ splenic T cells isolated from transgenic mice and their corresponding wt littermates. LN-derived (A), and splenic (B) FACS-sorted CD4⁺ T cells, either isolated from 5-9 weeks old transgenic mice or their corresponding wt littermates were plated in a 96 well format. Cells were either left untreated or induced with α-CD28 (0.3 µg/ml), α-CD3ε (0.3 µg/ml) or both for 12 hours. Each well was pulsed with 1.5 µCi [$^{3}$H] thymidine 12 h-16 h before being collected. Data are expressed as the mean [$^{3}$H] thymidine incorporation of triplicate cultures. The figure is a representative of three independent experiments.

Figure 48:
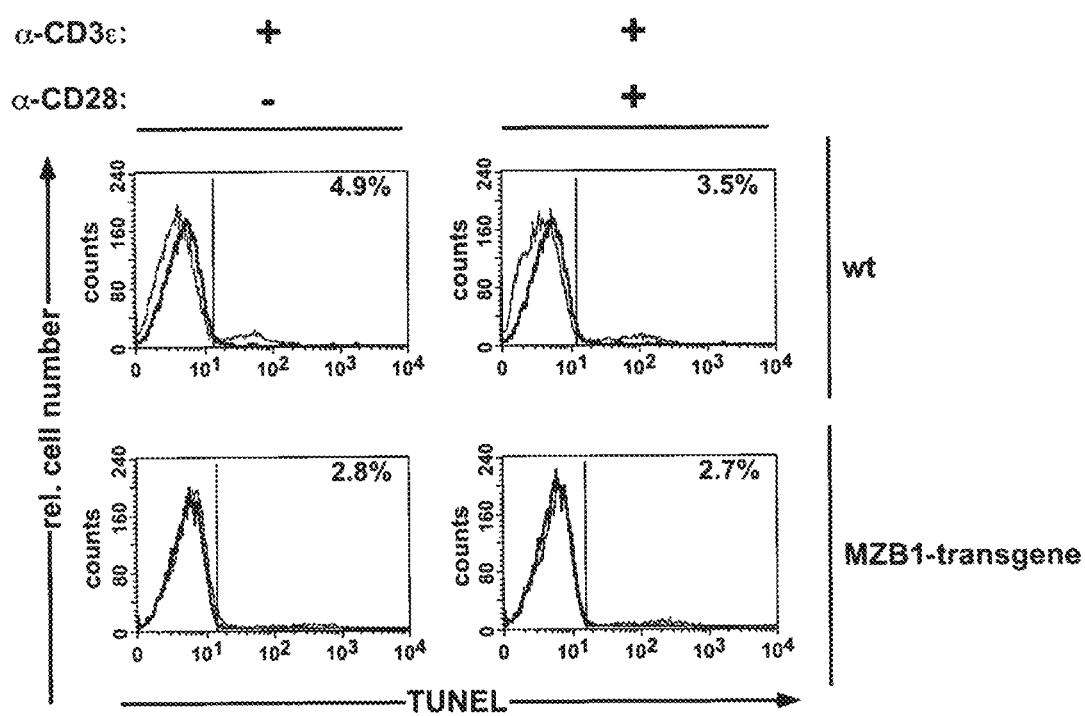

FIG. 48: TUNEL assay on CD4⁺ splenic T cells isolated from transgenic mice and their corresponding wt littermates. FACS-sorted CD4⁺ splenocytes, either isolated from 5-9 weeks old transgenic mice or their corresponding wt littermates were TCR-stimulated with α-CD3ε (0.3 µg/ml) alone, or with both α-CD28 (0.1 µg/ml) and α-CD3ε (0.3 µg/ml) for 24 hours at 37° C. in a 5% $CO_2$-humidified incubator. For determining the apoptotic status, the cells were stained with the "In Situ Cell Death Detection Kit" (Roche) according to the manufacturers instructions and the levels of APC⁺ apoptotic cells were quantified by flow cytometry. Percentages of apoptotic cells staining positive for APC-dUTP are shown. Negative controls are shown in red. The figure is a representative of three independent experiments.

Figure 49:
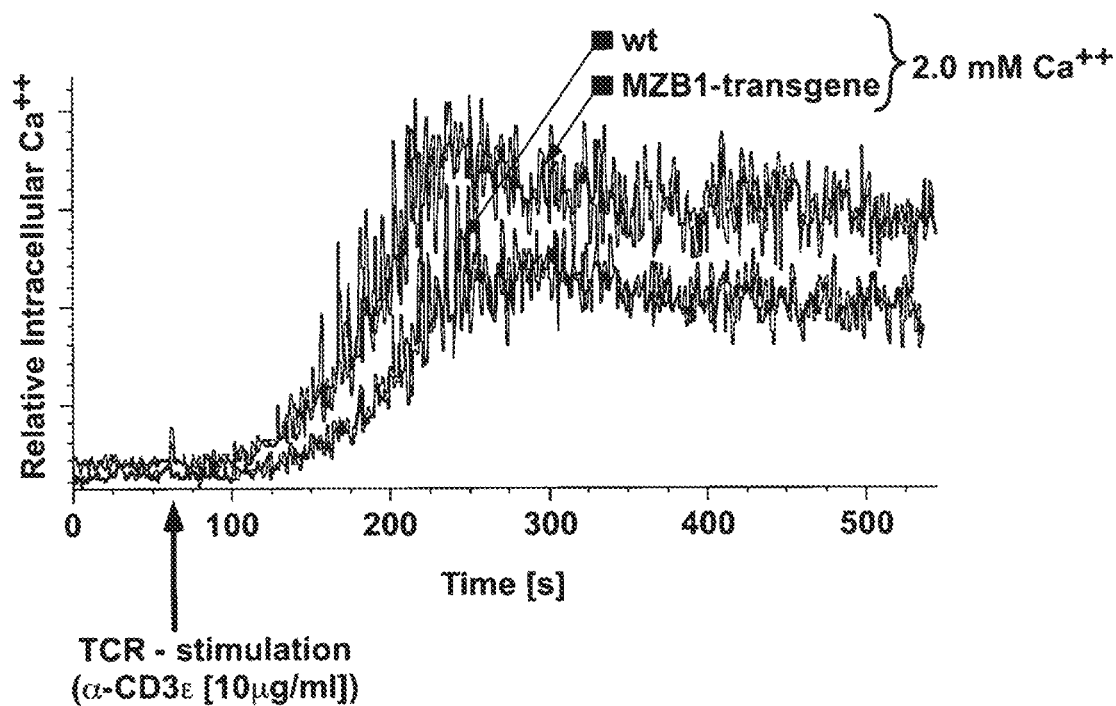

FIG. 49: Calcium responses in CD4⁺ splenic T cells isolated from transgenic mice and their corresponding wt littermates. MACS®-purified CD4⁺ splenocytes, either isolated from 5-9 weeks old transgenic mice or their corresponding wt littermates were TCR-stimulated with α-CD3ε (10.0 µg/ml) and increases in free intracellular $Ca^{2+}$ were measured in real time using a FACSAria flow-cytometer. The $Ca^{2+}$-concentration of the used RPMI-media was 2.0 mM. Data are representative of five independent experiments with similar results.

Figure 50:
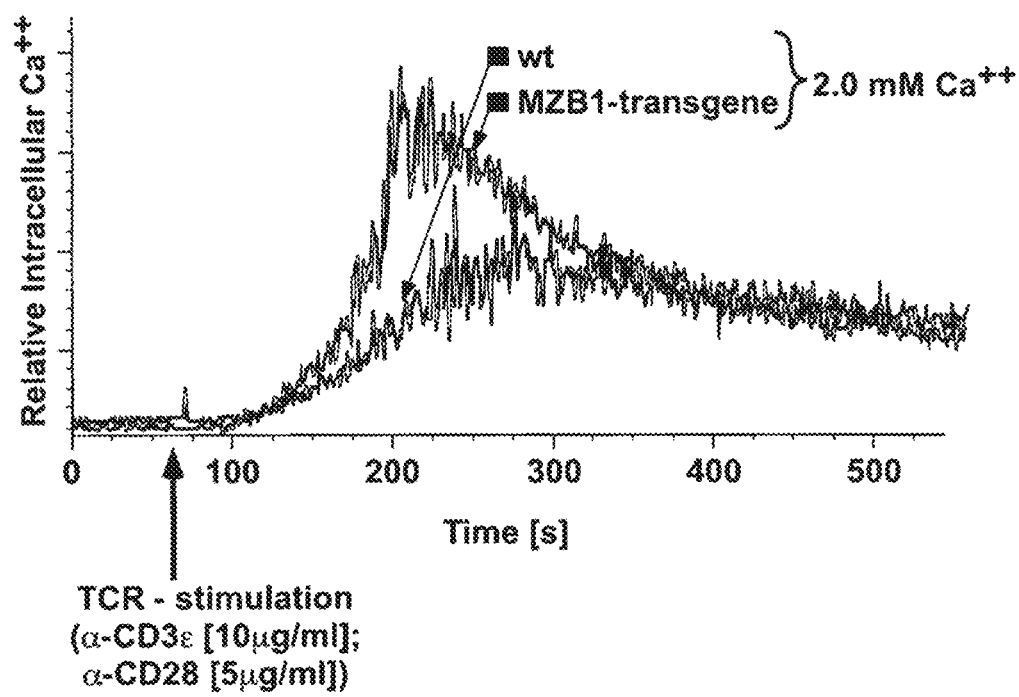

FIG. 50: Calcium responses in CD4⁺ splenic T cells isolated from transgenic mice and their corresponding wt littermates. MACS®-purified CD4⁺ splenocytes, either isolated from 5-9 weeks old transgenic mice or their corresponding wt littermates were stimulated with both α-CD3ε (10.0 µg/ml) and α-CD28 (5.0 µg/ml). Increases in free intracellular $Ca^{2+}$ were measured in real time using a FACSAria flow-cytometer. The $Ca^{2+}$-concentration of the used RPMI-media was 2.0 mM. Data are representative of five independent experiments with similar results.

Figure 51:
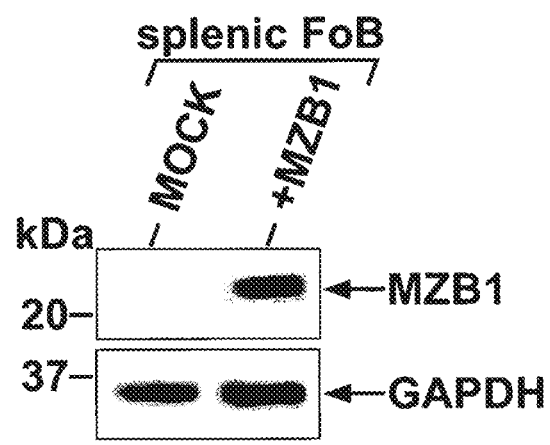

FIG. 51: MZB1 expression in MOCK-transduced and MZB1-transduced Fo B cells. FACS-sorted FO B cells ($B220^+CD21^{int}CD23^{hi}$) were either retrovirally transduced with GFP alone (MOCK) or with MZB1 and GFP (+MZB1). Transduced, $GFP^+$ Fo B cells were enriched by FACS-sorting. An immunoblot analysis with MZB1-specific antibodies (clone 2F9) was performed on 20 mg total protein extracts from splenic FO B cells, infected with the MZB1- and GFP-expressing (+MZB1) or the solely GFP-expressing retrovirus (MOCK). As a control for loading and transfer an additional immunoblot analysis using a GAPDH-specific antibody was performed.

Figure 52:
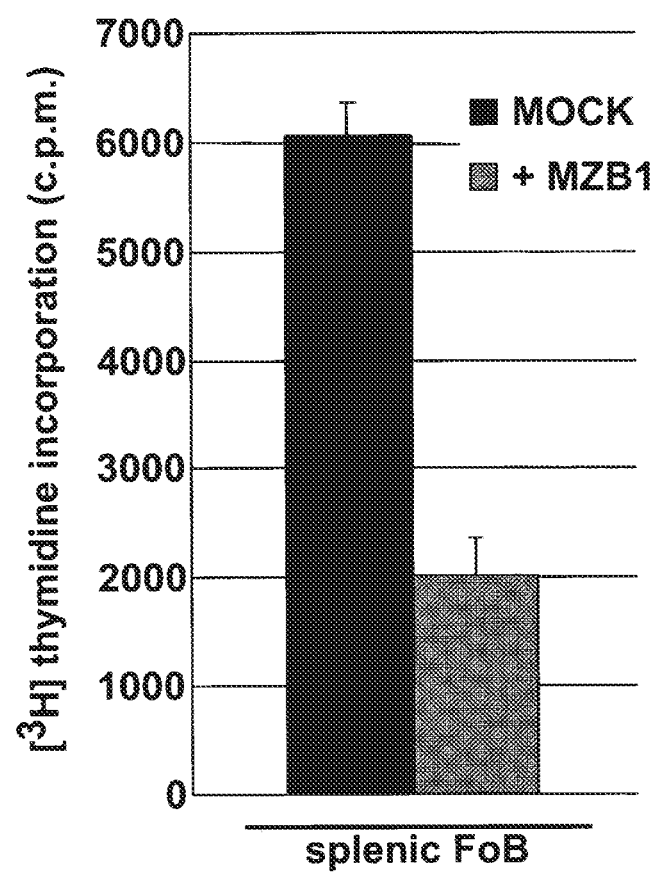

FIG. 52: Measurement of [$^3$H]thymidine incorporation in MOCK-transduced and MZB1-transduced FO B cells. FACS-sorted FO B cells ($B220^+CD21^{int}CD23^{hi}$) were either retrovirally transduced with GFP alone (MOCK) or with MZB1 and GFP (+MZB1). Transduced, $GFP^+$ FO B cells were enriched by FACS-sorting. The infected and FACS-sorted ($GFP^+$) FO B cells were plated in a 96 well format. Each well was pulsed with 1.5 mCi [$^3$H] thymidine 12 h-16 h before being collected. Data are expressed as the mean [$^3$H] thymidine incorporation of triplicate cultures. The figure is a representative of three independent experiments.

DETAILED DESCRIPTION OF THE INVENTION

The present inventors identified a novel gene from mouse B cells, which is expressed at high levels in splenic MZ B cells and peritoneal B1 B cells, but is expressed at very low level or not expressed at all in splenic follicular (FO) B cells. The gene encodes a protein, which has an apparent molecular weight of 21 kD on SDS gel, which the inventors named "MZB1" (marginal zone B1 B cell factor 1). The present inventors found that MZB1 acts as a modulator of the BCR signal transduction cascade in MZ and B1 B cells, possibly via its interaction with RACK1 and PKCβ. Specifically, MZB1 negatively regulates B cell proliferation and tyrosine phosphorylation in the absence of BCR stimulation and calcium mobilization upon BCR stimulation. Furthermore, the present inventors found that MZB1 is a positive regulator of antibody production from B cells, not only MZ and B1 B cells, but also FO B cells, possibly via its interaction with BIP.

As used herein, "a" and "an" refer to not only a single individual, but also a group or species of entities.

All terms used herein bear the meanings that are established in the art unless otherwise noted. All techniques disclosed herein can be performed by a person skilled in the art following established protocols, such as those disclosed in Molecular Cloning: A Laboratory Manual (Sambrook et al., 1989, Cold Spring Harbour Laboratory, New York), Current Protocols in Molecular Biology (Ausubel et al., 2007, John Wiley & Sons, New York), Current Protocols in Immunology (Coligan et al., 2007, John Wiley & Sons, New York), Current Protocols in Protein Science (Coligan et al., 2007, John Wiley & Sons, New York) and Antibodies, a Laboratory Manual (Harlow et al., 1988, Cold Spring Harbour Laboratory, New York).

Nucleic Acid Molecules

The present invention provides an isolated nucleic acid molecule comprising or having a nucleotide sequence encoding a polypeptide having at least one of the biological activities of MZB1.

As used herein, the term "isolated nucleic acid" refers to a nucleic acid that is removed from its natural environment such as genomic DNA and that is free from at least one contaminating nucleic acid, protein or other substances with which it is naturally associated, and preferably substantially free from any contaminating nucleic acid, protein or other substances which would interfere with its use in protein production or other uses.

As disclosed herein, MZB1 positively regulates antibody production, negatively regulates proliferation and tyrosine phosphorylation in the absence of BCR stimulation and $Ca^{2+}$ mobilization in the presence of BCR stimulation in a B cell, such as a MZ B cell, a B1 B cell and a FO B cell, In a preferred embodiment, MZB1 is encoded by the nucleotide sequence of SEQ ID NO:1, 3, 11, 12 or 13, or a nucleotide sequence encoding a polypeptide having the amino acid sequence of SEQ ID NO: 2 or 4, orthologs, allelic variants, or splice variants thereof. A nucleic acid molecule comprising or having any of the above-mentioned nucleotide sequence is hereafter referred to "an MZB1 nucleic acid molecule".

An ortholog refers to a gene in a different species that has evolved from a common ancestor as the gene comprising the nucleotide sequence of SEQ ID NO:1 or 3 or the nucleotide sequence encoding a polypeptide having the amino acid sequence of SEQ ID NO: 2 or 4.

An allelic variant refers one of several possible naturally occurring alternate forms of the gene comprising the nucleotide sequence of SEQ ID NO:1 or 3 or the nucleotide sequence encoding a polypeptide having the amino acid sequence of SEQ ID NO: 2 or 4 which occupy a given locus on a chromosome of an organism or a population of organisms.

A splice variant refers an mRNA which is generated by alternative splicing of an RNA transcript from the gene comprising the nucleotide sequence of SEQ ID NO:1 or 3 or the nucleotide sequence encoding a polypeptide having the amino acid sequence of SEQ ID NO: 2 or 4.

In another preferred embodiment, MZB1 has the amino acid sequence of SEQ ID NO:2 or 4. In yet another preferred embodiment, MZB1 has the amino acid sequence of SEQ ID NO:2 or 4 further comprising an amino-terminal methionine.

The amino acid sequence of SEQ ID NO:2, encoded by the nucleotide sequence of SEQ ID NO:1, represents the sequence of full length MZB1 including the signal peptide. The amino acid sequence of SEQ ID NO:4, encoded by the nucleotide sequence of SEQ ID NO:3, represents the sequence of mature MZB1 lacking the signal peptide.

The isolated nucleic acid molecule of the present invention includes a MZB1 nucleic acid molecule which comprises or has a nucleotide sequence selected from the group consisting of:

(a) a nucleotide sequence as set forth in SEQ ID NO:1, 3, 11, 12 or 13, (b) a nucleotide sequence encoding the polypeptide having an amino acid sequence as set forth in SEQ ID NO:2 or 4, (c) a nucleotide sequence encoding a polypeptide having the amino acid sequence as set forth in SEQ ID NO:2 or 4 further comprising an amino-terminal methionine, (d) a nucleotide sequence that is an ortholog of any of (a)-(c), (e) a nucleotide sequence that is an allelic variant or a splice variant of any of (a)-(d).

The isolated nucleic acid molecule of the present invention also includes a variant of the MZB1 nucleic acid molecules described above.

In one embodiment, the variant comprises or has a nucleotide sequence that is at least 50%, 60%, 70%, 80%, 85%, preferably at least 90%, 91%, 92%, 93%, 94%, more preferably at least 95%, 96%, 97%, 98%, even more preferably at least 99% identical to the nucleotide sequence of any of (a)-(e) above, in particular, (a)-(c) above, over its entire length.

In another embodiment, the variant comprises or has a nucleotide sequence encoding a polypeptide that has at least 72%, 75%, 80%, 85%, preferably at least 90%, 91%, 92%, 93%, 94%, more preferably at least 95%, 96%, 97%, 98%, even more preferably at least 99% amino acid sequence identity or similarity to the polypeptide as set forth in SEQ ID NO:2 or 4, orthologs, allelic variants or splice variants thereof over its entire length.

The term "identity" has well-established meaning in the art and refers to the percent of identical matches between two or more sequences with gap alignments addressed by a particular mathematical model of computer programs (i.e., "algorithms").

The term "similarity" has well-established meaning in the art and refers to a measure of similarity which includes both identical matches and conservative substitution matches between two or more sequences with gap alignments addressed by a particular mathematical model of computer programs (i.e., "algorithms"). Since conservative substitutions apply to polypeptides and not nucleic acid molecules, similarity only deals with polypeptide sequence comparisons.

The term "conservative amino acid substitution" has well-established meaning in the art and refers to a substitution of a native amino acid residue with a non-native residue such that there is little or no effect on the size, polarity or charge of the amino acid residue at that position. A person skilled in the art knows which amino acid substitutions are conservative and which are not.

Identity and similarity between nucleic acid molecules and polypeptides can be readily calculated by known methods. Preferred methods to determine identity and/or similarity are designed to give the largest match between the sequences tested. Methods for determining identity and similarity are codified in publicly available computer programs.

Preferably, the degree of sequence identity and/or similarity between two sequences is determined by the BLAST 2 SEQUENCES publicly available on the NCBI website (http://www.ncbi.nlm.nih.gov/blast/bl2seq/wblast2.cgi) using the default setting. The algorithm employed is based on Tatiana A, et al. (1999).

The default setting of version BLASTN 2.2.17 (updated Aug. 26, 2007) for comparing two nucleotide sequences includes:
 reward for match: 1
 penalty for a mismatch: 2
 penalty for open gap: 5
 penalty for gap extension: 2

The default setting of version BLASTP2.2.17 (updated Aug. 26, 2007) for comparing two amino acid sequences includes:
 matrix: BLOSUM62
 penalty for open gap: 11
 penalty for gap extension: 1

The term "over its entire length" means that the degree of identity and similarity is expressed as a percentage of the number of identical or identical plus similar residues over the total number of residues of the reference sequence. Therefore, "sequence B is 50% identical to sequence A over its entire length" means that "sequence B is 50% identical to sequence A over the entire length of sequence A". Similarly, "sequence B has 50% identity (or similarity) to sequence A over its entire length" means that "sequence B has 50% sequence identity (or similarity) over the entire length of sequence A". For example, if sequence A has 100 residues, sequence B has 75 residues, sequence A and B have 50 identical residues in an overlap of 60 residues, then sequence B is 50/100=50% identical to sequence A.

In yet another embodiment, the variant comprises or has a nucleotide sequence which hybridizes under highly stringent or moderately stringent conditions to the nucleotide sequence of any of (a)-(e) above, in particular, (a)-(c) above, or a complementary sequence thereof.

The conditions of high and moderate stringency are well known to those skilled in the art and can be found in standard protocol books such as Molecular Cloning: A Laboratory Manual (Sambrook et al., supra) and Current Protocols in Molecular Biology (Ausubel et al., supra).

In a further embodiment, the variant comprises or has a nucleotide sequence encoding a polypeptide having the amino acid sequence encoded by a MZB1 nucleic acid molecule, in particular, the amino acid sequence of SEQ ID NO:2 or 4, with at least one modification, preferably 1-150 modification(s), more preferably 1-100 modification(s), even more preferably 1-50 modification(s), most preferably 1-30 modification(s), selected from the group consisting of amino acid substitution, amino acid insertion, amino acid deletion, carboxyl-terminal truncation, and amino-terminal truncation.

In particular, the variant comprises or has a nucleotide sequence encoding a polypeptide having the amino acid sequence encoded by a MZB1 nucleic acid molecule, in particular, the amino acid sequence of SEQ ID NO:2 or 4, with 1, 2, 3, 4, 5, 1-10, 1-15, 1-20 or 1-30 amino acid substitution(s), 1, 2, 3, 4, 5, 1-10, 1-15, 1-20 or 1-30 amino acid insertion(s), 1, 2, 3, 4, 5, 1-10, 1-15, 1-20 or 1-30 amino acid deletion(s), a carboxyl-terminal truncation of 1, 2, 3, 4, 5, 1-10, 1-15, 1-18, 1-20, 1-30, 1-50, 1-100 or 1-150 amino acid(s), an amino-terminal truncation of 1, 2, 3, 4, 5, 1-10, 1-15, 1-18, 1-20, 1-30, 1-50, 1-100 or 1-150 amino acid(s), or any combination thereof.

In certain specific embodiments, the variant comprises or has a nucleotide sequence as set forth in SEQ ID NO: 5, 7 or 9. In other specific embodiments, the variant comprises or has a nucleotide sequence encoding a polypeptide having an amino acid sequence as set forth in SEQ ID NO: 6, 8 or 10.

The term "amino acid substitution" refers to both conservative and non-conservative amino acid substitutions. Amino acid substitution also encompasses substitution with non-naturally occurring amino acid residues such as those typically incorporated by chemical peptide synthesis. Non-naturally occurring amino acid residues include peptidomimetics, and other reversed or inverted forms of amino acid moieties.

In one special embodiment, the variant encodes a dominant-negative variant of MZB1 which inhibits at least one of the biological activities of MZB1.

The present invention also provides a fragment of a MZB1 nucleic acid molecule or a variant thereof described above.

In one embodiment, the fragment comprises or contains at least 12, 15, 18, 19, 20, 21, 22, 23, 24, 25, 26, 30, 45, 60, 75, 90, 120, 150, 180, 210, 240, 270, 300, 360, 450, or 540 consecutive nucleotides of a MZB1 nucleic acid molecule or a variant thereof, in particular, a nucleic acid molecule comprising or having the nucleotide sequence of SEQ ID NO:1 or 2 or encoding the amino acid sequence of SEQ ID NO:2 or 4.

In another embodiment, the fragment comprises or has a nucleotide sequence encoding a polypeptide of at least 4, 5, 10, 15, 20, 25, 30, 40, 50, 60, 70, 80, 90, 100, 120, 150, or 180 consecutive amino acid residues of any of the polypeptides encoded by a MZB1 nucleic acid molecule or a variant thereof, in particular, a polypeptide encoded by the nucleotide sequence of SEQ ID NO:1 or 2 or having the amino acid sequence of SEQ ID NO:2 or 4.

The nucleic acid fragment of the present invention may encode a peptide or polypeptide which has at least one of the biological activities of MZB1. The nucleic acid fragment of the present invention may encode a peptide or polypeptide which is useful as a research tool, such as an immunogen, or a bait for interaction partner(s). The nucleic acid fragment of the present invention may be used in the detection or modulation (i.e., increase or decrease) of expression of a MZB1 nucleic acid molecule or a variant thereof.

The present invention further provides a nucleic acid molecule comprising or having a nucleotide sequence that is complementary to the nucleotide sequence of any of the nucleic acid molecules described above.

The degree of complementarity is preferably at least 50%, 60%, 70%, more preferably at least 75%, 80%, 85%, 90%, even more preferably at least 95%, 96%, 97%, 98%, 99%, and most preferably 100%.

As used in the art, the term "degree of complementarity" between two oligonucleotides or polynucleotides refers to the percentage of complementary bases in the overlapping region of the two oligonucleotides or polynucleotides. Two bases are complementary to each other if they can form a base pair via hydrogen bonding. Base pairs include both Waston-Crick base pairs (A-T, C-G, A-U) and wobble base pairs (G-U, I-U, I-A, I-C). The degree of complementarily can be determined by a skilled person using any known methods in the art. For example, ATCG has 100% complementarity to CGAT and CGATGG, and 75% complementarity to CGTT and CGTTGG.

In one embodiment, the complementary nucleic acid molecule is at least 12, 15, 18, 19, 20, 21, 22, 23, 24, 25, 26, 40 or 50 nucleotides in length.

In another embodiment, the complementary nucleic acid comprises one or more stretches of non-complementary sequence(s).

The complementary nucleic acid molecule may be used in the detection or modulation (i.e., increase or decrease) of expression of a MZB1 nucleic acid molecule or a variant thereof.

In a preferred embodiment, the complementary nucleic acid molecule is capable of downregulating the expression of a polypeptide encoded by a MZB1 nucleic acid molecule, a variant or a fragment thereof.

In certain embodiments, the complementary nucleic acid molecule is an antisense RNA, an siRNA, an shRNA, a miRNA, or a ribozyme. A person skilled in the art knows very well the meaning of the above terms and the structural requirements and the functions of the above entities.

The present invention additionally provides a nucleic acid molecule which encodes a fusion polypeptide comprising a MZB1 polypeptide, a variant or a fragment thereof as described below fused to a heterologous amino acid sequence.

The isolated nucleic acid molecule of the present invention may be single-stranded, single-stranded with a hairpin structure, double-stranded, or partially double-stranded.

The isolated nucleic acid molecule of the present invention may be DNA, RNA, or chimeric or hybrid DNA-RNA. The nucleic acid of the present invention may contain naturally occurring nucleotides, modified nucleotides, or any of the known base analogs of DNA and RNA. Furthermore, the nucleic acid of the present invention may be modified covalently or non-covalently.

In a preferred embodiment, the nucleic acid of the present invention, in particular, an RNA, is modified to have enhanced chemical stability and/or nuclease resistance. Exemplary modifications include the introduction of phosphorothioate linkage(s) and/or pyrophosphate linkage(s).

The isolated nucleic acid molecules of the present invention can be obtained by a person skilled in the art using techniques established in the art, such as library screening, PCR amplification, in vitro transcription, and chemical synthesis.

The isolated nucleic acid molecules of the present invention may be used to modulate (i.e., increase or decrease) the expression level of the encoded polypeptide in a cell or an organism which expresses the polypeptide endogenously or a host cell or a host organism which expresses the polypeptide exogenously. The isolated nucleic acid molecules of the present invention may also be used in detection and diagnosis.

Polypeptides

The present invention provides an isolated polypeptide having at least one of the biological activities of MZB1.

The term "isolated polypeptide" refers to a polypeptide this is removed from its natural environment such as a cell and that is free from at least one contaminating polypeptide or other contaminating substance that is found in its natural environment, and preferably substantially free from any contaminating polypeptides and contaminating substances which would interfere with its use.

The isolated polypeptide of the present invention includes a MZB1 polypeptide which comprises or has the amino acid sequence of SEQ ID NO:2 or 4 or the amino acid sequence of SEQ ID NO:2 or 4 further comprising an amino-terminal methionine, an ortholog, allelic variant or splice variant thereof, or which is encoded by a MZB1 nucleic acid of the present invention.

The polypeptide of the present invention also includes a variant of a MZB1 polypeptide.

In one embodiment, the variant is encoded by a nucleotide sequence that is at least 50%, 60%, 70%, 80%, 85%, preferably at least 90%, 91%, 92%, 93%, 94%, more preferably at least 95%, 96%, 97%, 98%, even more preferably at least 99% identical to the nucleotide sequence of a MZB1 nucleic acid molecule, in particular, the nucleotide sequence of SEQ ID NO:1 or 3, over its entire length.

In another embodiment, the variant has at least 72%, 75%, 80%, 85%, preferably at least 90%, 91%, 92%, 93%, 94%, more preferably at least 95%, 96%, 97%, 98%, even more preferably at least 99% amino acid sequence identity or similarity to a MZB1 polypeptide, in particular, the polypeptide comprising or having the amino acid sequence of SEQ ID NO:2 or 4 over its entire length, optionally further comprising an amino-terminal methionine.

In a further embodiment, the variant is encoded by a nucleic acid comprising or having a nucleotide sequence which hybridizes under highly stringent or moderately stringent conditions to a MZB1 nucleic acid molecule or a complementary molecule thereof, in particular, the nucleotide sequence as set forth in SEQ ID NO:1 or 3, optionally further comprising an amino-terminal methionine.

In a still further embodiment, the variant comprises or has an amino acid sequence of a MZB1 polypeptide, in particular, the amino acid sequence as set forth in SEQ ID NO:2 or 4, with at least one modification, preferably 1-150 modification(s), more preferably 1-100 modification(s), even more preferably 1-50 modification(s), most preferably 1-30 modification(s) selected from the group consisting of amino acid substitution, amino acid insertion, amino acid deletion, carboxyl-terminal truncation, and amino-terminal truncation, optionally further comprising an amino-terminal methionine, In particular, the variant comprises or has an amino acid sequence of a MZB1 polypeptide, in particular, the amino acid sequence as set forth in SEQ ID NO:2, with 1, 2, 3, 4, 5, 1-10, 1-15, 1-20 or 1-30 amino acid substitution(s), 1, 2, 3, 4, 5, 1-10, 1-15, 1-20 or 1-30 amino acid insertion(s), 1, 2, 3, 4, 5, 1-10, 1-15, 1-20 or 1-30 amino acid deletion(s), a carboxyl-terminal truncation of 1, 2, 3, 4, 5, 1-10, 1-15, 1-18, 1-20, 1-30, 1-50, 1-100 or 1-150 amino acid(s), an amino-terminal truncation of 1, 2, 3, 4, 5, 1-10, 1-15, 1-18, 1-20, 1-30, 1-50, 1-100 or 1-150 amino acid(s), or any combination thereof, optionally further comprising an amino-terminal methionine.

In certain specific embodiments, the variant is encoded by a nucleotide sequence as set forth in SEQ ID NO; 5, 7 or 9. In other specific embodiments, the variant comprises or has an amino acid sequence as set forth in SEQ ID NO: 6, 8 or 10.

In one special embodiment, the variant is a dominant-negative variant of MZB1 which inhibits at least one of the biological activities of MZB1.

The present invention also provides a fragment of a MZB1 polypeptide or a variant thereof described above.

In one embodiment, the fragment is encoded by a nucleic acid molecule comprising or having at least 12, 15, 18, 21, 24, 30, 45, 60, 75, 90, 120, 150, 180, 210, 240, 270, 300, 360, 450, 540 consecutive nucleotides of a nucleic acid molecule of the present invention, preferably, the nucleic acid molecule having the nucleotide sequence as set forth in SEQ ID NO:1 or 3, optionally further comprising an amino-terminal methionine.

In another embodiment, the fragment comprises or consists of at least 5, 10, 15, 20, 25, 30, 40, 50, 60, 70, 80, 90, 100, 120, 150, or 180 consecutive amino acid residues of a MZB1 polypeptide or a variant thereof, preferably, the polypeptide comprising or having the amino acid sequence of SEQ ID NO:2 or 4, optionally further comprising an N-terminal methionine.

The peptide or polypeptide fragment may have at least one of the biological activities of MZB1. The peptide or polypeptide fragment may be useful as a research tool, such as an immunogen, or a bait for interaction partner(s).

The present invention further provides a fusion polypeptide comprising a MZB1 polypeptide, a variant or a fragment thereof described above fused to a heterologous amino acid sequence.

The heterologous amino acid sequence may be an epitope tag which may be useful in the purification and/or the detection of the fusion polypeptide. Commonly used epitope tags include, but are not limited to, His tag (poly-His or hexa-His), Myc tag, FLAG tag, and HA tag.

The heterologous amino acid sequence may be Fc domain of an immunoglobulin (i.e., antibody) molecule or any other sequence which may be useful in the purification and the detection of the fusion polypeptide.

The heterologous amino acid sequence may be sequences that are involved in the dimerization or multimerization of the fusion protein, including, but not limited to, the leucine zipper sequences and the Fc domain of an antibody.

The heterologous amino acid sequences may also be sequences that are capable of targeting the fusion protein to particular tissues, cells, subcellular compartments, or facilitating the transport of the fusion protein across the cell membrane.

The polypeptide of the present invention may be chemically modified, for example, by covalent attachment of one or more polymers. The modification may alter the biological activity, chemical stability, bioavailability, biodistribution, pharmacokinetic properties of the polypeptide.

The polypeptide of the present invention may be obtained from naturally occurring cells, such as MZ B cells and B1 B cells, which express the polypeptide endogenously, or host cells, host organisms, or parts of host organisms which express the polypeptide exogenously.

Polypeptides, in particular, fragments of the present invention may also be prepared by chemical synthesis methods (such as solid phase peptide synthesis) using techniques known in the art. The polypeptide may be synthesized with or without a methionine at the amino terminus.

The polypeptides of the present invention may be used as a research tool, for example, to identify interaction partners. The polypeptide of the present invention may be used to screen for compounds which modulate (i.e., increase or decrease) at least one of the biological activities of MZB1. The polypeptide of the present invention may also be used as an immunogen for generating specific antibodies.

TABLE 1

MZB1 and selected variants and fragments.

| | SEQ ID NO: | |
|---|---|---|
| | nucleotide sequence | amino acid sequence |
| MZB1 polypeptide | | |
| full length (aa1-188) | 1 | 2 |
| mature (aa19-188) | 3 | 4 |
| full length without REEL (aa1-184) | 5 | 6 |
| mature without REEL (aa19-184) | 7 | 8 |
| fragment (aa46-179) | 9 | 10 |
| MZB1 nucleic acid | | |
| full length with 5' and 3' UTR | 11 | |
| full length with 5' UTR | 12 | |
| full length with 3' UTR | 13 | |

Vectors

The present invention provides a vector comprising a nucleic acid molecule of the present invention, operably linked to transcription regulatory sequences.

In one embodiment, the transcription regulatory sequences are heterologous transcription regulatory sequences which are different from the native transcription regulatory sequences for the MZB1 polypeptide.

The term "transcription regulatory sequences" refers to elements that are involved in the regulation (positive or negative) of transcription, including but not limited to, promoters and enhancers.

The term "operably linked" refers to an arrangement which allows for the transcription and/or transcription and translation of the nucleic acid molecule of the present invention.

Elements which are necessary for the maintenance, replication and selection of the vector, and the transcription and/or translation of the inserted nucleic acid sequence are well known in the art. Furthermore, elements which may enhance the transcription and/or translation of the inserted nucleic acid sequence are also well known in the art.

In one embodiment, the expression from the expression vector is constitutive in a host cell, or constitutive and/or ubiquitous in a host organism. In another embodiment, the expression from the expression vector is inducible in the host cell or host organism. In yet another embodiment, the expression from the expression vector is cell-, cell type-, cell lineage-, tissue-specific or developmental stage-specific in the host organism.

The vector of the present invention allows for the transcription and/or transcription and translation of the nucleic acid of the present invention. The vector of the present invention may be used to modulate (i.e., increase or decrease) the expression level of a polypeptide of the present invention in a cell or an organism which expresses the polypeptide endogenously or in a host cell or a host organism which expresses the polypeptide exogenously.

A person skilled in the art can select an appropriate vector on the basis of the host cell or host organism to be used and the purpose of the transcription of the nucleic acid of the present invention.

Host Cells

The present invention provides a host cell comprising a nucleic acid or a vector of the present invention.

The nucleic acid or the vector may exist extra-chromosomally or may be integrated into the genome of the host cell.

The host cell of the present invention may be a prokaryotic cell or a eukaryotic cell. Prokaryotic host cells include, but are not limited to, bacterial cells such as various strains of *E. coli, B. subtilis, Pseudomonas* spp., *Bacillus* spp., *Streptomyces* spp. Eukaryotic host cells include, but are not limited to, yeast, plant cells, invertebrate cells and vertebrate cells. Invertebrate cells include insect cells; vertebrate cells include mammalian cells. Preferred yeast cells include, but are not limited to, *Saccharomyces cerivisae, Schizosaccharomyces pombe*, and *piccia*. Preferred mammalian cells include, but are not limited to, CHO, COS, 3T3, HeLa, 293, K46, EL4, WEHI231, WEHI279, BJAB, Raji, J558 L, IL-7-dependent pre-B cells, hybridoma and myeloma cells.

A host cell of the present invention may be obtained by introducing a vector of the present invention into a host cell via any of the methods well known in the art, including, but not limited to, transformation (e.g., heat shock, electroporation), transfection (e.g., calcium phosphate precipitation, electroporation, lipofection, the DEAE-dextran method), infection or transduction (e.g., by bacteriophage or viruses), and microinjection. The method will at least in part depend on the type of host cell to be used.

In certain embodiments, the nucleic acid of the present invention contains codons which have been altered for optimal expression in a given host cell.

The host cell of the present invention may be used to the produce a polypeptide of the present invention. Certain appropriate host cells may also be used for producing antibodies.

Host Organisms

The present invention provides a host organism comprising a nucleic acid or a vector of the present invention.

In a perferred embodiment, the nucleic acid or the vector is stably integrated into the genome of the host organism. In other words, the host organism of the present invention is a transgenic organism.

As used herein, the term "organism" refers to a multicellular organism. The host organism of the present invention is preferably a vetebrate animal. In one embodiment, the host organism is a laboratory animal, including but not limited to, mouse, rat, guinea pig, hamster, rabbit, dog, monkey, chimpanzee. In another embodiment, the host organism is a farm animal, including but not limited to, cow, ox, sheep, goat, horse, pig. In yet another embodiment, the host animal is a non-human mammal, such as a rodent or a non-human primate. In a preferred embodiment, the organism is mouse.

Since the nucleic acid and the vector of the present application may increase or decrease the expression of a polypeptide of the invention, the transgenic organism of the present invention may have increased or decreased expression of the polypeptide of the present invention compared to a non-transgenic counterpart.

The expression from the nucleic acid or the vector of the present application in the host organism may be constitutive, ubiquitous, inducible, and/or cell-, cell type-, cell lineage-, tissue-specific or developmental stage-specific.

The host organism of the present invention may be used as a research tool for studying the biology of MZB1 using gain-of-function or loss-of-function approaches.

In a specific embodiment, the host organism of the present invention is a BAC (bacterial artificial chromosome) transgenic animal. The BAC transgenic animal carries a transgene construct which comprises a BAC which contains the complete MZB1 genomic locus with all regulatory sequences. The coding sequence of MZB1 in the transgenic construct may be substituted by the coding sequence of a MZB1 variant or a reporter protein (such as GFP). The MZB1 variant may be a polypeptide encoded by the nucleotide sequence of SEQ ID NO: 3, 5, 7 or 9, or a polypeptide having the amino acid sequence of SEQ ID NO: 4, 6, 8, or 10.

Knock-Out and Knock-in Organisms

The present invention provides a knock-out or a conditional knock-out organism in which the endogenous gene encoding MZB1 is inactivated or conditionally inactivated.

The present invention also provides a knock-in organism wherein an exogenous gene, such as a reporter gene (e.g., GFP), is introduced into the mzb1 genetic locus via homologous recombination. The timing and pattern of expression of the exogenous gene reflects that of endogenous MZB1.

Methods for generating knock-out, conditional knock-out, or knock-in organism are well known in the art.

The preferred organism is a vetebrate animal, in particular, a non-human mammal. More preferably, the organism is a laboratory animal or a farm animal. Mostly preferably, the organism is a rodent, in particular, a mouse.

The knock-out and conditional knock-out organism may be used to study the biological functions of MZB1 and to test the effectiveness of agents which promotes or decreases MZB1 expression and/or activity. The knock-in organism may be used to study the regulation of MZB1 expression.

Antibodies

The present invention provides an antibody or a fragment thereof that specifically binds to a polypeptide of the present invention.

The antibody of the present invention may be polyclonal or monoclonal. The antibody of the present invention may be a chimeric antibody, a humanized antibody or a fully human antibody. The antibody of the present invention may be a single chain antibody. The antibody of the present invention may be bi-specific.

The antibody fragment of the present invention may be an Fab fragment, an Fab' fragment, an F(ab')$_2$ fragment, an Fv fragment, or any other fragment which retains the antigen binding specificity of the intact antibody.

In a preferred embodiment, the antibody of the present invention is a neutralizing or antagonist antibody which inhibits at least one of the biological activities of MZB1 upon binding MZB1.

Whether an antibody inhibits at least one of the biological activities of MZB1 can be readily determined by functional assays, such as Ca$^{2+}$ mobilization assay, cell proliferation assay, and tyrosine phosphorylation assay described in the Examples.

In one embodiment, the neutralizing or antagonistic antibody interferes with the interaction between MZB1 and at least one of its interaction partners, such as RACK1, PKCβ, and BiP. In a specific embodiment, the antibody interferes with the interaction between MZB1 and RACK1. In a particular embodiment, the antibody is 2F9 which interferes with the interaction between MZB1 and RACK1.

Whether an antibody interferes with the interaction between MZB1 and one or more of its interaction partners can be readily determined by assays well-known in the art, such as co-immunoprecipitation, FRET, gel filtration.

In another preferred embodiment, the antibody of the present invention is an agnostic antibody which activates or enhances at least one of the biological activities of MZB1 upon binding MZB1. Whether an antibody activates or enhances at least one of the biological activities of MZB1 can be readily determined by functional assays, such as Ca$^{2+}$ mobilization assay, cell proliferation assay, and tyrosine phosphorylation assay described in the Examples.

In yet another preferred embodiment, the antibody of the present invention is an intracellular antibody, i.e., an intrabody.

In one embodiment, the intrabody is a single-chain Fv fragment (scFv) which contains the heavy and the light chain variable region of an antibody linked by a flexible linker. scFv is expressed intracellularly and bind its intracellular target. scFv may inhibit the function of a target protein by directly inhibiting an enzymatic activity, inhibiting protein-protein interaction, or interfering with the post-translational modification or the transport of the target protein. The fusion of an intracellular localization signal, such as a nuclear localization signal (NLS) or an endoplasmic reticulum retention signal, to the scFv allows for the targeting of the scFv to a specific subcellular compartment.

In another embodiment, the intrabody is an antibody or an antigen-binding fragment hereof fused to an internalization signal, such as that found in HIV TAT.

The present invention also provides an isolated nucleic acid molecule which encodes an antibody of the present invention, and a hybridoma or a host cell that produces an antibody of the present invention.

The antibody and the antigen-binding fragment thereof, their coding sequence, the hybridoma and the host cell of the present invention can be obtained by well-established methods in the art, such as those described in the Current Protocols in Immunology (Coligan et al., supra) and Antibodies, a Laboratory Manual (Harlow et al., supra).

The antibody and the antigen-binding fragment thereof of the present nvention may be used for the purification, detection and quantification of a polypeptide of the present invention. Furthermore, the antibody and the antigen-binding fragment thereof of the present invention may be used for studying and/or modulating (i.e., increase or decrease) the biological activities of the polypeptides of the present invention for research and clinical purposes.

Inhibitors of MZB1 Expression or Activity

The present invention provides a substance that inhibits the expression of MZB1. The present invention also provides a substance that inhibits at least one of the biological activities of MZB1.

Inhibitors of the expression of MZB1 include, but are not limited to, antisense RNA, RNA olignucleotides that are active in RNA interference (RNAi) such as siRNA, shRNA and miRNA, ribozyme, RNA and DNA aptamers, and decoy RNAs.

Given the coding sequence for MZB1, a person skilled in art can design and/or obtain antisense RNA, siRNA, shRNA, miRNA, decoy RNA, DNA and RNA aptamers using methods known in the art. For example, siRNA and shRNA may be designed using publicly available algorithms such as that disclosed in Reynolds et al, (2004) and design engines such as "BD-RNAi design" (Beckton Dickinson) and "Block-iT RNAi" (Invitrogen). Furthermore, a person skilled in the art can test the efficacy of these agents in inhibiting MZB1 expression using methods known in the art such as Northern blot analysis, quantitative or semi-quantitative RT-PCR, Western blot analysis, surface or intracellular FACS analysis.

In one embodiment, the inhibitor of MZB1 expression is an RNA oligonucleotide which is active in RNAi, such as an siRNA, shRNA and miRNA, and which targets GCGAAAGCAGAGGCTAAAT (SEQ ID NO:14), GCAGTCCTATGGAGTTCAT (SEQ ID NO: 15) CCAGATCTATGAAGCCTAC (SEQ ID NO:16), or CTGCCACTGTTGCTACTGT (SEQ ID NO:17) within the MZB1 coding region. In certain embodiments, the inhibitor of MZB1 expression is an siRNA. In certain other embodiments, the inhibitor of MZB1 expression is an shRNA, in particular, an shRNA comprising the nucleotide sequence of GCG-AAAGCAGAGGCUAAAUUUCAAGAGAAUUUAGC-CUCUGCUUUCGC (SEQ ID NO: 18), GCAGUCCUA-UGGAGUUCAUUUCAAGAGAAUGAACUCCAUAG-GACUGC (SEQ ID NO: 19), CCAGAUCUAUGAAGC-CUACUUCAAGAGAGUAGGCUUCAUAGAUCUGG (SEQ ID NO: 20), and CUGCCACUGUUGCUACU-GUUUCAAGAGAACAGUAGCAACAGUGGCAG (SEQ ID NO: 21) (the bold letters denotes the loop sequence and the normal letters denote the loop sequence).

Inhibitors of the activity of MZB1 include, but are not limited to, neutralizing antibodies, in particular, neutralizing intrabodies, RNA aptamer, DNA aptamers, peptide aptamers, small molecule inhibitors, a dominant-negative MZB1, and a dominant-negative interaction partner.

Given the coding sequence of MZB1, a person skilled in the art can express and obtain the MZB1 protein using methods known in the art. Furthermore, a person skilled in the art can screen for agents which inhibit at least one of the activities of MZB1 using either cell-based or cell-free functional assays, such as Ca$^{2+}$ mobilization assay, cell proliferation assay, tyrosine phosphorylation assay, antibody secretion assay described in the Examples.

For example, a person skilled in the art can contact MZB1-expressing and MZB1-deficient cells with a candidate agent, subject the cells to one or more functional assays, and identify candidate agents which negatively affect at least one of the activities of MZB1 in MZB1-expressing but not MZB1-deficient cells. The MZB1-expressing and MZB1-deficient cells should be identical or essentially identical to each other except the expression of MZB1.

In one example, the MZB1-deficient cells do not express any endogenous MZB1; the MZB1-expressing cells are their genetically modified counterparts which express exogenous MZB1. In one specific example, the MZB1-expressing cells are MZB1-deficient cells transfected or transduced in vitro with an MZB1 expression vetor. In another specific example, the MZB1-expressing cells are isolated from an MZB1 transgenic animal and the MZB1-deficient cells are isolated from its non-transgenic littermate. In yet another specific example, the cells contain an MZB1 expression vector under the control of an inducible promoter; by culturing cells under inducing and non-inducing conditions, MZB1-expressing and MZB1-deficient cells, respectivel, can be obtained. The MZB1 inducible cells can be obtained by in vitro transfection or transduction or isolated from transgenic animals.

In another example, the MZB1-expressing cells express endogenous MZB1; the MZB1-deficient cells are their knock-out or knock-down counterparts which have no or reduced MZB1 expression. MZB1 knock-out cells may be obtained from an MZB1 knock-out host organism or via in vitro homologous recombination. MZB1 knock-down cells may be obtained by the in vitro introduction of an active RNAi agent (such as an siRNA, shRNA, or miRNA), an antisense RNA, a ribozyme, an RNA aptamer, a DNA aptamer, or a decoy RNA or from a transgenic host organism which expresses one or more of the above-mentioned agents. In addition, conditional knock-out or knock-down cells, either generated in vitro via transfection or transduction or obtained from conditional knock-out or knock-down animals, may be used to provide both MZB1-expressing and MZB1-deficient cells when grown under appropriate conditions.

An MZB1-specific inhibitor should inhibit at least one of the activities of MZB1 in MZB1-expressing cells, affect MZB1 knock-down cells to a lesser degree and not affect MZB1 knock-out or non-expressing cells at all. MZB1 knock-down cells which different degrees of MZB1 down-regulation can serve as highly valuable controls for determining the specificity of the candidate MZB1 activity inhibitor.

In a further example, a person skilled in the art can contact cells expressing wild-type (wt) MZB1 and cells expressing a mutant MZB1 with a candidate agent, subject the cells to one or more functional assays, and identify candidate agents which negatively affect at least one of the activities of MZB1 in cells expressing wt but not mutant MZB1. Experimental observations suggest that the ability of MZB1 to regulate antibody production is attributed to the pool of MZB1 which is associated with the endoplasmic reticulum (ER) and the ability of MZB1 to regulate cell proliferation is attributed to the pool of MZB1 that is in the cytoplasm and can be recruited to the plasma membrane. Without wishing to be bound by any theory, cells expressing MZB1 mutants which have altered subcellular localization may serve as controls for determining the specificity of a candidate inhibitor which inhibits one or more subcellular localization-associated function(s) of MZB1. In one example, cells expressing an MZB1 mutant lacking the N-terminal signal peptide (i.e., the N-terminal 18 amino acids; e.g., a polypeptide having the amino acid sequence of SEQ ID NO: 4 or encoded by the nucleotide sequence of SEQ ID NO:3) can be used as a control in the identification of agents which inhibit at least one of the cytoplasmic functions of MZB1, such as the regulation of cell proliferation. In another example, cells expressing an MZB1 mutant lacking the C-terminal ER retention signal (i.e., the C-terminal 4 amino acids REEL; e.g., a polypeptide having the amino acid sequence of SEQ ID NO: 6 or 8 or encoded by the nucleotide sequence of SEQ ID NO: 5 or 7) can be used as a control in the identification of agents which inhibit at least one of the ER-associated functions of MZB1, such as antibody secretion.

An inhibitor of MZB1 activity may interfere with the interaction between MZB1 and one or more of its interaction partners. Whether a substance interferes with the binding of MZB1 to one or more of its interaction partners can be determined by assays well known in the art, such as co-immunoprecipitation, FRET, gel filtration.

An inhibitor of MZB1 activity can be obtained by a person skilled in the art by screening candidate agents, such as a panel of antibodies, a phage display library of single-chain antibodies, an RNA aptamer library, a DNA aptamer library, a peptide aptamer library, a small molecule library, a panel of potential dominant-negative MZB1 variants, and a panel of potential dominant-negative mutants of interaction partners, using one or more activity (i.e., functional) and/or binding assays.

Since MZB1 interacts with multiple interaction partners and has multiple biological activities, it may be preferable to obtain an inhibitor of MZB1 activity which inhibits only one or more, but not all, of the biological activities of MZB1.

In one embodiment, an activity-specific inhibitor interferes with the binding of MZB1 with only one or more, but not all, interaction partner(s). In another embodiment, an activity-specific inhibit binds and interferes with the function of only one or more, but not all, functional domains of MZB1. In yet another embodiment, an activity-specific inhibitor is targeted to a specific subcellular compartment and inhibits one or more subcellular localization-specific function(s) of MZB1. For example; an intrabody with an ER retention signal may be able to inhibit ER-associated function(s) of MZB1 such as the regulation of antibody secretion without affecting the cytoplasmic function(s) of MZB1 such as the regulation of cell proliferation.

The inhibitor of MZB1 expression or activity may comprise any modifications that improve its stability, bioavailability; and/or pharmacokinetic properties and/or modify its biodistribution and/or subcellular localization.

The inhibitors of MZB1 expression or activity may be used for research as well as medical purposes.

Activators or Enhancers of MZB1 Expression or Activity

The present invention provides a substance that activates or enhances MZB1 expression. The present invention also provides a substance that activates MZB1 or enhances at least one of the biological activities of MZB1.

Activators or enhancers of MZB1 expression include, but are not limited to, nucleic acid molecules or vectors which are capable of driving the expression of MZB1, a variant or a biologically active fragment thereof, and factors, such as transcription factors, which activate or enhance the transcription from an MZB1 coding sequence.

Examples of vectors which are capable of driving the expression of MZB1, a variant or a biologically active fragment therefore include the retroviral vector pEG2-MZB1, and the MZB1-expression vectors pMZB1$_{AUG2}$ driven by the CMV promoter, pCG-FLAG-MZB1 (N-terminal FLAG-tag) and pCG-MZB1-HA (C-terminal HA-tag).

Transcription factors, such as XBP-1, Blimp-1, IRF4, and Pax5 which are important players in the regulation of plasma cell differentiation and antibody secretion, are predicted to bind to the putative MZB1 promoter and thereby regulate the expression of endogenous MZB1.

Furthermore, MZB1 expression can be induced by factors such as bacterial components like LPS.

Given the genomic sequence of the mzb1 locus, a person skilled in the art can identify factors which activate or enhance the transcription from the mzb1 gene using methods known in the art.

Activators or enhancers of MZB1 activity include, but are not limited to, MZB1, a variant or a biologically active fragment thereof, agonistic antibodies, in particular, agonistic intrabodies, and small molecule agonists.

Given the coding sequence of MZB1, a person skilled in the art can express and obtain the MZB1 protein using methods known in the art. Furthermore, a person skilled in the art can screen for agents which activate MZB1 or enhance at least one of the activities of MZB1 using either cell-based or cell-free assays, such as those described in the Examples. The same assays and strategies for identifying inhibitors of MZB1 activity can be used for identifying activators or enhancers of MZB1 activity.

Since MZB1 interacts with multiple interaction partners and has multiple biological activities, it may be preferable to generate and utilize a variant or a fragment of MZB1 which has only one or more, but not all, of the biological activities of full length MZB1. Furthermore, since MZB1 in different subcellular compartments appears to carry out different biological activities, it may be preferable to generate and utilize a variant or a fragment of MZB1 with a desired subcellular localization. Examples of such variants or fragments include the polypeptides having the amino acid sequence of SEQ ID NOS: 4, 6, 8, 10 or the polypeptides encoded by the nucleotide sequence of SEQ ID NOS: 3, 5, 7, 9.

Moreover, it may be preferable to obtain an antibody or small molecule agonist which activates or enhances only one or more, but not all, of the activities of MZB1.

In one embodiment, an activity-specific activator or enhancer interacts with only one or more, but not all, functional domains of MZB1. In another embodiment, an activity-specific activator or enhancer is targeted to a specific subcellular compartment and activates or enhances one or more subcellular localization-specific function(s) of MZB1. For example, an intrabody with an ER retention signal may be able to activates or enhances ER-associated function(s) of MZB1 such as the regulation of antibody secretion without affecting the cytoplasmic function(s) of MZB1 such as the regulation of cell proliferation.

The activator or enhancer of MZB1 expression or activity may comprise any modifications that improve its stability, bioavailability, and/or pharmacokinetic properties and/or modify its biodistribution and/or subcellular localization.

The activators or enhancers of MZB1 expression or activity may be used for research as well as medical purposes.

Pharmaceutical Compositions

The present invention provides a pharmaceutical composition comprising an isolated nucleic acid or a vector of the present invention and a pharmaceutically acceptable carrier.

The present invention also provides a pharmaceutical composition comprising an isolated polypeptide of the present invention and a pharmaceutically acceptable carrier.

The present invention further provides a pharmaceutical composition comprising an inhibitor of MZB1 expression or activity of the present invention and a pharmaceutically acceptable carrier.

The present invention additionally provides a pharmaceutical composition comprising an activator or enhancer of MZB1 expression or activity of the present invention and a pharmaceutically acceptable carrier.

In one embodiment, the active ingredient is modified to achieve improved stability, bioavailability, pharmacokinetic properties, biodistribution (in particular, organ-, tissue-, or cell type-specificity), and/or subcellular localization.

In one embodiment, the pharmaceutical composition further comprises an agent which facilitates the delivery of the active ingredient. For example, when the active ingredient is a DNA or RNA molecule, the pharmaceutical composition may further comprise a DNA or RNA complexation agent such as a liposome or a polycationic peptide.

In certain embodiments, the pharmaceutical composition of the present invention further comprises one or more additional pharmaceutically active and/or therapeutic agents which are used for the treatment of autoimmune disorders and immunodeficiency in a mammal.

The pharmaceutical composition of the present invention may be formulated in any way that is compatible with its therapeutic application, including intended route of administration, delivery format and desired dosage. Optimal pharmaceutical compositions may be formulated by a skilled person according to common general knowledge in the art, such as that described in Remington's Pharmaceutical Sciences (18th Ed., Gennaro A R ed., Mack Publishing Company, 1990).

The pharmaceutical compositions of the present invention may be formulated for instant release, controlled release, timed-release, sustained release, extended release, or continuous release.

The pharmaceutical compositions provided by the present invention may be administered by any routes known in the art, including, but not limited to, topical, enteral and parenteral routes. Topic administration includes, but is not limited to, epicutaneous, inhalational, intranasal, vaginal administration, enema, eye drops, and ear drops. Enteral administration includes, but is not limited to, oral, rectal administration and administration through feeding tubes. Parenteral administration includes, but is not limited to, intravenous, intraarterial, intramuscular, intracardiac, subcutaneous, intraosseous, intradermal, intrathecal, intraperitoneal, transdermal, transmucosal, and inhalational administration.

The optimal dosage, frequency, timing and route of administration can be determined by a person skilled in the art.

The dosage regimen utilizing the inhibitor of the present invention is selected in accordance with a variety of factors including type, species, age, weight, sex and medical condition of the patient; the severity of the condition to be treated; the route of administration; and the particular compound employed. It will be acknowledged that an ordinarily skilled physician or veterinarian can easily determine and prescribe the effective amount of the compound required to prevent, counter or arrest the progress of the condition.

Preferably, the pharmaceutical composition of the present invention is suitable for administration to a patient. In the context of the present invention the term "patient" means an individual in need of a treatment of an autoimmune disease or immunodeficiency. Preferably, the patient is a vertebrate, even more preferred a mammal, particularly preferred a human.

The terms "treatment" and "treating" are used herein to generally mean obtaining a desired pharmaceutical and/or physiological effect. Preferably, the effect is therapeutic in terms of partially or completely curing an autoimmune disease or immunodeficiency. The term "treatment" as used herein covers any treatment of tissue suffering from an autoimmune disease or immunodeficiency and/or organ defects and/or dysfunction caused by an autoimmune disease or immunodeficiency in a mammal, particularly a vertebrate and more preferably a human, and includes regenerating and/or repairing suffering from an autoimmune disease or immunodeficiency and/or organ or tissue dysfunction. Thus, the pharmaceutical composition of the present invention is preferably suitable for the prevention and/or treatment of an autoimmune disease or immunodeficiency.

The term "prevention" or "preventing" when used herein means to obtain a protective effect on a tissue which is already suffering from an autoimmune disease or immunodeficiency so as to prevent further damage and/or a protective effect on a tissue which is at a risk of suffering from an autoimmune disease or immunodeficiency.

Accordingly, the pharmaceutical composition of the present invention for the purpose of treating and/or preventing an autoimmune disease or immunodeficiency may preferably be administered to a subject who is at a risk of an autoimmune disease or immunodeficiency and/or who already suffers from an autoimmune disease or immunodeficiency. Thus, the pharmaceutical composition of the present invention may preferably be administered to a subject who is diagnosed to be at a risk of an autoimmune disease or immunodeficiency and/or who already suffers from an autoimmune disease or immunodeficiency.

The term "administered" means administration of a therapeutically effective dose of a pharmaceutical composition of the present invention. Preferably, said therapeutically effective dose is administered to a patient who has tissue suffering from an autoimmune disease or immunodeficiency. Particularly preferred said therapeutically effective dose is administered to a patient suffering from organ defects and/or dysfunction caused by an autoimmune disease or immunodeficiency. By "therapeutically effective amount" is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The uses, methods and compositions of the present invention are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

Use of an Inhibitor of MZB1 Expression or Activity

The present invention provides an inhibitor of MZB1 expression or activity for treating autoimmune diseases in a mammal, in particular, autoimmune diseases that are caused by and/or associated with auto-antibodies.

The present invention also provides the use of an inhibitor of MZB1 expression or activity for the preparation of a pharmaceutical composition for treating autoimmune diseases in a mammal, in particular, autoimmune diseases that are caused by and/or associated with auto-antibodies.

Autoimmune diseases include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, autoimmune uveitis, allergic encephalomyelitis, pure red cell anemia, idiopathic thrombocytopenia, Wegener's granulomatosis, chronic active hepatitis, lichen planus, Graves' disease, sarcoidosis, primary biliary cirrhosis, and interstitial lung fibrosis.

In one embodiment, the inhibitor is an inhibitor of MZB1 expression, including but not limited to antisense RNA, RNA olignucleotides that are active in RNA interference (RNAi) such as siRNA, shRNA and miRNA, ribozyme, RNA and DNA aptamers, and decoy RNAs.

In a specific embodiment, the inhibitor is an RNA oligonucleotide which is active in RNAi, such as an siRNA, shRNA and miRNA, and which targets GCGAAAGCA-GAGGCTAAAT (SEQ ID NO: 14), GGAGTCCTATG-GAGTTCAT (SEQ ID NO: 15), CCAGATCTATGAAGC-CTAC (SEQ ID NO: 16), or CTGCCACTGTTGCTACTGT (SEQ ID NO: 17) within the MZB1 coding region. In certain embodiments, the inhibitor of MZB1 expression is an siRNA. In certain other embodiments, the inhibitor of MZB1 expression is an shRNA, in particular, an shRNA comprising the nucleotide sequence of GCGAAAGCA-GAGGCUAAAUUCAAGAGAAUUUAGCCUCUGC-UUUCGC (SEQ ID NO: 18), GCAGUCCUAUGGAGUU-CAUUUCAAGAGAAUGAACUCCAUAGGACUGC (SEQ ID NO: 19), CCAGAUCUAUGAAGCCUACUU-CAAGAGAGUAGGCUUCAUAGAUCUGG (SEQ ID NO: 20), and CUGCCACUGUUGCUACUGUUU-CAAGAGAACAGUAGCAACAGUGGCAG (SEQ ID NO: 21) (the bold letters denotes the loop sequence and the normal letters denote the loop sequence).

In another embodiment, the inhibitor is an inhibitor of MZB1 activity, including but not limited to neutralizing antibodies, in particular, neutralizing intrabodies, RNA aptamers, DNA aptamers, peptide aptamers, small molecule inhibitors, dominant-negative MZB1 and dominant-negative interaction partner.

In a preferred embodiment, the inhibitor inhibits only the antibody production-promoting activity of MZB1. In one embodiment, the inhibitor interferes with the binding between MZB1 and Bip-1. In another embodiment, the inhibitor interacts with the domain of MZB1 which is involved in the regulation of antibody secretion and interferes with its function. In yet another embodiment, the inhibitor is targeted to the ER.

In another preferred embodiment, the inhibitor inhibits only the proliferation-inhibiting and/or BCR signaling-inhibiting activity of MZB1. In one embodiment, the inhibitor interferes with the binding between MZB1 and RACK1. An example of such an inhibitor is antibody 2F9. In another embodiment, the inhibitor interacts with the domain of MZB1 which is involved in the regulation of cell proliferation and BCR signaling and interferes with its function. In yet another embodiment, the inhibitor is targeted to the cytoplasm or the plasma membrane.

The inhibitors of the present invention need to be provided intracellularly in order to exert their inhibitory effects. The inhibitors of the present invention may be modified and/or formulated by a person skilled in the art using known methods in order to achieve their intracellular delivery.

Certain inhibitors, such as shRNA, scFv, dominant-negative MZB1 and dominant-negative interaction partner, may be provided in the form of coding nucleic acid molecules or vectors which allow for their intracellular expression.

In a perferred embodiment, the inhibitors of the present invention are modified and/or formulated for targetted delivery into B cells, in particular, marginal zone (MZ) B cells, B-1 B cells, and/or follicular (FO) B cells.

In certain embodiments, the pharmaceutical composition is for use in combination with one or more existing treatments of autoimmune diseases.

Mammals include, but are not limited to, laboratory animals such as mice, rats, rabbits, cats, dogs, farm animals such as horses, sheep, cattle, cows, pigs, non-human primates, and humans. In a preferred embodiment, the mammal is human.

Use of an Activator or Enhancer of MZB1 Expression or Activity

The present invention provides an activator or enhancer of MZB1 expression or activity for treating immunodeficiencies in a mammal, in particular, immunodeficiencies that are caused by and/or associated with insufficient antibody production.

The present invention also provides the use of an activator or enhancer of MZB1 expression or activity for the preparation of a pharmaceutical composition for treating immunodeficiencies in a mammal, in particular, immunodeficiencies that are caused by and/or associated with insufficient antibody production.

Immunodeficiencies include, but are not limited to, hereditary immunodeficiency, spontaneous immunodeficiency and drug-induced immunodeficiency (such as that induced by immunosuppressants used in transplantation and chemotherapeutic agents used for treating cancer).

The present invention further provides the use of an activator or enhancer of MZB1 expression or activity for enhancing antibody production in a cell.

The present invention additionally provides an in vitro method for enhancing antibody production in a cell comprising contacting the cell with an activator or enhancer of MZB1 expression or activity.

The cell may be a primary B cell, such as a FO B cell, a MZ B cell or a B1 B cell, a B cell line, or a B cell hybridoma.

Activators or enhancers of MZB1 expression include, but are not limited to, nucleic acid molecules or vectors which are capable of driving the expression of MZB1, a variant or a biologically active fragment thereof, and transcription factors which activate or enhance the transcription from an MZB1 coding sequence.

Activators or enhancers of MZB1 activity include, but are not limited to, MZB1, a variant or a biologically active fragment thereof, agonistic antibodies, in particular, agonistic intrabodies, and small molecule agonists.

In a preferred embodiment, the activator or enhancer activates or enhances only the antibody production-promoting activity of MZB1. In one embodiment, the activator or enhancer interacts with the domain of MZB1 which is involved in the regulation of antibody secretion and activates or enhances with its function. In another embodiment, the inhibitor is targeted to the ER.

In a perferred embodiment, the activators or enhancers of the present invention are modified and/or formulated for targeted delivery into B cells, in particular, marginal zone (MZ) B cells, B-1 B cells, and/or follicular (FO) B cells.

The present invention additionally provides an activator or enhancer of MZB1 expression or activity for treating immunodeficiencies in a mammal, in particular, immunodeficiencies that are caused by and/or associated with T cell deficiency due to reduced or absent TCR signalling and/or co-stimulation.

The present invention also provides the use of an activator or enhancer of MZB1 expression or activity for the preparation of a pharmaceutical composition for treating immunodeficiencies in a mammal, in particular, immunodeficiencies that are caused by and/or associated with T cell deficiency due to reduced or absent TCR signalling and/or co-stimulation.

In a perferred embodiment, the activators or enhancers of the present invention are modified and/or formulated for targetted delivery into T cells.

The activators or enhancers of the present invention need to be provided intracellularly in order to exert their activating or enhancer effects. The activators or enhancers of the present invention may be modified and/or formulated by a person skilled in the art using known methods in order to achieve their intracellular delivery.

Certain activators or enhancers, such as MZB1, a variant or a biologically active fragment thereof, and agonist scFv, may be provided in the form of coding nucleic acid molecules or vectors which allow for their intracellular expression.

In certain embodiments. the pharmaceutical composition is for use in combination with one or more existing treatments for immunodeficiencies, The present application provides MZB1 or a variant or a fragment thereof which comprises the the amino acid sequence of SEQ ID NO:10 or an amino acid sequence encoded by the nucleotide sequence of SEQ ID NO:9 for inhibiting the growth of tumor cells and/or bacterial cells.

The present application provides MZB1 or a variant or a fragment thereof which comprises the the amino acid sequence of SEQ ID NO:10 or an amino acid sequence encoded by the nucleotide sequence of SEQ ID NO:9 for treating a tumor and/or a bacterial infection in a mammal.

Mammals include, but are not limited to, laboratory animals such as mice, rats, rabbits, cats, dogs, farm animals such as horses, sheep, cattle, cows, pigs, non-human primates, and humans. In a preferred embodiment, the mammal is human.

Method for Polypeptide Production

The present invention provides a process for producing a polypeptide of the present invention comprising culturing a host cell of the present invention under suitable conditions to express the polypeptide, and optionally isolating the polypeptide from the culture.

The suitable conditions can be determined by a person skilled in the art, taking into consideration the host cell and expression vector used.

The polypeptide of the present invention may be enriched, partially purified or purified from the cultured host cells or the culture media by any suitable methods known in the art, such as those described in the Current Protocols in Protein Science (supra).

In some cases, the polypeptide of the present invention may not be biologically active upon isolation. Various methods known in the art for "refolding" can be used to restore biological activity.

Method for Screening for Modulators of MZB1 Expression or Activity

The present invention provide a method for screening for modulators, including inhibitors, activator and enhancers, of MZB1 expression, comprising the steps of:
(a) contacting a cell expressing MZB1 or a variant thereof with candidate compounds;
(b) comparing the expression of MZB1 in the presence and absence of the candidate compounds; and
(c) identifying compounds which modulate (increase or decrease) MZB1 expression.

The present invention also provides a method for screening for modulators, including inhibitors, activator and enhancers, of MZB1 activity comprising the steps of:
(a) contacting MZB1, a variant or a biologically active fragment thereof, or a cell expressing MZB1, a variant or a biologically active fragment thereof with candidate compounds;
(b) comparing the activity of MZB1 in the presence and absence of the candidate compounds; and
(c) identifying compounds which modulate (increase or decrease) MZB1 activity.

The present invention is illustrated by the following examples.

EXAMPLES

1. Materials and Methods 1.1 Cell Lines

All cell lines were maintained at 37° C. in a 5% $CO_2$ gassed atmosphere. If not stated otherwise, cell lines were propagated according to the information supplied by ATCC (atcc.org). Cells growing in suspension were maintained at a concentration between $1\times10^5$ and $1\times10^6$ cells/ml. Adherent cells were grown to confluence. Every 2-3 days they were split by removal of media and subsequent incubation with a 0.25% trypsin-EDTA solution (Gibco) for 1 minute. Upon detachment, fresh media was added and cells were diluted 1:6 into new culture dishes. Stocks in liquid nitrogen were prepared by freezing $5\times10^6$ cells/ml in FCS containing 10% DMSO. Samples were frozen at −80° C. in an isopropanol-containing freezing box (Nalgene) and transferred to liquid nitrogen after 24 hours.

K46:

This murine, mature B lymphoblastoid cell line is 20% semiadherent and produces surface $IgG_{2a}$/kappa (Kim et al., 1979). For maintenance cells were cultured in RPMI 1640 media (PAA) supplemented with 10% (v/v) heat-inactivated FCS, 1% (v/v) PSG and 56 µM β-ME.

MZB1 Knockdown K46 Cells (shRNA):

Using RNA interference, MZB1 was knocked down in K46 cells using an shRNA which can be processed into an active siRNA which targets the sequence of GCGAAAGCAGAGGCTAAAT (# inv2) (SEQ ID NO: 14) in the MZB1 coding region. Two independent clones were generated, # inv2-10 and # inv2-29. As control, K46 cells were stably transfected with the pSuper.neo+GFP vector without an MZB1-specific hairpin. Two independent clones were generated, # pSup-13 and # pSup-17. Cells were cultured in RPMI 1640 media (PAA) supplemented with 10% (v/v) heat-inactivated FCS, 1% (v/v) PSG (Penicillin-Streptomycin-Glutamine) and 56 µM β-mercaptoethanol β-ME). Before freezing, these cells were passaged in selection media additionally containing 1 mg/ml active G418.

MZB1 Knockdown K46 Cells with Restored MZB1 Expression (shRNA+MZB1):

MZB1 expression was reconstituted in shRNA cells by stable transfection of pIRES-MZB1-mut-puro which drives the expression of a mutant version of MZB1 which is resistant to downregulation by shRNA # inv2. K46 shRNA+ MZB1 cells were cultured in RPMI 1640 media (PAA) supplemented with 10% (v/v) heat-inactivated FCS, 1% (v/v) PSG and 56 µM β-ME. To select for stable integration of the plasmid, cells were passaged in selection media additionally containing 1 mg/ml active G418 and 1 µg/ml Puromycin.

1.2 Primary Cell Culture—Splenocytes and Peritoneal Cells

All primary cells (splenocytes and peritoneal cells) were cultured at 37° C. in a 5% $CO_2$ gassed atmosphere. Cells were maintained at a concentration between $5\times10^5$ and $1\times10^6$ cells/ml in RPMI 1640 media (PAA) supplemented with 10% (v/v) heat-inactivated FCS, 1% (v/v) PSG, 1% (v/v) Non-essential-Amino-Acids, 1% Sodium Pyruvate, 10 mM HEPES and 56 µM β-mercaptoethanol (splenocyte medium). Stocks in liquid nitrogen were prepared by freezing $5\times10^6$ cells/ml in FCS containing 10% DMSO. Samples were frozen in a freezing machine (Custom Bio Genic Systems) according to the manufacturer's recommendations and transferred to liquid nitrogen.

1.3 Retroviral Transduction of B1/MZ B Cells with MZB1 miRNA and Subsequent Analysis of Antibody Secretion For introduction of MZB1 miRNA into primary suspension cells (e.g. B1 B cells or MZ B cells) retroviral transduction using the packaging cell line GP+E 86 (Markovitz et al., 1988) was performed. This packaging cell line produces the retrovirus encoding for MZB1-specific hairpins which target the same MZB1 sequence GCGAAAGCA-GAGGCTAAAT (SEQ ID NO: 14 as # inv2 and secretes the assembled virus into the supernatant, ready to infect the target cells. To generate the packaging lines GP+E86-miRNA-MZB1 and GP+E86-MCS (MCS stands for multiple cloning site and is an empty vector for control), 293T cells were transiently transfected with p-miRNA-MZB1, a retroviral vector containing MZB1-specific hairpin on the pMSCV-IRES-GFP backbone, or the empty vector p-miRNA-MCS. The IRES-GFP-cassette was substituted with a combined GFP-pre-miRNA-cassette derived from the invitrogen BLOCK-iT™Pol II miR RNAi expression vector system. The expression of the GFP-pre-miRNA-cassette is driven by the retroviral 5'-LTR. This system permits visual or automated selection of cells expressing the pre-miRNA through co-cistronic expression of GFP. In both cases, the retroviral helper plasmid pEQPAM3, encoding for the viral gag, pol and env genes was co-transfected. 12 hours post transfection, the supernatant of 293T cells was filtered (0.45 µm), polybrene added to a final concentration of 2 µg/ml and transferred onto semi-confluent GP+E86 cells. The supernatant was exchanged following this procedure every 12 hours and repeated four times. Retrovirus producing cells were enriched by cell sorting for GFP cells.

For retroviral transduction of B1 and MZ B cells, GP+E86-miRNA-MZB1 or GP+E86-MCS cells ($5\times10^6$ cells/10 plate) were plated on gelatinized tissue culture plates and cultured for 16 hours. $5\times10^6$ FACS-sorted B1 B cells or MZ B cells were resuspended in splenocyte media containing 2 µg/ml polybrene and co-cultured for 36 h on confluent GP+E86-miRNA-MZB1 or GP+E86-MCS feeder-layers. Transduced B1 B cells or MZ B cells were enriched by FACS-sorting for GFP$^+$ cells. To control for downregulation of MZB1 protein levels, an immunoblot using anti-MZB1 specific antibody was performed with cells extracts of infected B1 and MZ B cells and compared to control cells infected with empty vector.

To investigate antibody secretion behavior in primary cells (B1 or MZ B cells) with reduced MZB1 protein levels, ELISA assays as well as ELISPOT experiments were performed. For ELISA, the infected and FACS sorted cells (GFP$^+$ cells) were plated on 24 well plates and incubated for up to three days in splenocyte medium in the presence or the absence of LPS stimulation. The concentration of secreted antibody was determined in supernatant isolated 6 h, 24 h, 48 h and 72 h after culture start using a standard IgM-specific ELISA protocol. Moreover, modified ELISA protocols specifically detecting polyreactive antibodies were carried out, testing whether MZB1 reduction results in a shift of quality of the secreted antibody. To address potential limitations in the ability of an ELISA to detect the output of rare antibody secreting cells, ELISPOT assays which are theoretically able to detect every single cell secreting IgM were performed. ELISPOT assays were carried out on MultiScreen-HA filter plates (Millipore). GFP$^+$ cells were incubated for 6 h, 24 h, 48 h and 72 h at 37° C. on pre-coated 96-well filter plates in the presence or the absence of LPS stimulation and developed with AP substrate, marking every antibody secreting cell with a blue spot on the filter. Spots were counted using specific software in order to identify possible differences in the number of antibody secreting cells between the miRNA culture and the control culture of primary cells.

1.4 AnnexinV Staining

Annexin V staining for identification of early apoptotic cells was performed according to the protocol provided by the manufacturer (BD Biosciences). Briefly, cells were washed twice with cold PBS and then resuspended in 1× Binding Buffer (supplied by manufacturer) at a concentration of approximately $1 \times 10^6$ cells/ml. 100 µl of the solution ($\sim 1 \times 10^5$ cells) were transferred to a 4 ml FACS tube. 5 µl Annexin V-PE and 5 µl 7AAD (vital dye) were added. The cells were gently mixed and an incubated for 15 min at room temperature in the dark. Afterwards 400 µl of 1× Binding Buffer were added to each tube and the samples were analyzed within 1 hour by flow cytometry.

1.5 Calcium Mobilization

Cells ($5 \times 10^6$) were incubated with 5 µg/ml of Indo-1 AM (Molecular Probes) and 0.5 µg/ml of nonionic, low-toxicity detergent Pluronic® F-127 (Molecular Probes) in RPMI medium (PAA) supplemented with 1% FCS at 37° C. After 45 min incubation, the cell pellets were resuspended in RPMI medium plus 1% FCS and kept on ice. $Ca^{2+}$-response was induced by adding goat anti-kappa antibody (mouse-specific) (Southern Biotechnology) at a final concentration of 5 µg/ml. The $Ca^{2+}$-concentration of the used RPMI-media was either 2 mM or 0.5 mM. Increases in free intracellular calcium in gated B or T cell populations were measured in real time on a FACSAria (BD Biosciences).

1.6 Proliferation Assay

Purified primary cells as well as cell culture suspension cells were plated in triplicate in 96-well-flat-bottomed plates in concentrations of $1 \times 10^5$, $3 \times 10^4$, $1 \times 10^4$ and $3 \times 10^3$ cells/well. Cells were either kept unstimulated or activated with the following mitogens: 5 µg/ml anti-kappa (Southern Biotechnology), 0.3 µg/ml anti-CD3ε (nano Tools), 0.1-0.3 µg/ml anti-CD28 (eBioscience) or 2 ng/ml recombinant mouse IL-2 (R&D Systems). Cells were pulsed with [$^3$H] thymidine (1.5 pCi/well) for 18 h. Proliferation as the mean [$^3$H]thymidine incorporation of triplicate cultures was assayed by scintillation counting.

1.7 Preparation of Whole Cell Protein Extracts

Cell pellets of stimulated or unstimulated cells were washed once with ice cold 1×PBS and resuspended in an appropriate volume (50 µl-2 ml) of RIPA buffer (50 mM Tris-Cl, pH8.0, 150 mM NaCl, 1.0% (v/v) NP-40 (Igepal CA-630), 0.5% deoxycholate (DOC), 0.1% SDS), Standard CoIP buffer (50 mM Tris-Cl, pH 7.4, 15 mM EGTA, 100 mM NaCl, 0.1% (v/v) Triton X-100), or Digitonin-lysis buffer (50 mM Tris-Cl, pH7.5, 150 mM NaCl, 1% Digitonin, 5 mM EDTA), freshly supplemented with 1×PMSF, 1× Sodium orthovanadate, 1×PIM (protease inhibitor mix) and 1×NaF. For enhanced disruption of cells and sheering of DNA, samples were sonified 2 times for 1 minute in a Branson sonifier 450 using a pre-chilled water bath, 100% duty and an output control of 6-7. In case of lysis with Digitonin-containing buffer, sonification step was omitted. Complete cell lysis was checked under the microscope and the sample was centrifuged at maximum speed and 4° C. for 15 minutes in an Eppendorf 54158 centrifuge to spin down cell debris. Protein content of the supernatant was determined by Bradford assay as described, and the samples were either snap-frozen in liquid nitrogen and then stored at −80° C., or immediately used for immunoprecipitation or immunoblot.

1.8 Membrane-Cytosol Fractionation

Membrane and cytosol fractions of K46 cells were prepared as previously described (Huber et al., 2000). Briefly, $1\text{-}5 \times 10^7$ cells were pelleted and resuspended in 1 ml of ice cold hypotonic lysis buffer (20 mM Tris-C, pH 7.4, 10 mM EDTA, 5 mM Na$_3$VO$_4$, 10% v/v protease inhibitor cocktail (Sigma)), incubated for 5 min on ice, and sonicated with $15 \times 1^{-5}$ strokes on ice using an ultrasonic cell disruptor (Branson). Cell debris was removed by centrifugation at 3000 rpm for 5 min at 4° C. The supernatant was centrifuged at 100,000×g for 60 min at 4° C. in an ultracentrifuge (Optima® LE-80K Ultracentrifuge, Beckman), using a SW55Ti rotor. The supernatant corresponds to the cytosol fraction and was stored on ice. The pellet was washed twice with hypotonic lysis buffer containing 150 mM of NaCl. The pellet was then resuspended in 200-500 µl of hypotonic lysis buffer containing 0.2% NP-40 and 0.5% sodium deoxycholate (NP-40-DOC-buffer) by repeated vortex mixing. After incubating for 60 min at at 4° C. on a shaker (1000 rpm) (Thermomixer comfort, Eppendorf), the suspension was ultracentrifuged at 100,000×g for 30 min, and the supernatant was collected as the membrane fraction. Protein contents of both cytosolic and membrane fractions were determined by Bradford assay as described, and the samples were snap-frozen in liquid nitrogen and then stored at −80° C. After gently thawing the samples on ice, they were used either for immunoprecipitation or immunoblot.

1.9 Immunoprecipitation

Protein extracts were prepared as described, 500 µg-2 mg of protein extract as determined by Bradford assay was used for a single immunopreciptation experiment. 1-5 µg of antibody was added and the total volume adjusted to 400 µl using Standard CoIP buffer (50 mM Tris-Cl, pH 7.5, 15 mM EGTA, 150 mM NaCl, 0.1% (v/v) Triton X-100), Digitonin lysis buffer (50 mM Tris-Cl, pH7.5, 150 mM NaCl, 1% (w/v) Digitonin, 5 mM EDTA) or NP-40-DOC-buffer (20 mM Tris-C, pH 7.4, 10 mM EDTA, 0.2% NP-40, 0.5% sodium deoxycholate (DOC)), freshly supplemented with 1×PMSF, 1× Sodium orthovanadate, 1×PIM (protease inhibitor mix) and 1×NaF. The lysates were incubated on a rotary shaker at 4° C. for 5-16 hours. 40 µl of Protein A, Protein G or Protein L beads that had been blocked with 5% (w/v) BSA for 5-16 hours and equilibrated in the appropriate buffer were added and antibody capturing was performed for 1-1.5 hours on a rotary shaker at 4° C. Beads were spun down at 800×g for 3 minutes at 4° C. and washed 4 times with 1 ml of the buffer used for binding. Beads were resuspended in 40 µl 2×SDS loading dye and immune complexes were eluted by boiling at 95° C. for 10 minutes. Samples were stored at −20° C. or immediately loaded onto an SDS polyacrylamide gel.

When proteins tended to stick to the beads, a pre-clear step was included before the addition of antibodies. For this, the protein extract was supplemented with 40 µl of Protein A, Protein G or Protein L beads that had been equilibrated in the appropriate buffer and was incubated on a rotary shaker at 4° C. for 2 hours. Afterwards, the sample was centrifuged at 800×g and 4° C. for 3 minutes. The supernatant was transferred to a fresh 1.5 ml microcentrifuge tube, and used for the immunoprecipitation procedure.

In order to reach higher precipitation efficiency, Protein A/G-purified anti-MZB1 antibodies 2F9, 5C11, 5H8 and 2H7 were directly coupled to CNBr-activated Sepharose-beads (GE Healthcare) and used for a "one-step" anti-MZB1 immunoprecipitation.

1.10 SOS PAGE and Immunoblot

Protein samples dissolved in 1×SDS loading dye were separated on SDS polyacrylamide gels of the required resolution range. Gels were prepared according to standard procedures. Typically, MZB1 (≈21 kDa) was detected on a 12% or 15% gel, whereas bigger proteins like PLCγ (≈150 kDa) or whole cell extracts for α-phospho-tyrosine blots were separated on a 10% gel. Electrophoresis conditions were 200V and 400 mA for 45-60 minutes using the appropriate buffer. Proteins were transferred on nitrocellulose membranes using semi-dry blot system (Bio-Rad). Transfer conditions were 0.8 mA/cm2 and 300V for 1 hour in 1× Tris-Glycine buffer (2.5M Tris-Cl, 1.9M glycine, 1% (w/v) SDS) containing 20% methanol. Membranes were blocked for either 1 hour or o/n in 5% (w/v) non-fat dried milk powder dissolved in 1×PBS supplemented with 0.1% Tween®20 (PBST). After a quick washing step using PBST, membranes were incubated with primary antibody diluted in PBST for 1-5 hours. The following dilutions were used:

| Antibody | Dilution |
| --- | --- |
| α-MZB1 (clone 2F9), rat monoclonal | 1:100 |
| α-PKC-β (clone 36), mouse monoclonal, #610127 | 1:200 |
| α-RACK1 (clone 20), mouse monoclonal, IgM #610177 | 1:200 |
| α-Phospho-Btk (Tyr223), rabbit monoclonal | 1:4000 |
| α-Phospho-Btk (Ser180), mouse monoclonal (clone 3D3) | 1:1000 |
| α-Btk, rabbit monoclonal | 1:2000 |
| α-Phospho-PLCγ2 (Tyr1217), rabbit polyclonal | 1:1000 |
| α-PLCγ2, rabbit polyclonal | 1:1000 |
| α-BAP32, mouse monoclonal | 1:500 |
| α-BIP, rabbit polyclonal | 1:500 |
| α-GAPDH (clone 6C5), mouse monoclonal | 1:2000 |

Membranes were washed 3 times for 5 minutes with PBST and incubated for 1 hour with secondary antibody conjugated to horseradish peroxidase. Secondary antibodies were diluted as followed:

| Antibody | Dilution |
| --- | --- |
| goat α-mouse-IgG, peroxidase-conjugated | 1:10000 |
| mouse-α-rat-IgG, peroxidase-conjugated | 1:3333 |
| goat-α-mouse-IgM, peroxidase-conjugated | 1:10000 |
| goat-α-rabbit-IgG, peroxidase-conjugated | 1:10000 |

Membranes were washed 3 times for 5 minutes with PBST before being incubated for 2 min with ECL™ Western Blotting Detection Reagents (Amersham/GE Healthcare). For visualization of proteins, membranes were exposed to autoradiographic films (Bechtold) for different time periods.

1.11 Immunofluorescence

In order to determine the exact location of overexpressed and endogenous proteins within a cell, immunostaining on fixed cells was performed. Images of the fixed slides were taken on a LSM 510 META confocal microscope (Zeiss) using a 63×/oil objective.

1.11.1 Indirect Immunofluorescence of Adherent Cells

Cover slips were placed in 6-well tissue culture plates and coated with an excess of Poly-L-lysine solution (diluted 1 to 10 in ddH$_2$O) for 10 minutes at room temperature. The Poly-L-lysine solution was aspirated and after drying the coverslips at 70° C. for 1 hour, 2×10$^5$ cells/well of NIH 3T3-FLAG-MZB1 cells (NIH3T3 cells stably expressing N-terminally FLAG-tagged MZB1 under the control of the CMV promoter) were seeded on the coated coverslips. Cells were cultured as previously described for 16-24 hours.

Cells were washed once with PBS and fixed for 10 minutes with 2 ml of 4% (w/v) paraformaldehyde solution. After fixation, cells were washed 3 times for 5 minutes with 1×PBS containing 0.1% Triton X-100. Blocking was performed in 1×PBS containing 3% (v/v) goat serum for 30 min. Subsequently, primary antibody diluted in 100 µl 1×PBS, 0.1% Triton X-100 and 3% goat serum was added to the cells, and the cover slips were covered with a small parafilm strip to prevent drying. After 1 hour incubation, the cover slips were washed 3 times for 5 minutes with 1×PBS containing 0.1% Triton X-100. Incubation with secondary antibody diluted 1 to 100 in 1×PBS, 0.1% Triton X-100 and 3% goat serum was performed for 1 hour in the dark. After 3 washing steps of 5 minutes each, cell nuclei were stained with 0.5 ml of 5 µg/ml DAPI diluted 1 in 1000 in 1×PBS, 0.1% Triton X-100 for 5 minutes. Cells were mounted on slides using ProLonga Gold antifade reagent (Invitrogen). After incubation for 24 hours at room temperature in the dark, slides were sealed with nail polish. The following dilution of primary and secondary antibody was used:

| Antibody | Dilution |
| --- | --- |
| α-MZB1 (clone 2F9), rat monoclonal | undiluted |
| α-BAP31, rabbit monoclonal | 1:100 |
| Alexa Fluor ® 647 chicken α-rat IgG | 1:200 |
| Alexa Fluor ® 488 goat α-rabbit IgG | 1:200 |

1.11.2 Indirect Immunofluorescence of Suspension Cells

Covers lips were placed in 6-well tissue culture plates and coated with undiluted Poly-L-Lysine for 10 minutes at room temperature. Shortly before use the plates were washed with 1×PBS for 5 to 20 minutes and then rinsed with RPMI 1640 (PAA) complete media. Suspension cells (e.g. MZ B cells) were centrifuged and resuspended in an appropriate amount of media. 3×10$^5$ cells in 100 µl volume were dropped on each cover slip and incubated for 3-5 minutes at room temperature to let the cells settle down.

Further steps were performed accordingly to the procedure for adherent cells. The following dilution of primary and secondary antibody was used:

| Antibody | Dilution |
| --- | --- |
| α-MZB1 (clone 2F9), rat monoclonal | undiluted |
| α-RACK1 (clone 20), mouse monoclonal, IgM | 1:200 |
| Alexa Fluor ® 647 chicken α-rat IgG | 1:200 |
| Alexa Fluor ® 488 goat α-mouse IgM | 1:200 |

1.12 MZB1 Knock-Out Mouse

A pGKneo-pA cassette was inserted in frame with the ATG codon of the mzb1 gene, which renders mzb1 inactive (FIG. 37). Homologous recombination in ES cells was identified by Southern blot analysis. The relevant restriction sites used for Southern blot analysis and the location of the probe are indicated (FIG. 37).

1.13 Retroviral Transduction of Primary Follicular B Cells with MZB1 Expression Vector For stable introduction of MZB1 cDNA into primary suspension cells (e.g. follicular B cells) retroviral transduction using the packaging cell line GP+E 86 (Markowitz et al., 1988) was performed.

To generate the packaging lines GP+E86-MZB1 and GP+E86-MCS, 293T cells were transiently transfected with pEG2-MZB1 (retrovirus containing MZB1 cDNA) or the empty vector pEG2-MCS. In both cases, the retroviral helper plasmid pEQPAM3 encoding the viral gag, pol and env genes was co-transfected. 12 h post transfection, the supernatant of 293T cells was filtered (0.45 μm), polybrene added to a final concentration of 2 μg/ml and transferred onto semi-confluent GP+E86 cells. The supernatant was exchanged following this procedure every 12 h and repeated four times. Retrovirus producing cells were enriched by cell sorting for GFP$^+$ cells.

For retroviral transduction of follicular (FO) B cells, GP+E86-MZB1 or GP+E86-MCS cells ($5 \times 10^6$ cells/10 plate) were plated on gelatinized tissue culture plates and cultured for 16 h. $5 \times 10^6$ FACS-sorted follicular B cells were resuspended in splenocyte media containing 2 μg/ml polybrene and co-cultured for 36 h on confluent GP+E86-MZB1 or GP+E86-MCS feeder-layers. Transduced FO B cells were enriched by FACS-sorting.

1.14 Transient Transfection of Adherent Cells Using Calcium Phosphate

For a single transfection, $3.2 \times 10^5$ GP+E 86 were seeded onto a 6 cm tissue culture plate 14 hours before transfection. 250 μl of freshly prepared 250 mM $CaCl_2$ were mixed with 15 μg of DNA (vector DNA+salmon sperm DNA to reach at least 15 μg). The solution was supplemented with 250 μl HBS, pH7.05 (280 mM NaCl, 10 mM KCl, 1.5 mM $Na_2HPO_4$, pH7.5, 12 mM glucose, 50 mM HEPES, pH7.6) under stirring conditions. The mixture was incubated for 25 minutes at RT before being added to the cells whose medium had been replaced with 5 ml of fresh complete medium in the meantime. The transfection mixture was incubated for 4-6 hours. To remove calcium phosphate precipitates, cells were washed three times with 1×PBS and upon addition of fresh medium, incubated for 36-48 hours.

1.15 Primary Cell Culture—Splenocytes and Peritoneal Cells

All primary B cells (splenocytes and peritoneal cells) were cultured at 37° C. in a 5% $CO_2$ gassed atmosphere. Cells were maintained at a concentration between $5 \times 10^5$ and $1 \times 10^6$ cells/ml in RPMI 1640 media (PAA) supplemented with 10% (v/v) heat-inactivated FCS, 1% (v/v) PSG, 1% (v/v) Non-essential-Amino-Acids, 1% Sodium Pyruvate, 10 mM HEPES and 56 μM β-mercaptoethanol (splenocyte medium). Stocks in liquid nitrogen were prepared by freezing $5 \times 10^6$ cells/ml in FCS containing 10% DMSO. Samples were frozen in a freezing machine (Custom Bio Genic Systems) according to the manufacturer's recommendations and transferred to liquid nitrogen.

1.16 Staining of Primary B Cells for FACS Sorting

Peritoneal cells and erythrocyte-depleted splenocytes from 1.5-4 month old mice (C57BL/6J; Jackson Laboratories) were isolated. The cells were washed twice in FACS buffer (2% FCS in 1×PBS) and the pellet was resuspended in an appropriate volume of FACS buffer.

Cells from spleen and peritoneum were stained with antibody compositions which allow for the identification and isolation of B-1, follicular B (FO) and marginal zone (MZ) B cell subpopulations. For triple staining, optimized dilutions of fluorescein isothiocyanate (FITC)-, phycoerythrin (PE)-, and allophycocyanin (APC)-conjugated antibodies were used. To assure highly specific staining, all specific antibodies used were anti-mouse antibodies.

For unstained and single-stained reference samples, approximately $0.5 \times 10^6$ cells were taken out to each well of a round-bottomed 96-well plate. The remaining cells were transferred to FACS tubes. After centrifugation the pellets were resuspended and incubated for 10 min on ice in a 1:200 dilution of $F_cR$ (a-CD16/CD32) block in FACS buffer to target the $F_C$ receptors on myeloid and B lymphoid cells, which in non-blocked state unspecifically bind the antibodies employed for FACS analysis. The samples were centrifuged, the blocking solution was flicked out, and the cells were incubated in primary antibody in FACS buffer for 20-40 min on ice. The cells were washed three times in FACS buffer and, if necessary, with secondary antibody in FACS buffer for another 20-40 min on ice. After three washing steps cells were transferred into FACS tubes through a filter. After sorting, cells were washed once, and either cultured as described or the cell pellet was frozen at −80° C. If not stated differently, all FACS antibodies used were purchased from BD Pharmingen.

1.17 ELISA and ELISPOT

To investigate antibody secretion behavior in primary FO B cells with increased MZB1 protein levels, ELISA assays as well as ELISPOT experiments were performed. For ELISA, the infected and FACS sorted cells (GFP$^+$ cells) were plated on 24 well plates and incubated for up to three days in splenocyte medium in the presence or the absence of LPS stimulation (1 μg/ml). The concentration of secreted antibody was determined in supernatant isolated 6 h, 24 h, 48 h and 72 h after culture start using a standard IgM-specific ELISA protocol. Moreover, modified ELISA protocols specifically detecting polyreactive antibodies were carried out, testing whether an increase in MZB1 results in a shift of quality of the secreted antibody. To address potential limitations in the ability of an ELISA to detect the output of rare antibody secreting cells, ELISPOT assays which are able to detect every single cell secreting IgM were performed. ELISPOT assays were carried out on MultiScreen-HA filter plates (Millipore). GFP$^+$ cells were incubated for 6 h, 24 h, 48 h and 72 h at 37° C. on pre-coated 96-well filter plates in the presence or the absence of LPS stimulation (1 μg/ml) and developed with AP substrate, marking every antibody secreting cell with a blue spot on the filter. Spots were counted using specific software in order to identify possible differences in the number of antibody secreting cells between wt FO B cells and FO B cells overexpressing MZB1.

1.18 Generation of T Cell-Specific MZB1 Transgenic Mice: Lck-MZB1-M3, Lck-MZB1-F38 and Lck-MZB1-F47

The MZB1 transgenic construct was generated by inserting PCR-amplified mouse MZB1 genomic DNA into the BamHI site of the vector pick-hGH (Garvin et al., 1990), which contains the T-cell-specific lck proximal promoter and the human growth hormone (hGH) gene with introns and a polyadenylation signal. Plasmid DNA was linearized using a NotI restriction digest, followed by agarose gel extraction and microinjected into FVB-derived zygotes. Transgenic founders were identified by Southern blot analysis of the tail genomic DNA according to standard protocols. Three independent transgenic lines were established and backcrossed with C57BL/6J wt-mice. Transgenic offspring were determined by PCR of the tail genomic DNA with the transgene-specific primers. For various experiments, transgenic offspring and their wt littermates of the three independent lines were analyzed.

Figure 1:
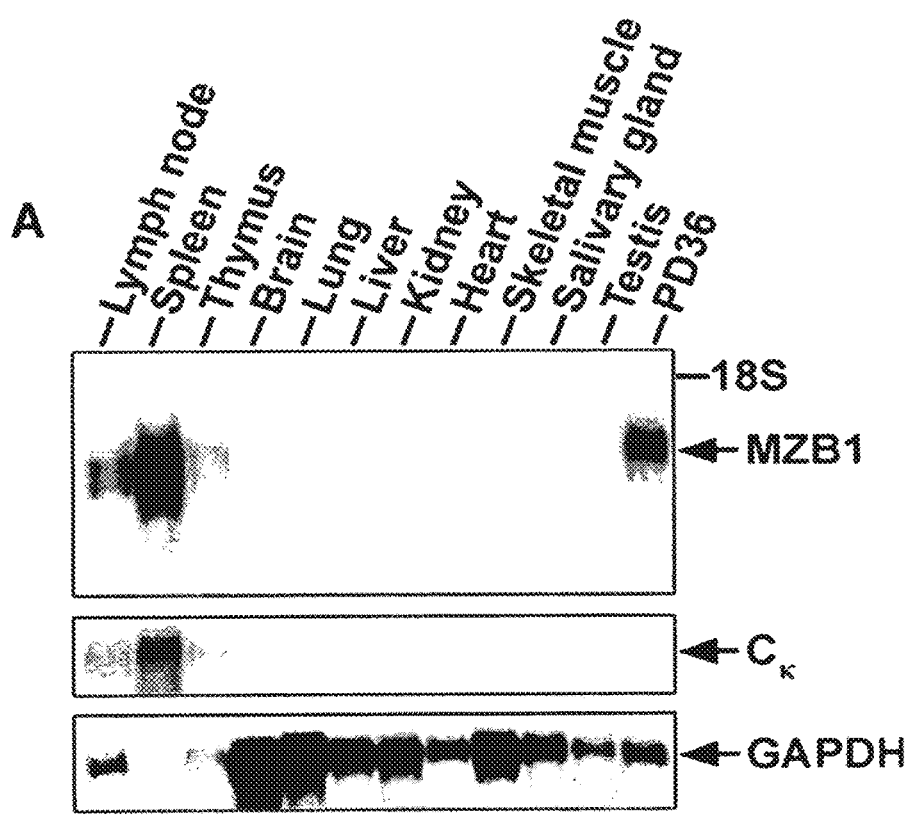
FIG. 1: Expression pattern of MZB1.
Figure 1:
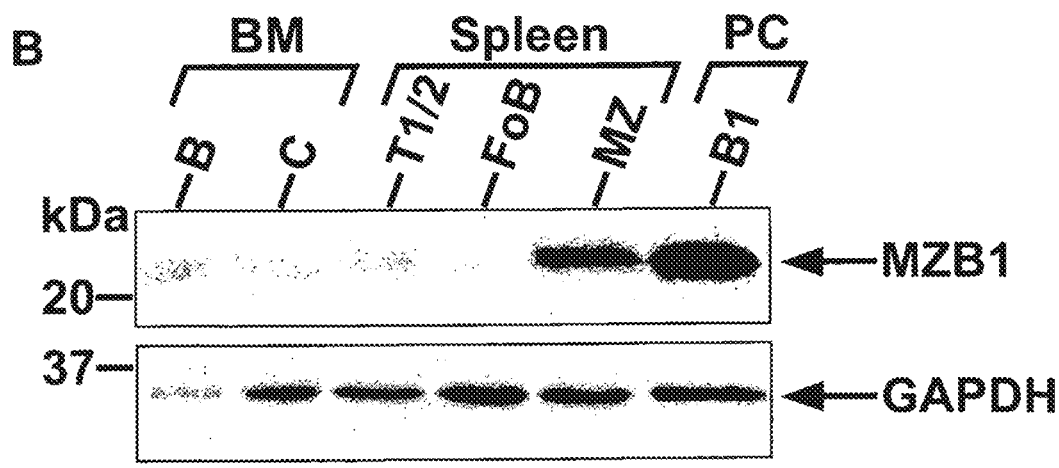

2. Results 2.1 Analysis of the Expression Pattern of MZB1 and its Subcellular Localization 2.1.1 MZB1 is Expressed Specifically in B Cells MZB1 was initially identified as a lymphoid-specific cDNA clone from a murine 70Z/3 pre-B cell bacteriophage library by differential screening. In vivo, MZB1 is present in secondary lymphoid tissues and the expression of MZB1 was found to be highest in the subpopulations of B cells, whilst only minor MZB1 expression was detected in FO B cells (FIGS. 1A+B). MZB1 mRNA was detected in cultured cell lines of all stages of B cell development including fetal liver- or adult bone marrow-derived pre-B, B and plasmacytoma cell lines, but absent from cell lines of the T, myeloid, fibroblastic or erythroid lineages. A tissue Northern blot analysis on poly-$A^+$ RNA from different mouse tissues revealed that MZB1 transcript is confined to tissues containing B cells, such as the spleen and lymph nodes.

To facilitate the analysis of MZB1 protein expression, four different rat monoclonal α-mouse MZB1 antibodies were generated. Immunohistochemistry and immunoblot analysis using these antibodies revealed abundant MZB1 protein in the spleen and peritoneum. The MZB1-expressing cells in these tissues are $B220^{dull}$ and $IgM^{high}$, indicating that they belong to a subset of activated B cells.

2.1.2 MZB1 Protein is Highly Expressed in Splenic Marginal Zone B Cells (MZ) and Peritoneum Derived B1 B Cells Different B cell populations originating from the bone marrow, spleen and peritoneal cavity (PC) were FACS-sorted and an MZB1 immunoblot analysis was performed on equal amounts of protein (FIG. 1B).

MZB1 expression is high in splenic MZ B cells and peritoneal cavity derived B1 B cells, but low to absent in the splenic follicular B cells (FO). The immature B cell subsets represented by bone marrow derived fraction B and C as well as splenic transitional 1 and 2 B cells (T1/2) display a moderate expression level of MZB1 protein (FIG. 1B), 2.1.3 Intracellular Localization of MZB1 Protein Computational analyses of the MZB1 amino acid sequence suggest that MZB1 contains a signal peptide targeting the protein to certain intracellular compartments and possibly to the secretory pathway. Furthermore, the MZB1 ORF contains a weak putative ER retention signal, raising the question whether MZB1 protein is retained in the endoplasmic reticulum (ER). To investigate the intracellular localization of MZB1, indirect immunofluorescence experiments, visualized with a confocal microscope, were performed using FACS-sorted MZ B cells (FIG. 2).

In primary MZ B cells, MZB1 protein was found to localize to the cytoplasm throughout the cytosol, around the nuclear envelope and the cytoplasmic membrane (FIG. 2: upper left and lower right panel). In some regions of the cell, MZB1 is restricted to a punctuate, cytoplasmic pattern, indicating that a fraction of the cellular MZB1 pool is retained in specific cytosolic compartments, likely the endoplasmic reticulum. MZB1 appeared to be entirely excluded from the nucleus (FIG. 2).

Since MZ B cells are very small in size, consisting of a predominant nucleus surrounded by a thin layer of cytoplasm, these cells are not optimal to study the localization of a cytoplasmic protein like MZB1 using confocal microscopy. To overcome these obstacles, indirect immunofluorescence experiments were performed using a NIH 3T3 murine fibroblast cell line stably expressing FLAG-MZB1. These MZB1-expressing fibroblastic cells are larger in size compared to MZ B cells and as they are widely spread on the surface, cellular compartments can be visualized more accurately using confocal microscopy (FIG. 3).

MZB1 was also found to be expressed in a punctuate, cytoplasmic pattern in NIH 3T3 FLAG-MZB1 cells (FIG. 3A, B), suggesting ER distribution. The nuclear membrane was stained as well.

An antibody specifically for BCR-associated protein of 31 kDa (BAP31), which is an ubiquitously expressed ER-localized polytopic membrane protein harboring three putative transmembrane (TM) regions, was utilized for visualizing the ER of NIH 3T3 FLAG-MZB1 cells (FIG. 3A, C). The comparison of the MZB1 and BAP31 staining patterns shown in FIG. 3 revealed a high degree of colocalization of the two proteins in the ER compartment surrounding the nucleus. In areas more distant from the nucleus, the staining patterns of MZB1 and BAP31 did not show a significant overlap (FIGS. 3A, B and C). In these parts of the cell, MZB1 appeared to be evenly dispersed within the cytosol. These results suggest the possible existence of at least two pools of MZB1 protein within the cell, one of which is localized to the ER whereas the other one is distributed in the cytosol. Furthermore, as in MZ B cells (FIG. 2), MZB1 staining was also found at the cytoplasmic membrane in NIH 313 FLAG-MZB1 cells (FIG. 3A, B), suggesting a possible association of MZB1 protein with the cell membrane.

Further experiments, using confocal microscopy in combination with nocodazole treatment of the cells (FIG. 4) as well as biochemical techniques, namely proteinase K digestion of subcellular fractions (FIG. 5), revealed the signal peptide and ER-retention motif containing protein MZB1 to be localized in the lumen of the endoplasmatic reticulum, most probably associated with the ER membrane.

2.1.4 MZB1 Protein is Associated with the Cell Membrane

To investigate the subcellular localization of MZB1 in more detail, cytosolic and membrane fractions of K46 cells were prepared by hypotonic cell lysis and subsequent ultracentrifugation. After resuspending the washed membranes in Nonidet-P40 (NP40) and sodium deoxycholate (DOC)-containing lysis buffer, an equal amount of protein from each fraction was used in an MZB1-specific immunoblot (Figures). To control for a possible cross contamination between the membrane fraction and the cytosolic fraction, a GAPDH- (cytosolic protein) and a BAP32-specific immunoblot were also performed. BCR-associated protein of 32 kDa (BAP32) is a highly conserved, ubiquitously expressed protein that mainly localizes to the mitochondrial membrane.

About 90% of total MZB1 was found to be in the cytosolic fraction in non-stimulated K46 cells. The remaining 10% of MZB1 was found to be associated with cellular membranes. The control immunoblots with antibodies specific for GAPDH and BAP32 revealed no cross contamination between of the two fractions (FIG. 6).

This result is in agreement with those obtained from MZB1 immunofluorescence experiments (FIGS. 2 & 3) that a small pool of MZB1 protein is associated with cellular membranes, likely the plasma membrane, whereas the majority of MZB1 is localized in the cytosolic of non-stimulated cells (FIG. 6).

To further characterize the subcellular localization of MZB1, BCR-stimulated K46 mature B cells were fractionated into cytosolic and membrane fractions (FIG. 7). The cells were serum-starved for 1 h and subsequently stimulated with 5 µg/ml α-kappa antibody (Southern Biotechnology) for 0 min, 1 min, 5 min and 20 min.

Consistent with the results presented in FIG. 6, in non-stimulated K46 B cells, the majority of MZB1 (70%) is present in the cytosolic fraction. Upon stimulation of the BCR with α-kappa, a significant amount of MZB1 is recruited to the membrane fraction, changing the ratio to 35% cytosolic and 65% membrane associated MZB1 (FIG. 7). An extension of the stimulus to 5 min or 20 min leads to a decrease in the amount of MZB1 associated with the membrane component, which is additionally revealed by a densitometric analysis of the immunoblot signals (FIG. 8). Since the amount of cytosolic MZB1 is kept nearly constant during the time course from 0 min to 5 min, it is likely that the weak MZB1 signal in the cytosolic fraction after 20 min of stimulation is caused by a poor transfer efficiency during the immunoblot procedure (FIG. 7). This would explain the recurrence of a switch to 33% cytosolic and 66% membrane-bound MZB1.

The subcellular fractionation of K46 cells into cytosolic and membrane components indicates that in non-stimulated cells, between 10% to 30% of the cellular MZB1 pool is associated with the membrane fraction. Upon BCR-stimulation, MZB1 protein is dynamically recruited to the membrane followed by a decrease in MZB1 membrane association after extended stimulation. These results are confirmed by immunofluorescence experiments, showing a weak staining of the cytoplasmic membrane in non-stimulated cells (FIG. 2, 3) and an evident recruitment of MZB1 to the cell membrane after BCR-stimulation.

2.2 Search for Interaction Partners 2.2.1 Yeast Two Hybrid Screen with MZB1

Apart from the biochemical complex purification, a high throughput screening in form of a yeast two hybrid screen to identify novel interaction partners of MZB1 was performed. Briefly, the bait protein, in this case MZB1, is fused to the Gal4 DNA-binding domain and binds to a promoter which has to be active in order to permit growth under selection conditions. A human B cell library as well as a human T cell library was cloned into an expression vector containing the Gal4 activation domain serving as a prey (Durfee et al., 1993). If bait and a potential interaction partner, the prey, come together, the Gal4 activation domain turns on transcription of a selection marker. The vector DNA of single clones can be isolated and sequenced.

For the screen, the murine cDNA of MZB1 was cloned into the yeast pGBT9 expression vector and obtained a number of clones which were isolated and sequenced (Tables 1 & 2).

TABLE 1

| Clones obtained from T cell library: | |
|---|---|
| Definition | Number of clones |
| RACK1 (Receptor for activated C kinase; Lung cancer oncogene 7) | 17 |
| Serpinpeptidase-inhibitor (Ovalbumine) | 1 |
| Dehydrogenase/reductase 1 (SDR-family) | 1 |
| Methylenetetrahydrofolate dehydrogenase (NADP + dependent) | 1 |
| Succinate dehydrogenase complex | 1 |

TABLE 2

| Clones obtained from B cell library: | |
|---|---|
| Definition | Number of clones |
| RACK1 (Receptor for activated C kinase; Lung cancer oncogene 7) | 10 |
| Immunoglobulin µ heavy chain | 3 |
| RUNX3 (Runt-related transcription factor 3; PEBP2aC1; AML2) | 1 |
| Ku70-binding protein 3 | 1 |
| Nascent-polypeptide-associated complex alpha polypeptide (α-NAC) | 1 |
| Component of oligomeric golgi complex 4 | 1 |

Among the potential interaction partners obtained in two independent yeast two hybrid screens using a human T cell library or a human B cell library, one protein, namely "receptor for activated C kinase" (RACK1) turned out to be predominant. RACK1, a scaffolding protein consisting of 7 WD40 repeats is an especially interesting protein by virtue of its ability to coordinate the interaction of key signaling molecules and hence playing a central role in the organization of critical biological processes like the regulation of proliferation, cell cycle and cell adherence (McCahill et al., 2002). Interestingly, the two independent yeast two-hybrid screens did not yield BIP as a potential interaction partner of MZB1 which could be explained by the fact that GRP78 was not present or underrepresented in the used libraries. Due to their small numbers of clones detected in the screen, the remaining hits were neglected.

2.2.2 MZB1 Interacts with RACK1 and PKCβ in the Membrane Fraction of K46 Cell Extracts In order to confirm the results of the yeast two-hybrid screen, co-immunoprecipitation experiments were carried out. In a first attempt to verify the results obtained from the yeast two hybrid screen, standard CoIP conditions (Standard CoIP buffer freshly supplemented with 1×PMSF, 1× Sodium orthovanadate, 1×PIM and 1×NaF) with whole cell extracts of BCR stimulated and untreated K46 B cells were used to demonstrate a potential interaction between MZB1 and RACK1 following the standard co-immunoprecipitation protocol. Immunoprecipitation of both endogenous proteins with their specific antibodies revealed direct IP signals but co-immunoprecipitation was, however, hardly detected for both cases (data not shown). Furthermore, it was analyzed whether the interaction of MZB1 and RACK1 was restricted to the membrane compartment. It was thought that the separation of whole cell extracts into a membrane and a cytosolic compartment would enrich the potential protein complex in the subcellular fraction where it is located and so facilitate detection. Membrane and cytosolic extracts of K46 B cells were prepared as described before. CoIP was carried out using, per single IP, 1 mg of total protein and either 3 µg of α-RACK1 antibody (BD Biosciences) or 40 µl of a 50% mixture of CNBr-activated Sepharose-beads (GE Healthcare) directly coupled to α-MZB1 antibody (clone 5011) or α-BCL9 control antibody.

As can be seen in FIG. 9, the direct IP signal for RACK1 and MZB1 could be detected in the cytosolic as well as the membrane fraction of K46 B cells. The co-immunoprecipitation (co-IP) signal for both RACK1 and MZB1 was absent from the cytosolic but present in the membrane fraction (FIG. 9). Taken together, the co-immunoprecipitation results described here confirm the interaction between MZB1 and RACK1 suggested from the yeast two-hybrid screens performed with a human B cell and T cell library (Tables 1 & 2). Furthermore, the separation of K46 whole cell extract into a cytosolic and a membrane fraction reveals that the MZB1-RACK1 association is restricted to the membrane compartments of the cell (FIG. 9). These results are in accordance with the finding that in non-stimulated K46 cells, approximately 10% of MZB1 protein is associated with cellular membranes (FIGS. 6 & 7). The membrane pool of MZB1 seems to be associated with the membrane pool of RACK1. Moreover, to confirm the association of MZB1 and RACK1 in a further set of experiments, FRET (Fluorescence Resonance Energy Transfer) microscopy analysis was performed, suggesting a direct interaction between MZB1 and RACK1 (data not shown), Since RACK1 was shown to interact, amongst various other proteins, with protein kinase C (PKCβ) (Ron et al., 1994), co-IP experiments precipitating PKCβ from cytosolic as well as membrane extract derived from non-stimulated K46 B cells were performed. The procedure for preparation of cytosolic and membrane fraction as well as the protocol for the immunoprecipitation were the same as the α-MZB1 and α-RACK1 IPs described above. Per single IP, 1 mg of total protein and 3 µg of α-PKCβ antibody (BD Biosciences) were used.

As revealed in FIG. 10, RACK1 and PKCβ interact with each other in the cytosolic as well as the membrane fraction of K46 B cells, confirming the already published association of the two proteins (Ron et al., 1994). In accordance with the results of the IPs performed with α-MZB1 and α-RACK1 antibodies, a co-IP signal for MZB1 was detected in the membrane but was absent from the cytosolic fraction.

In summary, these results indicate an interaction of MZB1 with RACK1 and MZB1 with PKCβ in the membrane compartment of non-stimulated K46 B cells (FIGS. 9 & 10), suggesting the formation of a ternary complex consisting of MZB1, RACK1 and PKCβ. The association between MZB1 and BiP was shown to be destabilized upon BCR stimulation. It remains to be tested whether the stability of the interaction between MZB1 and RACK1 or between MZB1 and PKCβ is affected by BCR stimulation. The fact that the interaction of MZB1, RACK1 and PKCβ is restricted to the membrane fraction is consistent with the observation that the complexed form of MZB1, which elutes at 220 kDa in gel filtration experiments, is found specifically in the membrane compartment but not the cytosolic compartment of a whole cell extract (data not shown).

2.2.3 ERp57, GRP94, ERp44 and BiP are Potential Interaction Partners of MZB1

In a further search for potential interaction partners of MZB1, K46 cells were either kept untreated or crosslinked with 1% formaldehyde prior to cell lysis. Using MZB1-specific antibodies, MZB1 protein was immunoprecipitated from both crosslinked as well as untreated cell extracts, and a 4%-12% gradient SDS-PAGE followed by a silver stain was performed. Bands, specifically appearing in the lane corresponding to the crosslinked cell extract, were excised and analyzed by mass-spectrometry (FIG. 11). Besides BiP, which was shown in previous experiments to interact with MZB1, the potential novel interaction partners, namely GRP94 (Endoplasmin), ERp57 and ERp44, being identified in the mass-spectrometry analysis, were confirmed to interact with MZB1 by co-immunoprecipitation experiments, using antibodies generated against the endogenous proteins (FIGS. 12 & 13).

ERp44: Interestingly, ERp44, a thioredoxin (TRX) family protein has not only been implicated in oxidative protein folding, but has as well been shown to specifically bind to the ER-luminal L3V domain of the inositol 1,4,5-trisphosphate receptor 1 (IP$_3$R1), hence inhibiting the Ca$^{2+}$-channel activity of the IP$_3$R1 in a pH-, redox state-, and [Ca$^{2+}$]$_{ER}$-dependent manner. The interaction of MZB1 with ERp44 raises the possibility that MZB1 might affect ER calcium stores (FIGS. 32, 35 & 36A) through the ER-membrane localized Ca$^{2+}$-channel IP$_3$R1.

ERp57: Supporting the notion of a calcium sensitive high molecular weight MZB1 complex, the interaction of ERp57 and MZB1 was shown to be calcium dependent (FIGS. 14 & 15A). Since ERp57, which belongs to the class of protein disulfide isomerases (PDI), was shown to regulate SERCA pump activity in a calcium dependent manner, it could be speculated whether MZB1 might be involved in the regulation of SERCA pump activity via ERp57, explaining the observed effects of MZB1 on ER calcium stores. Furthermore, size exclusion chromatography experiments revealed that both MZB1 and ERp57 co-migrate at an approximate molecular weight of 220 kDa in the absence of calcium, and both shift to lower molecular weight fractions if calcium was added to a final concentration of 2.5 mM to K46 membrane extracts (FIG. 16).

GRP94: On the contrary, for GRP94, belonging together with BiP to a multi-chaperone complex, responsible for the correct folding of cell surface proteins like various integrins as well as the Toll like receptor 4 (TLR4), its MZB1 interaction was shown to be calcium independent (FIGS. 14 & 15B). This fact raises the possibility of an alternative, ER-localized protein complex comprising amongst others of GRP94, BiP and MZB1. Interestingly, the cell surface expression of α4 and β1 integrins was reduced in K46 siRNA cells, whereas β2 surface expression was almost unchanged if compared to K46 wt and K46 siRNA::MZB1 cells (FIG. 17). Thus, MZB1 affects cell-surface expression of integrins on K46-siRNA cells. Considering the fact that the inducible knock out of GRP94 in B cells shows specific defects in the folding of integrins and the TLR4, MZB1, belonging to the same multi-chaperone complex like GRP94, might be a potential regulator of integrin folding. This hypothesis is further supported by some modest changes in TLR4 and integrin surface expression on MZB1-transduced FO B cells, compared to Mock-transduced control FO B cells (FIG. 18). Thus, MZB1 affects cell-surface expression of integrins and TLR4 on MZB1-transduced FO B cells.

2.2.4 the 220 kDa MZB1 Protein Complex is Calcium Sensitive

Cytosolic and membrane extracts of K46 mature cells were prepared in the presence and in the absence of Ca$^{2+}$. The above-described (section 2.2.2) high molecular weight MZB1 protein complex (220 kDa), which is specifically found in the membrane fraction of K46 B cells, was separated by gel filtration, followed by an immunoblot analysis (FIGS. 19 & 20). As shown in FIG. 20, the MZB1 protein complex was disrupted if 2.5 mM CaCl$_2$ was added prior to cell lysis and membrane fraction preparation. These results show that the high molecular weight MZB1 protein complex (220 kDa) is calcium sensitive.

Taken together, the subcellular localization of MZB1 in the ER, and the presence of a calcium-sensitive high molecular weight complex, indicate that MZB1 might be involved in the regulation of ER calcium stores, which are as well critical for the modulation of, e.g., BCR signalling and cell activation.

2.3 Functional Analysis of MZB1: Loss of Function 2.3.1 Generation of MZB1 Knock-Down B Cells as a Tool to Study MZB1 Functions In Vitro ShRNA was used to knock down MZB1 expression in K46 mature B cells in order to investigate the effects of reduced MZB1 protein levels on cell proliferation and BCR signaling capacity. Oligonucleotides were designed using the freely accessible "BD-RNAi design" (Beckton Dickinson) and "Block-iT RNAi" (Invitrogen) programs. The two most highly rated oligonucleotides from each prediction program, # inv2: GCGAAAGCAGAGGCTAAAT (SEQ ID NO: 14), # inv3: GCAGTCCTATGGAGTTCAT (SEQ ID NO: 15), # BD1: CCAGATCTATGAAGCCTAC (SEQ ID NO: 16), and # BD4: CTGCCACTGTTGCTACTGT (SEQ ID NO: 17) (all sequences listed are target sequences), were ordered and cloned into the pSuper RNAi system (Oligo Engine) which allows for the transcription of small hairpin RNAs (shRNA). All four oligonucleotides target the coding region of MZB1 and were tested in transient transfection assays in K46 cells. ShRNA # inv2 knocked down MZB1 mRNA levels to 16.5% of the wild-type (wt) expression level, whereas the other shRNAs were less effective (# inv3: 28.7%; # BD1: 36.1%; # BD4: 30%). The shRNA constructs additionally contain the GFP coding sequence, the expression of which allows for cell sorting, as well as a neomycin resistance cassette, which enables the selection of cells that have stably integrated the exogenous construct. The construct pSuper.neo+GFP+inv2 containing the shRNA # inv2 was transfected into K46 mature B cells and single cell clones were generated using FACS sorting followed by selection with neomycin. MZB1 protein levels of individual clones were determined using immunoblot analysis and four clones with significantly reduced MZB1 protein levels were identified, one of which is displayed representatively in FIG. 21 (lane 2). The differences in the extend of MZB1 knockdown observed between different clones were likely due to the integration sites of the constructs.

Two stable K46 clones transfected with pSuper.neo+GFP+inv2, # inv2-29 and # inv2-10, which had the strongest downregulation of MZB1-protein levels, were used to investigate the phenotype of MZB1 loss-of-function.

In order to restore MZB1 expression in shRNA clones # inv2-29 and # inv2-10, cells were transfected with the "rescue" plasmid pIRES-MZB1-mut-puro which drives the expression of a mutated version of MZB1 which is not affected by the MZB1-specific shRNA stably expressed by pSuper.neo+GFP+inv2. The bulk transfected population was selected simultaneously with puromycin and neomycin according to standard conditions. In all experiments performed, K46 shRNA cells (shRNA) were compared with the corresponding "rescued" clone (shRNA+MZB1) and K46 cells stably transfected with the empty vector pSuper.neo+GFP referred to as "wt" (wild-type). All experiments were carried out with clone # inv2-29, # inv2-10 and their corresponding "rescued" cells with restored MZB1 expression. Since similar results were obtained for # inv2-29 and # inv2-10, results obtained with clone # inv2-29 and its correlated "rescued" clone are displayed unless otherwise indicated.

The immunoblot analysis of MZB1 protein levels reveals a reduction by approximately 95% in shRNA cells compared to the wt (FIG. 21, lanes 1+2), indicating a successful knock down of MZB1. In shRNA+MZB1 cells, the level of MZB1 protein was comparable to the wt level, suggesting a full restoration of MZB1 protein levels in the "rescued" cells (FIG. 21, lanes 1+3).

2.3.2 Knock Down of MZB1 Enhances Proliferation but does not Influence Apoptosis Right after establishing the different lines in cell culture, it was observed that the shRNA cells proliferated significantly faster compared to their wt and "rescued" counterparts, making it necessary to split them more often. In order to directly assess the role of MZB1 in cell proliferation, growth assays with wt, shRNA and shRNA+MZB1 cells were performed. Equal numbers of cells ($1.0 \times 10^5$ cells per well) were plated and incubated for 72 hours at 37° C. following the previously described cell culture protocol. Cell numbers were determined using a CASY® cell counter (CASY®-technology) after 0 hours, 26 hours and 72 hours after plating (FIG. 23).

As depicted in FIG. 23, 26 hours after plating, when the culture was presumably at the end of the lag-phase of growth, there was a slightly higher number of shRNA cells than the wt and shRNA+MZB1 cells. After 72 hours in culture, in the middle of the exponential growth phase, there were significantly more shRNA cells than wt (3-4 fold) and shRNA+MZB1 cells (~6 fold). These results indicate that the reduction in MZB1 protein level in a fast proliferating B cell line either increases the number of cell divisions or decreases the rate of apoptosis. Since the determination of cell numbers using the CASY® cell counter (CASY®-technology) did not reveal a change in the percentage of dead cells between the three tested lines (data not shown), the reduction of MZB1 protein most probably affects proliferation. This hypothesis would be consistent with the fact that the scaffolding protein RACK1, which interacts with MZB1 in the membrane fraction of K46 cells (FIG. 9), was shown to play a central role in the organization of critical biological processes, such as the regulation of proliferation and cell cycle progression (McCahill et al., 2002).

In order to verify the results obtained from the cell growth experiment presented in FIG. 23, cell proliferation was additionally measured using [$^3$H]thymidine incorporation. BCR-stimulated as well as non-stimulated wt, shRNA and shRNA+MZB1 cells were pulse-labeled with 1.5 µCi/well of [$^3$H]thymidine for 16 h, and the mean [$^3$H]thymidine incorporation of triplicate cultures was assayed by scintillation counting.

Confirming the results of the growth assay (FIG. 23), non-stimulated K46 shRNA cells had an increased rate of proliferation compared to wt (~8 fold) and shRNA+MZB1 (~3 fold) cells (FIG. 24). Upon BCR stimulation by the addition of 5 µg/ml α-kappa antibody (Southern Biotechnology), wt, shRNA and shRNA+MZB1 cells responded with equal proliferation rates to the stimulus. Whereas the wt and the "rescued" cells displayed a remarkable increase in cell proliferation upon BCR stimulation, the cell proliferation rate of K46 shRNA cells stayed almost unchanged (FIG. 24). In other words, non-stimulated K46 shRNA cells exhibit a comparably high proliferation rate like BCR-stimulated wt and "rescued" cells, suggesting a possible pre-activated state of cells with reduced MZB1 protein levels. Furthermore, both the growth assay as well as the [$^3$H]thymidine incorporation experiments demonstrate a restoration of the wt proliferation phenotype in shRNA cells with re-established MZB1 protein levels (shRNA+MZB1 cells) (FIGS. 23 & 24).

Newly thawed clones of K46 wt cells stably transfected with pSuper.neo+GFP and shRNA cells stably transfected with pSuper.neo+GFP+inv2 were monitored by FACS and the GFP+ cells were enriched by FACS sorting. A representative FACS profile for freshly thawed wt and shRNA cells is depicted in FIG. 25. Generally, only the GFP$^{high}$ cells, from both K46 wt and K46 shRNA cells, are FACS sorted and maintained in selection media. For certain experiments, only the GFP$^{high}$ wt cells were isolated, whereas both the GFP$^{high}$ and the GFP$^{intermediate}$ shRNA cells were sorted and maintained separately (FIG. 25). The GFP$^{high}$ cells (shRNA- GFP-high) should have a more pronounced reduction in MZB1 protein level than the GFP$^{intermediate}$ cells (shRNA-GFP-int cells).

Indeed, an immunoblot analysis carried out with α-MZB1 specific antibodies reveals a correlation between GFP-expression and MZB1-attenuation in the two isolated and separately maintained populations of shRNA cells. Whereas the shRNA-GFP-high cells show a marked reduction in MZB1 protein level, the shRNA-GFP-int population displays a midway down regulation of MZB1 protein (FIG. 26). The reduction of MZB1 protein level in the shRNA-GFP-high cells in this particular experiment is not as pronounced as in the shRNA cells used for other analyses (FIG. 21). This might be caused by contamination of the shRNA-GFP-high cells with shRNA-GFP-int cells due to the close proximity of the two gates.

To address the question whether MZB1 influences cell proliferation in a dosage-dependent manner, [$^3$H]thymidine incorporation experiments with non-stimulated as well as BCR-stimulated wt, shRNA-GFP-int and shRNA-GFP-high cells were performed as described above. In the non-stimulated situation, shRNA-GFP-high cells cycled 2-3 fold faster compared to the K46 wt cells (FIG. 27). The proliferation rate of the non-stimulated shRNA-GFP-int cells was in between the that of the wt and the shRNA-GFP-high cells (FIG. 27). These results indicate a dosage-dependent effect of the MZB1 protein on cell proliferation and confirm the finding that the reduction of MZB1 in non-stimulated B cells promotes cell division (FIGS. 23, 24 and 27). Similarly to previous observation (FIG. 24), the proliferation rate of shRNA-GFP-high cells stayed nearly constant upon BCR stimulation by the addition of α-kappa antibody (Southern Biotechnology) in a concentration of 5 μg/ml. In contrast, both the wt and the shRNA-GFP-int cells displayed an increase in proliferation upon α-kappa stimulation (FIG. 27). The increase was more prominent in case of the wt cells (2-3 fold) than shRNA-GFP-int cells (1.5 fold) (FIG. 27). These results further strengthen the notion that cells with reduced MZB1 protein levels are in a pre-activated state. Lastly, the fact that the reduction of MZB1 protein level in the shRNA-GFP-high cells in the present experiment was not as pronounced as in shRNA cells in the previous experiment (FIG. 24) most likely accounts for the reduced difference observed in proliferation rate between wt and shRNA cells in the present experiment (FIG. 24: 8 fold vs. FIG. 27: 2-3 fold).

In order to confirm that MZB1 influences proliferation and not apoptosis, K46 wt and K46 shRNA cells were stained with Annexin V and 7-amino-actinomysin (7-AAD).

Annexin V staining of non-stimulated K46 wt and shRNA cells revealed no significant difference in apoptosis (FIG. 28). The majority of cells (approximately 90%) is viable, negative for both Annexin V and 7AAD. A small population of cells, ranging from 5% (shRNA) to 6% (wt) are slightly Annexin V-positive, indicating that these cells entered the early stages of apoptosis. The percentage of dead cells lies in a range of 2% in both the wt and the shRNA populations. These results indicate that a reduction in the MZB1 protein level in K46 mature B cells, at least in the non-stimulated situation, does not affect apoptosis.

In summary, the RNA interference-mediated downregulation of MZB1 expression in K46 mature B cells led to an increase in cell division (FIGS. 23, 24 and 27) without affecting apoptosis (FIG. 28). Upon downregulation of MZB1 protein level, the cells exhibited a pre-activated state displaying a proliferation rate which is comparable to BCR-stimulated wt K46 cells (FIG. 24). Moreover, this hyper-proliferative, pre-activated phenotype appeared to be MZB1 dosage-dependent, being more pronounced in cells expressing less MZB1 (FIG. 27). Furthermore, MZB1 interacts with RACK1, a scaffolding protein coordinating the interaction of key signaling molecules such as c-Src and other Src-family kinases (McCahill et al., 2002), and with PKCβ which is a critical component of the BCR signaling machinery (Leitges et al., 1996). MZB1 is likely brought into to the BCR signaling machinery via the formation of a ternary complex with RACK1 and PKCβ, thereby exerting its influence on proliferation and cell cycle progression. Taken together, MZB1 plays a role in the regulation of cell proliferation in non-stimulated K46 mature B cells.

2.3.3 Downregulation of MZB1 Expression Increases Calcium Signalling

In resting B cells, the concentration of free intracellular $Ca^{2+}$ is kept low and constant. Engagement of the BCR, and hence activation of the cells, results in the recruitment of adaptor molecules such as SLP65 and kinases like Lyn, Syk or Btk, which ultimately results in tyrosine phosphorylation of phospholipase C-γ (PLC-γ) and an increase in intracellular $Ca^{2+}$. The key step in triggering $Ca^{2+}$ flux is the activation of PLC-γ, which hydrolyzes phosphatidylinositol-4,5-bisphosphate ($PIP_2$) to diacylglycerol (DAG) and inositol-1,4,5-trisphosphate ($IP_3$). $IP_3$ binds to $IP_3$ receptors ($IP_3Rs$) in the endoplasmic reticulum (ER) and induces the release of $Ca^{2+}$ into the cytoplasm. The depletion of $Ca^{2+}$ from intracellular stores triggers entry of $Ca^{2+}$ across channels in the plasma membrane, commonly referred to as calcium release-activated $Ca^{2+}$ (CRAG) channels or store-operated channels. The ensuing sustained intracellular $Ca^{2+}$ elevation activates transcriptional pathways required for proliferation and effector immune function, both of which are hallmarks of activated lymphocytes. The intracellular $Ca^{2+}$ is hence a benchmark for the strength of the received signal and consequently an indicator for the cellular activation status. Since the reduction of MZB1 protein level in K46 mature B cells was shown to increase proliferation which is a characteristic of BCR-activated cells, and since MZB1 is likely associated with the BCR signaling machinery via its interaction partners RACK1 and PKCβ, it is hypothesized that MZB1 also affects calcium signaling. Consequently, $Ca^{2+}$ release following BCR engagement was compared in wt, shRNA and shRNA+MZB1 K46 cells. Relative levels of intracellular $Ca^{2+}$ were measured by FACS analysis of Indo-1 AM (Molecular Probes) loaded cells. $Ca^{2+}$-response was induced by adding mouse specific goat α-kappa antibody (Southern Biotechnology) at a final concentration of 5 μg/ml. The $Ca^{2+}$-concentration of the RPMI-media used was either unchanged (2 mM) or diluted to 0.5 mM in order to simulate limited extracellular $Ca^{2+}$ availability.

Under conditions with restricted extracellular $Ca^{2+}$ (0.5 mM), a significant increase in $Ca^{2+}$ mobilization upon BCR stimulation was observed in MZB1 shRNA cells compared to wt and shRNA+MZB1 cells (FIG. 29). The wt and the shRNA+MZB1 cells exhibited comparable BCR stimulation-induced $Ca^{2+}$ flux, demonstrating the restoration of the wt phenotype in shRNA cells by re-establishing MZB1 protein level (FIG. 29). Similar results were obtained under non-limiting extracellular $Ca^{2+}$ conditions (2.0 mM) (FIG. 30).

In order to rule out the possibility that the reduction of MZB1 protein levels in K46 cells, which express membrane bound $IgG_{2a}$/kappa (Kim et al., 1979), increases the amount of cell-surface BCR molecules which then leads to the observed increase in $Ca^{2+}$ mobilization, surface BCR expression in K46 wt and K46 shRNA cells was monitored. The analysis was performed using the same freshly thawed clones presented in FIG. 25.

Almost all GFP+ K46 wt cells express a kappa-light chain-containing BCR on their cell surface; in contrast, only 70% of the shRNA cells are kappa+ (FIG. 31). Whether the remaining 30% of the shRNA cells express no BCR on their surface and whether the interaction of MZB1 with the lumenal ER chaperone BiP is responsible for this phenotype need to be further investigated. The fact that the mean fluorescence intensity of the kappa+ populations among the wt and the shRNA cells is comparable rules out the possibility that the increased Ca+ mobilization in the shRNA cells is caused by a higher number of surface BCRs.

In summary, a decrease in MZB1 protein level leads to an increase in $Ca^{2+}$ flux upon BCR engagement in K46 mature B cells (FIG. 29, 30), indicating that the reduction of MZB1 expression prompts a more pronounced intracellular signal and hence a stronger activation of the cell following BCR ligation. Together with the results from the proliferation experiments described above, these results suggest that MZB1 plays a negative regulatory role in BCR-mediated signaling, likely via its interaction with RACK1 and PKCβ.

Figure 33:
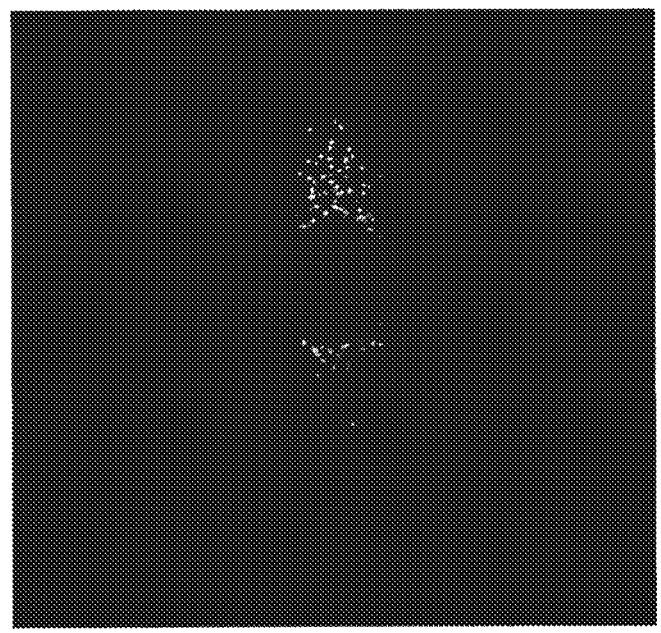
Figure 33:
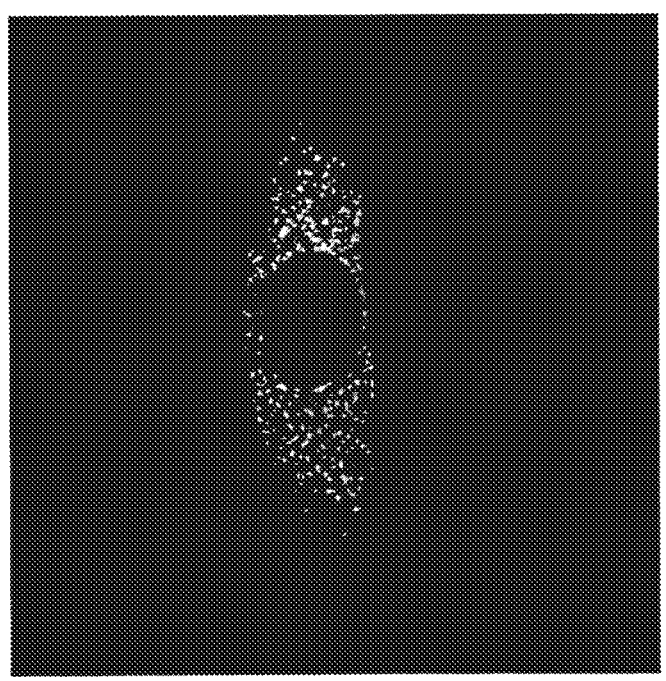

2.3.4 MZB1 Acts as a Potential Regulator of Intracellular $Ca^{2+}$ Stores in K46 Cells As studies with K46 MZB1siRNA cells revealed an influence of MZB1 on calcium mobilization following BCR stimulation, a subsequent set of experiments should explore whether MZB1 might participate in the more basic regulation of ER calcium stores. To address this issue, store operated calcium entry (SOCE) was induced, stimulating K46 wt, siRNA and siRNA::MZB1 cells with thapsigargin prior to addition of calcium to a final concentration of 5.0 mM $CaCl_2$. Thapsigargin is a specific inhibitor of the SERCA ATPase, which refills ER calcium stores and keeps the ER calcium concentration at a significantly higher level compared to the cytosolic calcium concentration. Due to inhibition of the SERCA pump the ER calcium concentration decreases within minutes, Stim proteins are activated and calcium is taken up into the cell over plasma membrane located calcium release-activated $Ca^{2+}$ (CRAG) channels, which are regulated by Stim proteins. FIG. 32 shows the $Ca^{2+}$-mobilization in MZB1-siRNA cells upon thapsigargin treatment. As seen in FIG. 32, the thapsigargin induced SOCE is significantly higher in K46 siRNA cells compared to K46 wt and K46 siRNA::MZB1 cells, suggesting that MZB1 might be part of the machinery regulating cellular calcium flux (FIG. 32). This notion is further corroborated by the fact that the MZB1 protein seems to behave similar like Stim proteins, aggregating at ER-plasma membrane junctions following a thapsigargin-induced decrease in ER calcium concentration, which could be shown by live cell imaging using MZB1-GFP fusion protein expressing NIH3T3 fibroblasts: FIGS. 33 and 34 show that MZB1 redistributes into punctuate structures after ER $Ca^{2+}$ store depletion. Furthermore, the measurement of ER calcium concentration, using the calcium ionophore ionomycin, revealed a significant increase in ER $Ca^{2+}$ stores in K46 siRNA cells, compared to K46 wt and K46 siRNA::MZB1 cells, confirming the potential role of MZB1 as a modulator of cellular calcium stores, especially ER calcium stores (FIG. 35: Mobilization of ER-$Ca^{2+}$ stores in MZB1-siRNA cells upon ionomycin treatment). Interestingly, if the MZB1 protein is overexpressed in FO B cells, the ER calcium store is found decreased in comparison to MOCK-transduced FO B cells (FIG. 36: Mobilization of ER-$Ca^{2+}$ stores in MZB1-overexpressing FO B cells upon ionomycin treatment), supporting the data observed in the knockdown-studies.

2.3.5 Downregulation of MZB1 Reduces Antibody Secretion in B1/MZ B Cells

Primary B1 B cells and MZ B cells were transduced with retrovirus GP+E86-miRNA-MZB1 or GP+E86-MCS; the transduced cells were enriched by FACS sorting for GFP+ cells. MZB1 expression level in the transduced cells was determined using a MZB1-specific antibody in an immunoblot analysis. MZB1 expression level was found to be reduced in cells transduced by GP+E86-miRNA-MZB1 ("the miRNA-cells") than cells transduced by GP+E86-MCS ("the control cells") (data not shown). IgM production from LPS-stimulated miRNA cells and the control cells is determined by ELISA.

2.3.6 Generation and Characterization of MZB1 Knock-Out and Conditional Knock-Out Mice MZB1 knock-out (KO) and conditional knock-out mice can be used to study the role of MZB1 in the regulation of BCR signalling and cell proliferation. The proliferation of non-stimulated MZ and B-1 B cells from wild-type (WT) and knock-out (KO) mice can be determined in a [$^3$H]-thymidine incorporation experiment and compared. Furthermore, $Ca^2$E release following BCR stimulation can be measured in MZ and B-1 B cell populations obtained from KO and WT animals. MZB1 KO and conditional KO mice can also be used to investigate the differences between MZ and B1 B cells on the one hand and FO B cells on the other hand. The effect of the inactivation of the mzb1-gene on the development and/or homeostasis of MZ and/or B-1 B cells can also be examined. Furthermore, the analysis of MZB1 KO and conditional KO animals will also shine light onto the role of MZB1 in autoimmunity, in particular, the secretion of (auto-) antibodies.

2.4 Functional Analysis of MZB1: Gain of Function 2.4.1 Overexpression of MZB1 in Follicular B Cells Results in Reduced Proliferation Follicular (FO) B cells were isolated from 1.5-4 month old mice according to their cell surface markers as B220+, $CD21^{int}$ and $CD23^{hi}$ cells by FACS sorting, following standard protocols. The isolated follicular B cells were resuspended in splenocyte media containing 2 µg/ml polybrene and co-cultured for 36 h on a confluent packaging cell feeder-layer, either producing an MZB1- and GFP-expressing (GP+E86-MZB1) or a solely GFP-expressing retrovirus (GP+E86-MCS; MOCK control). Transduced, GFP+FO B cells were enriched by FACS-sorting.

An immunoblot analysis carried out with MZB1- as well as GAPDH-specific antibodies revealed a significant MZB1-overexpression in FO B cells transduced with the MZB1-expressing vector in comparison to MOCK transduced control FO B cells (FIG. 51). In order to address the question whether MZB1 overexpression in primary follicular B cells affects cell proliferation, [$^3$H]thymidine incorporation assays were performed. Briefly, utilizing a 96 well format to determine the relative rate of radioactive [$^3$H]thymidine assimilation, reflecting the rate of proliferation, non-stimulated MZB1- and MOCK-transduced follicular B cells were pulse-labeled with 1.5 µCi/well for 18 h and the mean [$^3$H] incorporation of triplicate cultures was assayed by scintillation counting.

In non-stimulated primary B cells, MZB1 overexpression resulted in an approximately three fold downregulation of the proliferation rate (FIG. 52), which is consistent with the results of the loss of function analyses using shRNA and miRNA. These results suggest that MZB1 is a putative negative regulator of BCR-signaling and as a consequence, influences cell proliferation in the absence of BCR engagement.

2.4.2 Overexpression of MZB1 in Follicular B Cells Results in Enhanced Secretion of IgM Upon LPS Stimulation In Vitro Follicular B cells that normally express very low levels of MZB1 protein were forced to express MZB1 robustly via retroviral infection. Upon infection, the cells were stimulated with LPS that drives B cell differentiation into antibody secreting cells. The levels of secreted IgM were assessed in the cell culture supernatant using an ELISA assay.

Significantly higher secretion of IgM was observed on the third day of stimulation with LPS (FIG. 38). The third day of plasma cell differentiation in vitro is the time when most of the cells have differentiated into antibody secreting cells and the antibody secretion is the highest.

This result suggests that MZB1 positively regulates antibody secretion in B cells.

2.4.3 Generation and Characterization of MZB1 Transgenic Mice

The expression level of MZB1 varies during B cell development in different B cell subsets. The highest expression of MZB1 is found in marginal zone (MZ) B cells and B1 B cells. Very low expression is observed in resting follicular (FO) B cells. However, the level of MZB1 expression increases drastically upon the onset of plasma cells differentiation of FO B cells. Two transgenic mouse models were generated, one in which MZB1 overexpression is constitutive and the other in which MZB1 overexpression is inducible, to study the effects of MZB1 overexpression on B cell development, B cell function, B cell homeostatsis, in particular, self-renewal, and the development of autoimmunity.

To generate transgenic mice with constitutive MZB1 overexpression, a transgene construct containing the MZB1 coding sequence under the control of B29 promoter and Eμ enhancer which are active in B cells is linearized and microinjected into the pronuclei of fertilized eggs. Alternatively, a transgene construct containing the MZB1 coding sequence under the control of the kappa chain promoter is used.

To generate transgenic mice with inducible MZB1 overexpression, two strains of transgenic mice were used. One transgenic strain, NLS-TmA, carries a transgene containing the Tet transactivator constitutively expressed from the R26 locus. A second transgenic strain carries a transgene (ptet-MZBpa) containing the Tet operator fused upstream to the MZB1 coding sequence. The two transgenic strains are crossed to obtain double transgenic mice. The expression of MZB1 can be induced in the double transgenic mice by the administration of 1 μg/ml of doxycycline.

Development, function and homeostasis of different B cells subsets, FO B cells, MZ B cells, and B1 B cells are examined in MZB1 transgenic and non-transgenic control mice. FACS analysis reveals the relative abundance of each subset at different stages of develop as well as the surface phenotype of the different subsets. Functional assays such as proliferation assays and antibody production assays, in the presence and absence of stimuli, reveal the function and homeostasis of the different subsets. In particular, the role of MZB1 in B cell self-renewal is determined. The development of spontaneous or experimentally induced autoimmunity is monitored in MZB1 transgenic and non-transgenic control mice, as well as MZB1 transgenic mice crossed to mice which are predisposed to develop autoimmune conditions.

2.4.4 Generation and Characterization of Transgenic Mice with T Cell-Specific MZB1 Expression 2.4.4.1 Generation of Transgenic Mice Expressing MZB1 Under the Control of lck-Promoter MZB1 was shown to be expressed not only in B cell tissues, but MZB1 protein was as well detected in fetal thymus derived DN2 and DN3 cells and the not yet committed DN1 T cell precursors originating from adult thymus. In all further T cell populations tested so far, including immature as well as mature stages of T cell development, MZB1 expression was found to be absent. To investigate the impact of ectopic MZB1 expression in peripheral T cells with respect to its possible roles in lymphocyte signaling and the regulation of cell proliferation, transgenic mice were generated in which the MZB1 transgene is specifically expressed in T cells. Briefly, murine MZB1 cDNA was inserted into the pick-hGH transgenic vector (Garvin et al., 1990), which contains the proximal promoter of the lck gene for directing T cell-specific transcription and a portion of the hGH gene for the proper processing of mRNA by splicing and polyadenylation. The MZB1 transgenic fragment was microinjected into pronuclei of the oocytes of FVB/N mice. Expression of the MZB1 transgene was detected in three independent founder lines (M3, F38 and F47) by PCR assays and immunoblot analysis (FIG. 39 and data not shown). All experiments to investigate the phenotype of ectopic MZB1 expression in murine peripheral T cells were carried out with the three transgenic mouse lines, M3, F38 and F47, after backcrossing them with the inbred strain C57BL/6J (Jackson Laboratories). In every investigation performed in this course, transgenic mice (MZB1-transgene) were compared with their corresponding non-transgenic littermates, referred to as "wt" (wild type). As only data is presented with equal results for all of the three transgenic lines, the data of line M3, if not stated differently, is representatively displayed in all further experiments.

In order to examine the expression pattern of ectopically transcribed MZB1 in different T cell subsets isolated from transgenic mice, an immunoblot analysis with MZB1- and GAPDH-specific antibodies was performed (FIG. 39) according to standard conditions. 5-6 weeks old transgenic mice were sacrificed and thymus derived double negative (DN; $CD4^-$ and $CD8^-$), double positive (DP; $CD4^+$ and $CD8^+$) as well as $CD4^+$ and $CD8^+$ single positive T cells were enriched by FACS sorting according to their cell surface markers. In addition, $CD4^+$ as well as $CD8^+$ single positive peripheral T cells were isolated from transgenic mice derived lymph node and spleen, using FACS sorting.

MZB1 protein was shown to be expressed in all of the transgenic T cell subsets tested, indicating a successful lck gene-promoter directed, T cell-specific transcription of the MZB1-transgene (FIG. 39). In a further analysis, MZB1 expression was examined in thymic, splenic and lymph node-derived single positive T cells originating from transgenic and wt mice. For this set of experiments, sacrificed transgenic mice and their corresponding wt littermates were 5-6 weeks of age and the enrichment of $CD4^+$ and $CD8^+$ single positive T cells was carried out using FACS sorting.

As depicted in FIG. 40, transgenic single positive T cells expressed MZB1 protein irrespective whether they originated from lymph node, spleen or thymus. In contrast, the analyzed wt derived T cells did not reveal any MZB1 expression. In summary, these results demonstrate the successful generation of transgenic mouse lines which ectopically express MZB1 in DN and DP thymic precursors as well as thymic, splenic and lymph node single positive T cells.

2.4.4.2 Ectopic MZB1 Expression in Peripheral T Cells Reveals a Change in Intracellular Ceramide Metabolism 2.4.4.2.1 Decreased Intracellular Ceramide Content in Transgenic Peripheral T Cells The siRNA-mediated attenuation of MZB1 expression in K46 cells exhibited an increase in proliferation rate and overall protein tyrosine phosphorylation of non-stimulated cells, as well as a rise in $Ca^{2+}$/mobilization following BCR stimulation. These data identify MZB1 as a putative inhibitory protein which might be involved in the regulation of BCR-signaling. As the lipid second messenger ceramide was shown to be entailed in biological processes like the regulation of proliferation and furthermore was demonstrated to mediate BCR-induced apoptosis in WEHI 231 immature B cells, the question arose whether the ectopic expression of MZB1 could influence the intracellular ceramide content in transgenic, peripheral T cells.

Intracellular ceramide levels in non-stimulated as well as TCR-stimulated $CD4^+$ splenic T cells derived of wt or transgenic mice were quantified by the diacylglycerol (DAG) kinase assay as previously described (Tonnetti et al., 1999). In brief, FACS sorted $CD4^+$ splenocytes were left untreated or induced with α-CD28, α-CD3ε or both for 36 hours. Cells were harvested and endogenous ceramide was extracted as described in chapter 5.22. Quantification of the sphingomyelin-derived ceramide was accomplished by incubation of the dissolved lipids with *Escherichia coli* DAG kinase and [γ-$^{32}$P]ATP. The resulting [$^{32}$P]ceramide was quantified using a phosphor-imager system (Fuji) and the AlphaImager™-quantification software (Alpha Innotech) following thin-layer chromatography (TLC)

In non-stimulated $CD4^+$ splenic T cells, the ectopic expression of MZB1 resulted in an approximately two-fold downregulation of the intracellular ceramide content in comparison to wt cells (FIG. 41). Splenocytes of wt origin, responded to TCR stimulation with modest reduction of endogenous ceramide, prompting a maximal 1.5 fold downregulation of the lipid second messenger after induction with α-CD3ε, (0.3 µg/ml) and α-CD28 (1.0 µg/ml). In contrast, transgenic splenocytes replied with a 1.5 fold reduction of intracellular ceramide to stimulation with α-CD3ε (0.3 µg/ml) followed by a further decrease in ceramide content (3.5 fold compared to non-stimulated), if α-CD28 (1.0 µg/ml), providing a co-stimulatory signal, was added in addition (FIG. 41). In α-CD3ε (0.3 µg/ml) and α-CD28 (1.0 µg/ml) stimulated wt and transgenic splenocytes, the endogenous ceramide levels in transgenic cells were found to be reduced by a factor of 4-4.5 fold compared to wt T cells. The results presented in FIG. 41 indicate that ectopic expression of MZB1 in peripheral $CD4^+$ T cells causes a decrease in intracellular ceramide levels in the absence of a stimulus. This effect is even more pronounced if cells receive a TCR signal in combination with a co-stimulatory, secondary signal mediated by CD28.

In order to investigate whether the observed effects on ceramide metabolism upon ectopic MZB1 expression might be restricted to lymphocytes, ceramide quantification experiments were performed using a NIH 3T3 murine fibroblast cell line stably expressing FLAG-MZB1 (NIH 3T3::FLAG-MZB1). NIH 3T3 as well as NIH 3T3::FLAG MZB1 fibroblasts were grown to confluence in the absence of stimulation and harvested. Intracellular ceramide was extracted and quantified as described above.

The non-stimulated fibroblastic cells, irrespective whether MZB1 is expressed or not, contained equal amounts of intracellular ceramide (FIG. 42), suggesting that the ceramide reduction observed in transgenic T cells might be due to a lymphocyte-specific role of MZB1. This would be in accordance with its expression pattern, being predominantly present in early T cell precursors as well as the MZ and B-1 B cell subsets. Furthermore, data obtained from size exclusion chromatography indicated that MZB1 is part of a 220 kDa complex in lymphoid cells but not in NIH 313 fibroblasts (data not shown), supporting the notion that interaction partners or other factors required for MZB1 function may be missing in NIH 3T3 cells.

In summary these experiments indicate that ectopic expression of MZB1 in non-stimulated $CD4^+$ splenocytes resulted in a reduction of endogenous ceramide amounts but had no effect in NIH 3T3 fibroblasts. A co-stimulatory signal in combination with TCR-engagement further augments these effects, indicating that ectopically expressed MZB1 is likely associated with TCR-signaling in peripheral T cells.

2.4.4.2.2 Unchanged Activity of Acid as Well as Neutral Sphingomyelinases in Transgenic Peripheral T Cells Sphingomyelinases are enzymes that catalyze the hydrolysis of sphingomyelin (ceramide phosphorylcholin) into ceramide and phosphorylcholin. The reaction is formally similar to that of a phospholipase C. These enzymes appear to be especially interesting as being involved in the sphingomyelin signal transduction pathway, mediating signals e.g. by virtue of the lipid second messenger ceramide and regulating cellular processes like apoptosis, cell differentiation and cell proliferation. Sphingomyelinases, which are thought to be, apart from de novo synthesis, a major source of intracellular ceramide are classified according to their pH optimum into five categories, namely the acid sphingomyelinases (A-SMases), the secretory sphingomyelinases (S-SMases), neutral sphingomyelinases (N-SMases; can be subdivided into $Mg^{2+}$-dependent and -independent), alkaline sphingomyelinases (B-SMases) and the group of bacterial sphingomyelinase-phospholipase C enzymes. In contrast to the other classes of SMases, A-SMase and N-SMase participate in signal transduction and promote, due to their rapid activation by diverse stress stimuli, an increase in cellular ceramide levels over a period of minutes to hours. It was shown that ectopic exression of MZB1 in peripheral T cells decreased intracellular ceramide levels in non-stimulated and, even more pronounced, in TCR-stimulated cells, raising the possibility that MZB1 might regulate the activity of SMases.

The quantification of SMase activity was performed according to a protocol previously described by Wiegmann and coworkers (Wiegmann et al., 1994). In short, MACS®-purified $CD4^+$ splenic T cells of wt and transgenic origin were cultured in the absence or in the presence of α-CD3c (0.3 µg/ml) and α-CD28 (1.0 µg/ml). After 36 h, non-stimulated and TCR-induced cells were harvested, lysed and the cellular extracts (50 µg total protein) were incubated in the appropriate buffer conditions, being specified by a pH of 5.0 for acid- and a pH of 7.4 for neutral-SMases. Prior to incubation, [N-methyl-$^{14}$C]sphingomyelin (Amersham/GE Healthcare) as radioactively labeled substrate was added. The amount of $C^{14}$-labeled phosphorylcholine produced from [$^{14}$C]sphingomyelin was measured by scintillation counting.

As depicted in FIG. 43, the ectopic expression of MZB1 in $CD4^+$ peripheral T cells seems to have no impact on A-SMase activity, irrespective whether cells were TCR-induced or left untreated. Moreover, A-SMase activity stayed rather unchanged following TCR stimulation, suggesting that acid-SMase appears not to be involved in TCR-signaling. In a second set of experiments, no change in A-SMase activity between wt and transgenic cells could be observed (FIG. 44).

In contrast to the results presented for acid-SMase activity, the measured turnover rate of neutral-SMase was found significantly decreased for both wt and transgenic cells following TCR stimulation. These results indicate that TCR-signaling in combination with a co-stimulatory signal (CD28) decreases N-SMase activity in general, irrespective whether MZB1 is expressed or not.

These findings suggest that transgenic expression of MZB1 in peripheral T cells has no impact on the activity of either acid- or neutral-SMases. Since sphingolipid metabolism is very complex, involving several alternative routes for the anabolism as well as the catabolism of the lipid second messenger ceramide, the decrease in intracellular ceramide levels observed in transgenic $CD4^+$ T cells might be attributed to the influence of ectopically expressed MZB1 on enzymes other than acid- or neutral-SMase. Further experiments examining the activity of e.g. ceramidases, ceramide synthase or other classes of SMases will be performed in order to explain the reduced ceramide levels detected in transgenic T cells.

2.4.4.3 Transgenic Expression of MZB1 Increases Proliferation in TCR-Stimulated Peripheral T Cells The intracellular ceramide content, which was shown to be anti-proliferative and pro-apoptotic if increased by agonist- and stress-induced signals, was demonstrated to be decreased especially in TCR-stimulated peripheral T cells ectopically expressing MZB1. These results suggest a possible impact of transgenic transcribed MZB1 on proliferation and/or apoptosis, operating as a pro-proliferative and/or an anti-apoptotic factor, mediating a reduction of endogenous ceramide levels. To test this hypothesis, in a first series of experiments, the proliferative capacity of transgenic peripheral T cells was compared to the corresponding wt controls. Cell proliferation was measured using [$^3$H] thymidine incorporation as described previously. In brief, utilizing a 96 well format to determine the relative rate of radioactive [$^3$H]thymidine assimilation, reflecting the rate of proliferation, TCR-stimulated as well as non-stimulated wt, and transgenic $CD4^+$ T cells derived from lymph node or spleen were pulse-labeled with 1.5 μCi [$^3$H]thymidine/well for 18 h and the mean [$^3$H] incorporation of triplicate cultures was assayed by scintillation counting.

As depicted in FIG. 45, α-CD28-stimulated wt and transgenic $CD4^+$ lymph node T cells proliferated equally fast, while transgenic $CD4^+$ T cells divided 1.5-fold faster following α-CD3ε-stimulation and twice as fast if left untreated. Taking into account that the measured proliferation rate for all of the samples, treated with either exclusively α-CD28 or exclusively α-CD3ε or none, was found to be at low level, the observed differences in proliferation rate have to be considered as modest. In contrast, if stimulated with both α-CD28 and α-CD3ε, transgenic $CD4^+$ T cells proliferated 6.5-fold faster than the wt control, consistent with the results from the ceramide-assays in which the most pronounced difference between wt and transgenic cells was observed in CD28- and CD3ε-double-stimulated T cells. Compared to the wt control, transgenic T cells seemed to be more sensitive to α-CD28 stimulation in the presence of an α-CD3ε-mediated TCR signal. Whereas the wt T cells revealed no increase in proliferation when stimulated with α-CD28 in addition to α-CD3ε, the transgenic $CD4^+$ T cells did (FIG. 45).

In order to confirm the above results, an analogous series of experiments was performed with wt as well as transgenic $CD4^+$ splenocytes. Similar to lymph node derived T cells, both wt and transgenic $CD4^+$ splenocytes exhibited an unchanged to modest difference in proliferation rate if left untreated, or stimulated with either α-CD3ε or α-CD28 (FIG. 46). If $CD4^+$ splenocytes were stimulated with both α-CD3ε and α-CD28, transgenic T cells exhibited a significant increase in cell proliferation (5.5 fold) in comparison to wt control (FIG. 46). These results confirm the notion that ectopic expression of MZB1 in peripheral T cells, irrespective if derived from spleen or lymph node, results in a cellular state of changed responsiveness to TCR-ligation in conjunction with a co-stimulatory signal provided by CD28 (FIGS. 45 and 46).

The [$^3$H]thymidine incorporation experiments were repeated as well with an increased α-CD28-(0.3 μg/ml) but an unchanged α-CD3ε-concentration (0.3 μg/ml), exhibiting comparable results for splenic as well as lymph node derived $CD4^+$ T cells (FIG. 47).

The stimulation with both α-CD3ε (0.3 μg/ml) and α-CD28 (0.3 μg/ml), resulted, in the case of $CD4^+$ transgenic T cells, in an approximately 4 fold increase in proliferation compared to CD3ε-single stimulated cells and a 20 fold higher [$^3$H]thymidine incorporation compared to the untreated control (FIG. 47). The results for both lymph node and splenic $CD4^+$ T cells are similar to those obtained in the previous experiments using α-CD28 at a concentration of 0.1 μg/ml (FIGS. 45 and 46). These data indicate that the conditions chosen in the first set of experiments, 0.3 μg/ml of α-CD3ε and 0.1 μg/ml of α-CD28, offered maximal stimulation to transgenic T cells. In contrast, upon stimulation of the TCR in conjunction with a co-stimulatory signal, using the lower α-CD28 concentration (0.1 μg/ml), wt $CD4^+$ T cells did not exhibit a further increase in proliferation compared to α-CD3ε-single stimulated cells (FIGS. 45 and 46). Only when α-CD28 concentration was raised to 0.3 μg/ml, did wt T cells respond to stimulation with both α-CD3ε (0.3 μg/ml) and α-CD28 (0.3 μg/ml) with an approximately 3 fold increase in proliferation compared to α-CD3ε-single stimulated wt cells (FIG. 47). Moreover, if induced with α-CD3ε (0.3 μg/ml) and the higher concentration of α-CD28 (0.3 μg/ml), splenic as well as lymph node derived transgenic T cells displayed a 2.5 fold faster proliferation rate compared to the wt controls (FIG. 47), which is consistent with the results obtained in the first series of experiments, revealing a 5.5 to 6.5 fold increased in [$^3$H]thymidine incorporation in TCR and α-CD28 (0.1 μg/ml) stimulated transgenic T cells (FIGS. 45 and 46). This reduction from a 6.5 fold (low α-CD28 concentration) to a 2.5 fold (high α-CD28 concentration) difference in proliferation, observed in the second series of experiments might be attributed to the changed conditions, using an increased α-CD28 (0.3 μg/ml) concentration.

In summary, these results suggest that transgenic peripheral T cells respond to TCR-signaling, especially when provided with a co-stimulatory signal, with a significantly increased proliferation rate in comparison to wt T cells. Moreover, compared to wt controls, transgenic T cells responsed to a lower concentration of α-CD28 μg/ml), suggesting that ectopic MZB1 expression enhanced the reactiveness of T cells towards TCR-signaling.

In order to show that the effects observed in [$^3$H]thymidine incorporation experiments are due to an impact of ectopically expressed MZB1 on proliferation and not apoptosis, TdT-mediated dUTP nick end labeling (TUNEL) assays with stimulated wt and transgenic, peripheral T cells were performed.

As depicted in FIG. 48, the TUNEL assay performed with TCR-stimulated wt and transgenic peripheral T cells of splenic origin revealed no obvious differences between the tested samples with respect to apoptosis. After 24 hours of stimulation with either α-CD3c (0.3 µg/ml) or α-CD3ε (0.3 µg/ml) in conjunction with α-CD28 (0.1 µg/ml), the vast majority of cells (>95%), whether isolated from wt or transgenic animals, remained TUNEL negative (FIG. 48). In the wt control, between 3.5% (α-CD3ε- and α-CD28-) and 4.9% (α-CD30 of the cells entered the final stages of apoptosis. In case of the transgenic T cells, the numbers were slightly reduced and ranged between 2.7% (α-CD3ε- and α-CD28) and 2.8% (α-CD3ε). This suggest that ectopic expression of MZB1 in peripheral T cells exerts only very modest influences on apoptosis.

In summary, ectopically expressed MZB1 has an effect on cell proliferation in TCR-stimulated CD4$^+$ peripheral T cells; apoptosis does not seem to be affected. However, since the percentage of apoptotic cells detected following 24 hours of TCR stimulation was very low in both the wt and the transgenic cells (FIG. 48), further conditions inducing more pronounced programmed cell death will be tested.

2.4.4.4 Transgenic MZB1 Expression in Peripheral T Cells Augments Intracellular Calcium Release Upon TCR Stimulation The basic steps of BCR and TCR signal transduction proceed in a fairly parallel way. Similar to resting B cells, the concentration of free intracellular $Ca^{2+}$ is kept low and constant in non-stimulated T cells. Engagement of the TCR results in the recruitment of adaptor molecules and kinases, ultimately leading to tyrosine phosphorylation of PLC-γ and an increase in intracellular $Ca^{2+}$. The activation of PLC-γ prompts the generation of DAG and $IP_3$, leading to the depletion of $Ca^{2+}$ from intracellular stores and finally triggering the entry of $Ca^{2+}$ across channels in the plasma membrane, commonly referred to as calcium release-activated $Ca^{2+}$ (CRAC) channels. The ensuing sustained intracellular $Ca^{2+}$ elevation activates transcriptional pathways required for proliferation and effector immune function, both of which are a hallmark of activated B as well as T cells. Hence, the robustness of increase in intracellular $Ca^{2+}$ reflects the strength of the received TCR-mediated signal. The ectopic expression of MZB1 in peripheral T cells led to a decrease in intracellular ceramide levels and an increase of cell proliferation in T cells stimulated simultaneously with α-CD3ε and α-CD28. Since the phenotypes observed for transgenic T cells are the most pronounced when the cells were stimulated by a TCR signal, indicating a possible role of MZB1 as an activator of TCR-signaling. In order to address the issue whether ectopic expression of MZB1 in peripheral T cells changes the TCR-signaling capacity of these cells, $Ca^{2+}$ release following TCR-engagement was compared in wt and transgenic CD4$^+$ splenocytes. Relative levels of intracellular $Ca^{2+}$ were measured by fluorescence-activated cell sorting (FACS) analysis of Indo-1 AM (Molecular Probes) loaded cells. $Ca^{2+}$-response was either induced by addition of α-CD3ε at a final concentration of 10 µg/ml or by adding both, α-CD3ε (10 µg/ml) and α-CD28 (5 µg/ml). The $Ca^{2+}$-concentration of the used RPMI-media remained unchanged at a value of 2 mM $Ca^{2+}$.

As depicted in FIG. 49, there were only modest differences in $Ca^{2+}$ flux of α-CD3ε-stimulated wt and transgenic T cells. In contrast, a significant increase in $Ca^{2+}$ mobilization in the transgenic cells compared to wt control was observed when the cells were stimulated through both TCR and CD28 (FIG. 50). These data are consistent with the observed phenotypes of a marked reduction in intracellular ceramide levels and a prominently increase in cell proliferation in TCR and CD28-stimulated transgenic T cells compared to wt control cells, suggesting an impact of ectopically expressed MZB1 on the TCR-signaling machinery. Notably, for all phenotypes associated with transgenic MZB1 expression in T cells observed so far, in addition to TCR ligation, a co-stimulatory signal mediated by CD28 is required. Consequently, the possibility that transgenic MZB1 expression increases the amount of cell-surface TCR molecules and hence leads to the observed increase in $Ca^{2+}$ mobilization can be fairly safely ruled out. Further FACS experiments will be performed in order to investigate the influence of ectopic MZB1 expression on CD28 surface expression on transgenic T cells.

Whether the significantly reduced ceramide levels in α-CD3ε- and α-CD28-induced transgenic T cells is be a cause or consequence of increased cell proliferation and augmented $Ca^{2+}$ flux, both detected in TCR- and CD28-stimulated cells, will be investigated.

Interestingly, whereas the RNA interference-mediated downregulation of MZB1 expression in K46 mature B cells suggested a possible role of MZB1 as an inhibitory modulator of BCR-signaling, attenuating Btk activity and hence reducing proliferation, tyrosine phosphorylation and $Ca^{2+}$-mobilization upon BCR-ligation, ectopically expressed MZB1 seems to play a different role in T lymphocytes. In the transgenic mice with T cell-restricted expression of MZB1, the protein appears to act as an activator of TCR-signaling, resulting in an increased cell proliferation and enhanced $Ca^{2+}$-mobilization following TCR/CD28 stimulation. The difference in cell type-specific functions of MZB1 in B and T cells might be explained, at least partially, but differences in cell type-specific interaction partners and/or other cellular factors. T cell-specific interaction partners can be identified by the same methods which led to the identification of interaction partners in B cells.

Since MZB1 apparently enhances TCR-mediated signaling (especially in the presence of co-stimulation through CD28) upon ectopic expression in T cells, activators and enhancers of MZB1 expression may be used to enable expression of MZB1 in T cells, thereby enhancing TCR-mediated signalling, in particular, in the presence of co-stimulation, such as that through CD28. Activators and enhancers of MZB1 expression may be used to enhance TCR-mediated signalling in T cells in vitro or in vivo. In one embodiment, the activators and enhancers of MZB1 expression may be used to treat diseases which are caused by and/or associated with T cell malfunctioning due to reduced or absent TCR signalling and/or co-stimulation, such as hereditary, spontaneous, and acquired immunodeficiencies. Activators and enhancers of MZB1 expression may also be used to enhance TCR-mediated signalling in T cells in order to increase the ease in establishing T cell clones with desired TCR specificities. For example, transgenic mice expressing MZB1 in T cells can be immunized with an antigen and antigen-specific T cells clones can be derived following in vitro stimulation(s). Alternatively, mice not transgenic for MZB1 can be immunized with an antigen, T cells can be isolated, transfected or transduced with an MZB1 expression vector in vitro, and stimulated in vitro through the TCR in order to generate T cell clones with desired antigen-specificity.

Since MZB1 appears to have different effects on BCR and TCR signalling in B cells and T cells, respectively, for certain applications, in particular certain in vivo applications, it may be desirable to deliver activators and/or enhancers of MZB1 expression in a cell type-specific manner.

REFERENCES

Baumgarth, N. et al (1999) Proc Natl Acad Sci USA 96, 2250-5.
Baumgarth, N. et al. (2000) J Exp Med 192, 271-80.
Boes, M. et al, (1998) J Exp Med 188, 2381-6.
Durfee, T. et al. (1993) Genes Dev 7, 555-69.
Garvin, A. M. et al (1990) Int Immunol 2, 173-80,
Huang, Y et al. (2004) J Biol Chem 279, 28827-30.
Huber, M. et al. (2000) J Immunol 165, 124-33.
Kim, K. J. et al. (1979) J Immunol 122, 549-54.
Leitges, M. et al. (1996) Science 273, 788-91.
Lopes-Carvalho T and Kearney J F (2004) Immunological Reviews 197:192-2005
Markowitz, D, et al. (1988) J Virol 62, 1120-4.
Martin F and Kearney J F (2000) Immunological Reviews 175:70-79
McCahill, A. et al. (2002) Mol Pharmacol 62, 1261-73.
Ochsenbein, A. F. et al. (1999a) Science 286, 2156-9.
Ochsenbein, A. F. et al. (1999b) J Exp Med 190, 1165-74.
Reynolds et al. (2004) Nat. Biotechnol. 22:326-330
Ron, D. et al. (1994) Proc Natl Acad Sci USA 91, 839-43.
Srivastava B et al. (2005) Seminars in Immunology 17:175-182
Tatiana A, et al. (1999) FEMS Microbiol. Lett. 174:247-250
Tonnetti, L. et al. (1999) J Exp Med 189, 1581-9.
Wiegmann, K. et al. (1994) Cell 78, 1005-15.

---

The invention claimed is:

1. A method of screening for a small molecule inhibitor of the expression or the positive regulatory activity on antibody production in B cells of an MZB1 polypeptide, which method comprises the steps of:
   (i) contacting in vitro a cell expressing the MZB1 polypeptide with one or more candidate small molecule compounds;
   (ii) comparing the expression and/or the positive regulatory activity on antibody production in B cells of the MZB1 polypeptide in the cell in the presence of the one or more candidate small molecule compounds to the cell in the absence of the one or more small molecule candidate compounds; and
   (iii) identifying small molecule compounds of (ii) which decrease the level of expression or the positive regulatory activity on antibody production in B cells of the MZB1 polypeptide in the cell in the presence of the one or more candidate small molecule compounds as compared to the cell in the absence of the one or more candidate small molecule compounds,
   wherein the MZB1 polypeptide comprises an amino acid sequence selected from the group consisting of:
   (a) the amino acid sequence as set forth in SEQ ID NO: 4,
   (b) the amino acid sequence encoded by the nucleotide sequence set forth in SEQ ID NO: 3,
   (c) an amino acid sequence of (a) or (b) further comprising an amino-terminal methionine,
   (d) an amino acid sequence which is a human ortholog of any of (a)-(c), optionally further comprising an amino-terminal methionine,
   wherein the polypeptide of (d) has the positive regulatory activity on antibody production in B cells of the polypeptide having the amino acid sequence of any one of (a)-(c).

2. The method of screening according to claim 1, wherein step (ii) comprises comparing the antibody production in B cells, or the inhibition of the antibody production in B cells, in the presence and absence of the one or more candidate compounds, and step (iii) comprises identifying compounds which decrease the antibody production in B cells.

3. The method of screening according to claim 1, wherein step (ii) comprises comparing the expression of the MZB1 polypeptide in the presence and absence of the one or more candidate compounds, and step (iii) comprises identifying compounds which decrease the expression of the MZB1 polypeptide.

4. The method of screening according to claim 1, wherein the MZB1 polypeptide comprises an amino acid sequence which is a human ortholog of any of (a)-(c), optionally further comprising an amino-terminal methionine, and has the positive regulatory activity on antibody production in B cells of the polypeptide having the amino acid sequence of any one of (a)-(c).

5. The method of screening according to claim 2, wherein the cell expressing the MZB1 polypeptide is an immune cell.

6. The method of screening according to claim 5, wherein the immune cell expressing the MZB1 polypeptide is a B cell.

7. The method of screening according to claim 6, wherein the B cell expressing the MZB1 polypeptide is a B cell involved in an autoimmune disease, wherein the autoimmune disease is psoriasis, arthritis, diabetes mellitus, multiple sclerosis, systemic lupus erythematosis, autoimmune thyroiditis, Sjogren's syndrome, Crohn's disease, ulcerative colitis, asthma, anemic asthma, Graves' disease, sarcoidosis, myasthenia gravis, rheumatoid arthritis, juvenile rheumatoid arthritis, or psoriatic arthritis.

* * * * *